United States Patent
Brown et al.

(10) Patent No.: US 10,217,938 B2
(45) Date of Patent: *Feb. 26, 2019

(54) HOLE TRANSPORT COMPOSITIONS AND RELATED DEVICES AND METHODS (I)

(71) Applicant: NISSAN CHEMICAL INDUSTRIES, LTD., Tokyo (JP)

(72) Inventors: Christopher T. Brown, Redwood, CA (US); Neetu Chopra, Pittsburgh, PA (US); Christopher R. Knittel, Pittsburgh, PA (US); Mathew Mathai, Monroeville, PA (US); Venkataramanan Seshadri, Powell, OH (US); Jing Wang, Gibsonia, PA (US); Brian Woodworth, Cheswick, PA (US)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 77 days.

This patent is subject to a terminal disclaimer.

(21) Appl. No.: 15/410,615

(22) Filed: Jan. 19, 2017

(65) Prior Publication Data

US 2017/0186953 A1 Jun. 29, 2017

Related U.S. Application Data

(62) Division of application No. 13/175,710, filed on Jul. 1, 2011, now Pat. No. 9,577,194.

(Continued)

(51) Int. Cl.
*H01B 1/12* (2006.01)
*H01L 51/00* (2006.01)
(Continued)

(52) U.S. Cl.
CPC ........ *H01L 51/0007* (2013.01); *C07D 403/00* (2013.01); *C08F 226/02* (2013.01);
(Continued)

(58) Field of Classification Search
CPC .. H01B 1/00; H01B 1/12; H01L 51/00; C07D 403/00; C08L 65/00
See application file for complete search history.

(56) References Cited

U.S. PATENT DOCUMENTS 5,034,296 A 7/1991 Ong et al.
5,055,366 A 10/1991 Yu et al.
(Continued)

FOREIGN PATENT DOCUMENTS

EP 2 117 062 A1 11/2009
EP 2 194 582 A1 6/2010
(Continued)

OTHER PUBLICATIONS

Office Action received in connection with Japanese Patent Application No. 2013-518773, dated Mar. 11, 2015 (with translation).
(Continued)

*Primary Examiner* — Mark Kopec
(74) *Attorney, Agent, or Firm* — The Marbury Law Group, PLLC

(57) ABSTRACT

A composition comprising: at least one compound comprising a hole transporting core, wherein the core is covalently bonded to a first arylamine group and also covalently bonded to a second arylamine group different from the first, and wherein the compound is covalently bonded to at least one intractability group, wherein the intractability group is covalently bonded to the hole transporting core, the first arylamine group, the second arylamine group, or a combination thereof, and wherein the compound has a molecular weight of about 5,000 g/mole or less. Blended mixtures of (Continued)

arylamine compounds, including fluorene core compounds, can provide good film formation and stability when coated onto hole injection layers. Solution processing of OLEDs is a particularly important application.

16 Claims, 11 Drawing Sheets

Related U.S. Application Data

(60) Provisional application No. 61/448,579, filed on Mar. 2, 2011, provisional application No. 61/361,147, filed on Jul. 2, 2010.

(51) Int. Cl.
| | |
|---|---|
| C07D 403/00 | (2006.01) |
| H01L 51/50 | (2006.01) |
| C08F 226/02 | (2006.01) |
| C09B 57/00 | (2006.01) |
| C09B 69/10 | (2006.01) |
| C08G 73/02 | (2006.01) |
| C09D 11/102 | (2014.01) |
| C09D 11/106 | (2014.01) |
| C09D 11/52 | (2014.01) |

(52) U.S. Cl.
CPC ........ *C08G 73/0206* (2013.01); *C09B 57/008* (2013.01); *C09B 69/109* (2013.01); *C09D 11/102* (2013.01); *C09D 11/106* (2013.01); *C09D 11/52* (2013.01); *H01B 1/12* (2013.01); *H01L 51/0003* (2013.01); *H01L 51/006* (2013.01); *H01L 51/0039* (2013.01); *H01L 51/0043* (2013.01); *H01L 51/0059* (2013.01); *H01L 51/5004* (2013.01); *C08G 2261/222* (2013.01); *C08G 2261/312* (2013.01); *C08G 2261/3142* (2013.01); *C08G 2261/3162* (2013.01); *C08G 2261/364* (2013.01); *C08G 2261/512* (2013.01); *C08G 2261/76* (2013.01); *H01L 51/0074* (2013.01); *H01L 51/5056* (2013.01); *H01L 2251/552* (2013.01)

(56) References Cited

U.S. PATENT DOCUMENTS

| | | | |
|---|---|---|---|
| 5,149,609 A | 9/1992 | Yu et al. | |
| 5,589,320 A | 12/1996 | Ohnishi et al. | |
| 5,759,709 A | 6/1998 | Doi et al. | |
| 5,895,692 A | 4/1999 | Shirasaki et al. | |
| 7,125,633 B2 | 10/2006 | Mishra et al. | |
| 7,893,160 B2 | 2/2011 | Inbasekaran et al. | |
| 7,956,350 B2 | 6/2011 | Inbasekaran et al. | |
| 8,535,974 B2 | 9/2013 | Brown et al. | |
| 8,779,137 B2 | 7/2014 | Kobayshi | |
| 9,577,194 B2* | 2/2017 | Brown ................ | H01L 51/0059 |
| 2004/0106004 A1 | 6/2004 | Li | |
| 2005/0136288 A1 | 6/2005 | Lee et al. | |
| 2005/0184287 A1 | 8/2005 | Herron et al. | |
| 2006/0032528 A1 | 2/2006 | Wang | |
| 2006/0078761 A1 | 4/2006 | Williams et al. | |
| 2007/0063191 A1* | 3/2007 | Inbasekaran ............ | C07C 25/22 257/40 |
| 2008/0248313 A1 | 10/2008 | Seshadri et al. | |
| 2008/0286566 A1 | 11/2008 | Prakash | |
| 2009/0159877 A1 | 6/2009 | Meng | |
| 2009/0230361 A1 | 9/2009 | Seshadri et al. | |
| 2009/0256117 A1 | 10/2009 | Seshadri et al. | |
| 2010/0010900 A1 | 1/2010 | Lee et al. | |
| 2010/0072462 A1 | 3/2010 | Brown et al. | |
| 2010/0108594 A1 | 5/2010 | Wright | |
| 2010/0187500 A1 | 7/2010 | Prakash | |
| 2010/0187510 A1 | 7/2010 | Rostovtsev | |
| 2010/0207109 A1 | 8/2010 | Hsu et al. | |
| 2010/0213446 A1 | 8/2010 | Zhang et al. | |
| 2010/0244665 A1 | 9/2010 | Herron et al. | |
| 2010/0273007 A1 | 10/2010 | Sheina | |
| 2010/0292399 A1 | 11/2010 | Brown et al. | |
| 2011/0017988 A1* | 1/2011 | Yasukawa ............. | H01L 51/004 257/40 |
| 2011/0028644 A1 | 2/2011 | Brown et al. | |
| 2011/0147725 A1 | 6/2011 | Seshadri | |
| 2012/0003790 A1 | 1/2012 | Brown et al. | |

FOREIGN PATENT DOCUMENTS

| | | |
|---|---|---|
| JP | 2005-206817 | 8/2005 |
| JP | 2006-294319 | 10/2006 |
| JP | 2006-522860 | 10/2006 |
| JP | 2008-248241 | 10/2008 |
| JP | 2009-176963 | 8/2009 |
| JP | 2010-037312 | 2/2010 |
| WO | WO-97/33193 A2 | 9/1997 |
| WO | WO 2004/093154 | 10/2004 |
| WO | WO-2006/036755 A1 | 4/2006 |
| WO | WO-2006/086480 A2 | 8/2006 |
| WO | WO 2007/060854 | 5/2007 |
| WO | WO-2007/076146 A2 | 7/2007 |
| WO | WO-2007/079103 A2 | 7/2007 |
| WO | WO-2007/120143 A1 | 10/2007 |
| WO | WO-2007/145979 A2 | 12/2007 |
| WO | WO-2008/024378 A2 | 2/2008 |
| WO | WO-2008/024379 A2 | 2/2008 |
| WO | WO-2008/024380 A2 | 2/2008 |
| WO | WO-2008/073149 A2 | 6/2008 |
| WO | WO-2008/106210 A1 | 9/2008 |
| WO | WO-2008/150872 A1 | 12/2008 |
| WO | WO-2008/150943 A1 | 12/2008 |
| WO | WO-2009/018009 A1 | 2/2009 |
| WO | WO-2009/052085 A1 | 4/2009 |
| WO | WO-2009/055532 A1 | 4/2009 |
| WO | WO-2009/067419 A1 | 5/2009 |
| WO | WO-2009/097377 A1 | 8/2009 |
| WO | WO-2009/111339 A1 | 9/2009 |
| WO | WO-2009/111675 A1 | 9/2009 |
| WO | WO-2009/126918 A1 | 10/2009 |
| WO | WO-2009/133753 A1 | 11/2009 |
| WO | WO-2009/140570 A2 | 11/2009 |
| WO | WO-2010/051259 A1 | 5/2010 |
| WO | WO-2010/059240 A1 | 5/2010 |
| WO | WO-2010/059646 A2 | 5/2010 |
| WO | WO-2010/062558 A1 | 6/2010 |
| WO | WO-2010/093592 A1 | 8/2010 |
| WO | WO-2012/003482 A2 | 1/2012 |
| WO | WO-2012/003485 A2 | 1/2012 |

OTHER PUBLICATIONS

Office Action received in connection with Japanese Patent Application No. 2013-518772, dated Mar. 11, 2015 (with translation).
Search report (English translation only) received in connection with Taiwanese Patent Application No. 100123462; dated Mar. 10, 2015.
Notice of allowance received in connection with U.S. Appl. No. 13/868,924, dated Apr. 29, 2014.
Cheng et al., "Thermally Cross-Linkable Hole-Transporting Materials on Conducting Polymer: Synthesis, Characterization, and Applications for Polymer Light-Emitting Devices", Chemistry of Materials, vol. 20, No. 2, 2008, pp. 413-422.
International Search Report for International Application No. PCT/US2011/042865 dated Mar. 13, 2012.
Müller, et al., "Novel cross-linkable hole-transport monomer for use in organic light emitting diodes", Synthetic Metals, vol. 111-112, Jun. 1, 2000, pp. 31-34.
Yan et al., "Enhanced Polymer Light-Emitting Diode Performance Using a Crosslinked-Network Electron-Blocking Interlayer", Advanced Materials, vol. 16, No. 21, Nov. 4, 2004, pp. 1948-1953.
Ash, M., Handbook of Solvents, 2003, 2nd Ed., Synapse Information Resources, 3 pages (TOC).

(56) References Cited

OTHER PUBLICATIONS

Forrest, Steven R., "The Path to Ubiquitous and Low-Cost Organic Electronic Appliances on Plastic," Nature, 2004, vol. 428, pp. 911-918.

Friend, et al., "Electroluminescence in Conjugated Polymers," Nature, 1999, vol. 397, pp. 121-128.

Handbook of Solvents (Chemical), 2001, Edited by George Wypych, ChemTec Publishing, ISBN 1-895198-24-0, 14 pages (TOC).

Hansen, Charles M., Hansen Solubility Parameters: A Users Handbook, 2007, CRC Press, Taylor and Frances Group, 9 pages (TOC).

Highly Efficient OLEDS with Phosphorescent Materials, Edited by H. Yersin, 2008, Wiley-VCH Verlag GmbH & Co. KGaA, Weinheim, ISBN: 978-3-527-40594-7, 6 pages (TOC).

Industrial Solvents Handbook, 2003, 2nd Ed., Edited by N.P. Cheremisnoff, publisher Marcel Dekker, Inc., New York, 6 pages (TOC).

Invitation to Pay Additional Fees with Partial Search Report for Intl. Appl. No. PCT/US2011/042865 dated Jan. 2, 2012.

March's Advanced Organic Chemistry: Reactions, Mechanisms, and Structure, 6th Ed., Edited by Michael B. Smith and Jerry Mar. 2007, Wiley-Interscience a John Wiley & Sons, Inc. Publication, 4 pages (TOC).

Organic Light Emitting Devices: Synthesis, Properties, and Applications, 2006, Edited by Klaus Mullen and Ullrich Sherf, Wiley-VCH Verlag GmbH & Co. KGaA, Weinheim, ISBN 3-527-31218-8, 8 pages (TOC).

Organic Light Emitting Materials and Devices, 2007, Edited by Zhigang Li and Hong Meng, CRC Press, Taylor & Frances Group, 3 pages (TOC).

Shen, et al., "How to make Ohmic Contacts to Organic Semiconductors," ChemPhysChem, 2004, vol. 5, pp. 16-25.

Shirota et al., "Charge Carrier Transporting Molecular Materials and Their Applications in Devices," Chem. Rev. 2007, vol. 107, pp. 953-1010.

Tang et al., "Organic Electroluminescent Diodes," Appl. Phys. Lett., 1987, vol. 51, No. 12, pp. 913-915.

\* cited by examiner

Image on top of Plexcore® OC HIL 500X Magnification

Initial film formation on NAQ HIL (500x)

Pre-polymer by cross-linking reaction of PLX-D (500x), Film annealing 200C

Uv-Modified ink (500x)

Modified process (500x)

PLX-C (500X), film annealed at 200C (spots visible compared to Figure 7)

PLX-B (500x), Film annealing 200C (spots not visible compared to Figure 6)

Figure 9 – Chart with Table 2 (Example 11)

Lifetime testing

HOLE TRANSPORT COMPOSITIONS AND RELATED DEVICES AND METHODS (I)

RELATED APPLICATIONS

This application is a divisional of U.S. application Ser. No. 13/175,710, filed Jul. 1, 2011, now U.S. Pat. No. 9,577,194, which claims benefit of priority to U.S. Provisional application 61/361,147 filed Jul. 2, 2010, and also to U.S. Provisional application 61/448,579 filed Mar. 2, 2011, each of these disclosures are incorporated herein by reference in their entireties.

BACKGROUND

A need exists to provide better organic light emitting devices (OLEDs) including better materials used in the devices. In particular, better OLED devices and materials, including hole transporting materials (HTMs), are needed. An OLED operation is based on injection, transport and recombination of two types of charge carriers: holes and electrons. It is important in an OLED device to control the injection and transport of these two types of carriers so as to enable the recombination to occur in the EML where the luminescent species are located. The location where these species meet and recombine can dictate the efficiency and lifetime of the device. Vapor processed OLED devices can adopt a multilayer strategy of using complex device architecture of 6-8 layers at times to effectively control and alter the charge carrier flow as needed to optimize performance. However, for solution processed devices, it can be more challenging to form multilayer structures as the solvent for a given layer can re-dissolve the previously applied layer. The vapor approach gives good performance and has seen some adoption in the industry, but solution processing holds the promise of significantly higher throughput and lower costs and, because of that, is of great commercial promise.

In particular, a need exists for a good platform system to control properties of hole injection and transport layers such as solubility, thermal stability, and electronic energy levels such as HOMO and LUMO, so that the materials can be adapted for different applications and to function with different materials such as light emitting layers, photoactive layers, and electrodes. In particular, good solubility and intractability properties are important. The ability to formulate the system for a particular application and provide the required balance of properties are also important.

Additional background material can be found in, for example, (a) Charge carrier transporting molecular materials and their applications in devices, Shirota, et al., *Chem. Rev.*, 2007, 107, 953-1010, (b) Organic electroluminescent diodes, Tang, et al., *Appl. Phys. Lett.* 1987, 51, 913-915.

SUMMARY

Embodiments described herein include, for example, compositions, devices, methods of making compositions and devices, methods of using compositions and devices, and kits. Compositions can be reactive compositions, ink compositions, solid or liquid compositions, and compositions formed after a reaction step, including a crosslinking, oligomerization, or polymerization step.

One embodiment provides a composition comprising: at least one first compound and at least one second compound different from the first, wherein the at least one first compound comprises a hole transporting core which is a fluorene core, wherein the hole transporting core is covalently bonded to a first arylamine group and also covalently bonded to a second arylamine group, and wherein the core is further covalently bonded to at least two solubilizing groups comprising at least four carbon atoms, and wherein the solubilizing groups are optionally substituted with intractability groups; wherein the at least one second compound comprises a hole transporting core which is a fluorene core, wherein the hole transporting core is covalently bonded to a first arylamine group and also covalently bonded to a second arylamine group, wherein the second compound further comprises at least one intractability group which may be bonded to the first arylamine group, the second arylamine group, or both; and wherein the first and second compounds have molecular weight of about 5,000 g/mole or less.

In one embodiment, the relative amounts of the first and second compounds are about 99:1 to about 1:99 by weight, respectively. In one embodiment, the relative amounts of the first and second compounds are about 90:1 to about 10:90 by weight, respectively. In one embodiment, the relative amounts of the first and second compounds are about 20:80 to about 40:60 by weight, respectively. In one embodiment, the relative amounts of the first and second compounds are about 99:1 to about 80:20 by weight, respectively. In one embodiment, the relative amounts of the first and second compounds are about 40:60 to about 60:40 by weight, respectively. In one embodiment, the molecular weight of the first compound is about 2,000 or less, and the molecular weight of the second compound is about 2,000 or less. In one embodiment, the molecular weight of the first compound is about 1,000 or less, and the molecular weight of the second compound is about 1,000 or less.

In one embodiment, the first compound has only two arylamine groups, and the second compound has only two arylamine groups. In one embodiment, the core fluorene group of the first and second compounds are bonded to the arylamines at the 2 and 7 positions of the fluorene group and the core fluorene group is bonded to the solubilizing groups at the 9 position. In one embodiment, for the first compound the two solubilizing groups each comprise at least eight carbon atoms. In one embodiment, the second compound comprises at least one intractability group which is bonded to the first arylamine group, and at least one intractability group which is bonded to the second arylamine group.

In one embodiment, the intractability group for the second compound is vinyl. In one embodiment, the intractability group for the second compound is vinyl which is covalently bonded to a phenyl ring to form a styrene unit. In one embodiment, for the first and second compounds, the first and send arylamine groups are the same group. In one embodiment, the two solubilizing groups bonded to the fluorene core are the same groups.

In one embodiment, at least one of the arylamine groups comprises an optionally substituted naphthyl group bonded to nitrogen. In one embodiment, at least one of the arylamine groups comprises an both an optionally substituted naphthyl group and an optionally substituted phenyl group bonded to nitrogen. In one embodiment, the first and second compounds have a solubility of at least 5 wt. %. In one embodiment, the intractable groups are polymerizable groups.

In one embodiment, for the first compound, the solubilizing group is substituted with the intractability group, and for the second compound the core further comprises at least two solubilizing groups comprising at least four carbon atoms. In one embodiment, the relative amounts of the first and second compounds are about 20:80 to about 40:60 by weight, respectively. In one embodiment, the relative amounts of the first and second compounds are about 25:75 to about 35:65 by weight, respectively. In one embodiment, for the first compound the intractability group is benzocyclobutane. In one embodiment, for the second compound the core further comprises at least two solubilizing groups comprising at least eight carbon atoms. In one embodiment, for the second compound the solubilizing groups do not comprise intractability groups. In one embodiment, the first compound and the second compound comprise different intractability groups.

In one embodiment, the first compound is represented by:

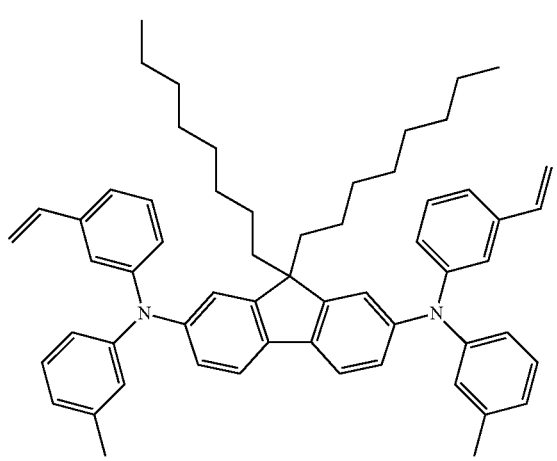

In one embodiment, the second compound is represented by:

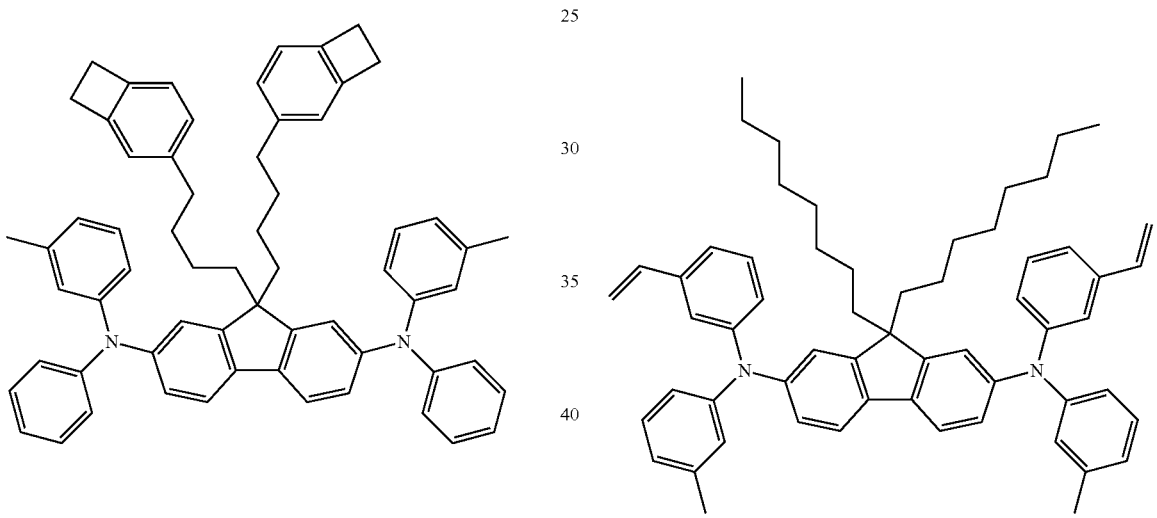

In one embodiment, the first compound is represented by

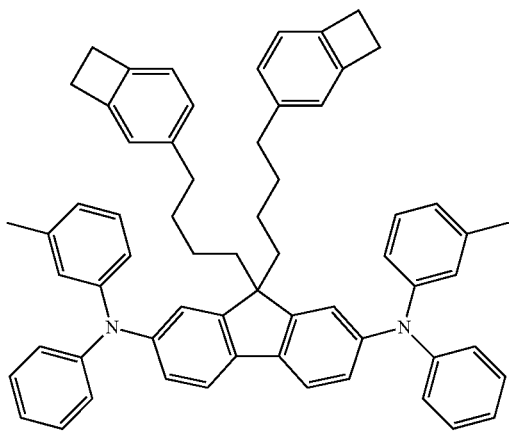

and the second compound is represented by:

In one embodiment, for the first compound, the solubilizing group of the core is unsubstituted with intractability group. In one embodiment, the relative amounts of the first and second compounds are about 99:1 to about 80:20 by weight, respectively. In one embodiment, the relative amounts of the first and second compounds are about 95:5 to about 85:15 by weight, respectively. In one embodiment, for the first compound the intractability group is on at least one of the arylamine groups and is vinyl. In one embodiment, for the second compound the core further comprises to groups bonded to fluorene which are C3, C2, or C1 groups. In one embodiment, for the second compound intractability groups bonded to the first and second arylamine which are vinyl bonded to phenyl to form a para-styrene. In one embodiment, the first compound does not comprise intractability groups bonded to the core. In one embodiment, the first compound is represented by:

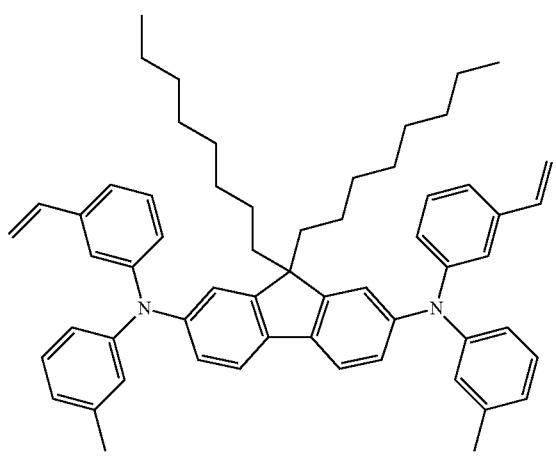 [SMILES: C=Cc1cccc(N(c2cccc(C)c2)c2ccc3c(c2)C(CCCCCCCC)(CCCCCCCC)c2cc(N(c4cccc(C)c4)c4cccc(C=C)c4)ccc2-3)c1]

In one embodiment, the second compound is represented by:

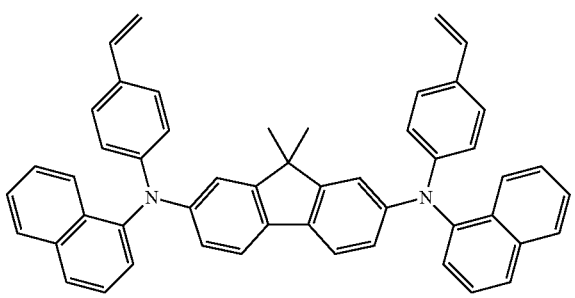 [SMILES: C=Cc1ccc(N(c2ccc3c(c2)C(C)(C)c2cc(N(c4ccc(C=C)cc4)c4cccc5ccccc45)ccc2-3)c2cccc3ccccc23)cc1]

In one embodiment, the first compound is represented by:

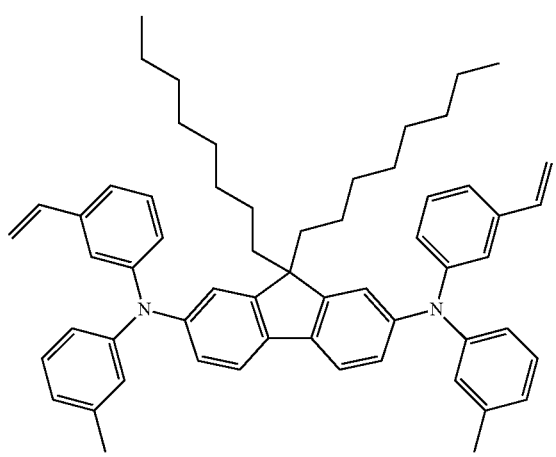 [SMILES: C=Cc1cccc(N(c2cccc(C)c2)c2ccc3c(c2)C(CCCCCCCC)(CCCCCCCC)c2cc(N(c4cccc(C)c4)c4cccc(C=C)c4)ccc2-3)c1]

and the second compound is represented by:

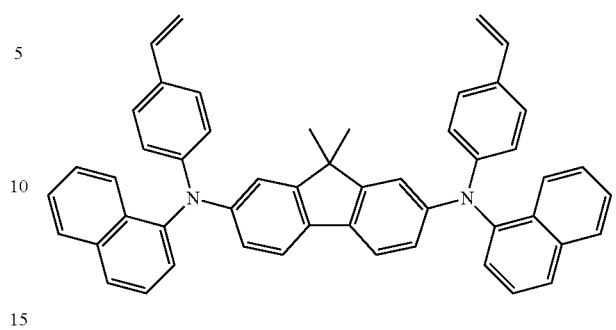

In one embodiment, for the first compound, the solubilizing group is substituted with the intractability group and the for the second compound, the core does not comprise at least two solubilizing groups comprising at least four carbon atoms. In one embodiment, the relative amounts of the first and second compounds are about 80:20 to about 20:80 by weight, respectively. In one embodiment, the relative amounts of the first and second compounds are about 60:40 to about 40:60 by weight, respectively. In one embodiment, for the first compound the intractability group is vinyl. In one embodiment, for the first compound the intractability group is vinyl bonded to a phenyl to form a styrene unit. In one embodiment, for the second compound the core further comprises to groups bonded to fluorene which are C3, C2, or C1 groups. In one embodiment, for the second compound intractability groups bonded to the first and second arylamine which are vinyl bonded to phenyl to form a para-styrene.

In one embodiment, the first compound is represented by:

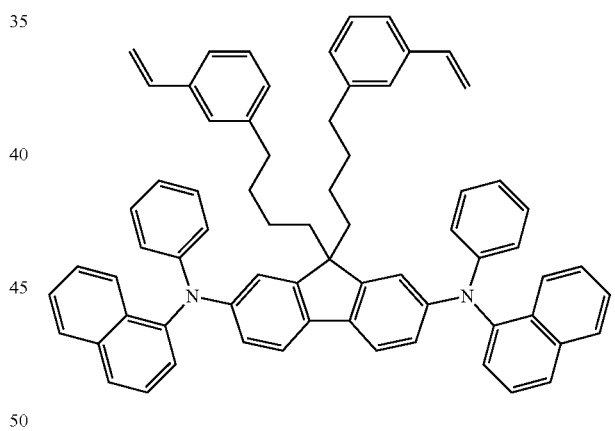

In one embodiment, the second compound is represented by:

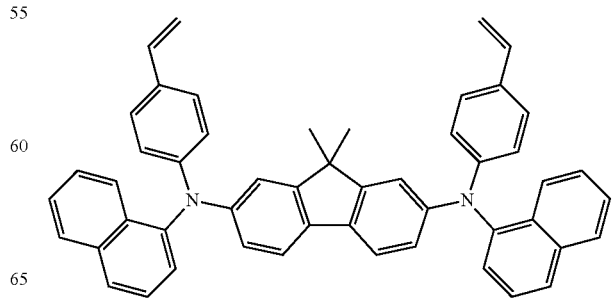

In one embodiment, the first compound is represented by:

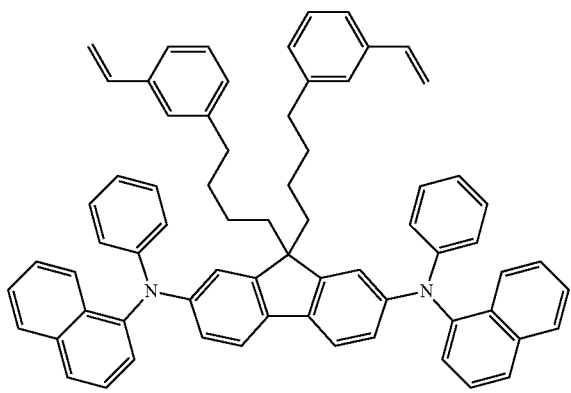 [SMILES: C=Cc1cccc(CCCCC2(CCCCc3cccc(C=C)c3)c3cc(N(c4ccccc4)c4cccc5ccccc45)ccc3-c3ccc(N(c4ccccc4)c4cccc5ccccc45)cc32)c1]

and the second compound is represented by:

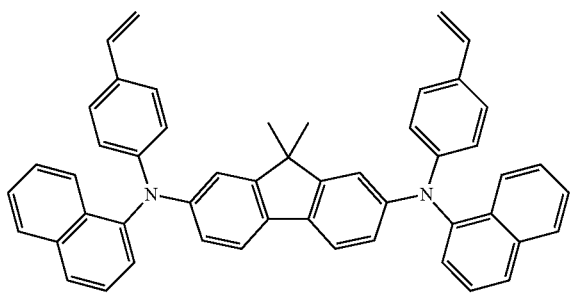 [SMILES: C=Cc1ccc(N(c2ccc3c(c2)C(C)(C)c2cc(N(c4ccc(C=C)cc4)c4cccc5ccccc45)ccc2-3)c2cccc3ccccc23)cc1]

In one embodiment, the composition further comprises a solvent system to form an ink.

In one embodiment, the composition further comprises a solvent system to form an ink, wherein the solid content of the ink is about 0.5 to about 5 wt/wt % total solids. In one embodiment, the composition further comprises a solvent system to form an ink, and the solvent system comprises toluene, o-xylene, chlorobenze, or mixtures thereof as solvent. In one embodiment, the intractable groups are polymerizable groups, and the polymerizable groups are reacted. In one embodiment, a composition is prepared by reaction of the first and second compounds of the composition as described herein. In one embodiment, the composition further comprises at least one third compound, different from the first and second compounds, which activates a polymerization reaction for the composition. In one embodiment, the composition further comprises at least one third compound, different from the first and second compounds, which comprises para-styrene units. In one embodiment, the composition further comprises at least one third arylamine compound, different from the first and second arylamine compounds, wherein the third arylamine compound has only one crosslinking group. In one embodiment, the composition further comprises at least one third arylamine compound, different from the first and second arylamine compounds, wherein the third arylamine compound has three or more crosslinking groups. In one embodiment, the composition further comprises at least one third arylamine compound, wherein the third arylamine compound has a lower LUMO and lower or similar HOMO compared to the first and second compounds.

Another embodiment provides a composition comprising: at least one first compound and at least one second compound different from the first, wherein the at least one first compound comprises a hole transporting core which is a fluorene core or a biphenyl core, wherein the hole transporting core is covalently bonded to a first arylamine group and also covalently bonded to a second arylamine group, and wherein the core is further covalently bonded to at least two solubilizing groups comprising at least four carbon atoms, and wherein the solubilizing groups are optionally substituted with intractability groups; wherein the at least one second compound comprises a hole transporting core which is a fluorene core or a biphenyl core, wherein the hole transporting core is covalently bonded to a first arylamine group and also covalently bonded to a second arylamine group, wherein the second compound further comprises at least one intractability group which may be bonded to the first arylamine group, the second arylamine group, or both; wherein the first and second compounds have molecular weight of about 5,000 g/mole or less.

Another embodiment provides for a composition comprising: at least one compound comprising a hole transporting core, wherein the core is covalently bonded to a first arylamine group and also covalently bonded to a second arylamine group, and wherein the compound is covalently bonded to at least one intractability group, wherein the intractability group is covalently bonded to the hole transporting core, the first arylamine group, the second arylamine group, or a combination thereof, and wherein the compound has a molecular weight of about 5,000 g/mole or less.

In one embodiment, the compound comprises at least three intractability groups, and at least one intractability group is covalently bonded to the hole transport core, and at least one intractability group is covalently bonded to the first arylamine group, and at least one intractability group is covalently bonded to the second arylamine group. In one embodiment, the intractability group is covalently bonded to the hole transport core but not the first aryl amine group or the second arylamine group. In one embodiment, the intractability group is covalently bonded to the first arylamine group, the second arylamine group, or both, but is not bonded to the hole transport core.

In one embodiment, the compound comprises one intractability group. In one embodiment, the compound comprises two intractability groups. In one embodiment, the compound comprises three or more intractability groups. In one embodiment, the compound's molecular weight is about 2,000 or less. In one embodiment, the compound's molecular weight is about 400 to about 2,000. In one embodiment, the compound's molecular weight is about 2,000 to about 5,000.

In one embodiment, the hole transporting core comprises at least two aryl or heteroaryl rings. In one embodiment, the hole transporting core comprises at least three aryl or heteroaryl rings. In one embodiment, the hole transport core comprises only carbocyclic rings. In one embodiment, the hole transport core comprises at least one spiro moiety. In one embodiment, the hole transport core comprises at least one thiophene moiety. In one embodiment, the hole transport core comprises at least two thiophene moieties. In one embodiment, the hole transport core comprises at least one benzodithiophene moiety. In one embodiment, the hole transport core comprises at least one heteroarylmoiety comprising at least one nitrogen. In one embodiment, the hole transport core comprises at least one heteroarylmoiety comprising at least two nitrogens. In one embodiment, the hole transport core comprises at least one piperazine core. In one embodiment, the hole transport core comprises at least one pyrrole ring. In one embodiment, the hole transport core comprises at least two pyrrole rings. In one embodiment, the hole transport core comprises at least one silole ring. In one embodiment, the hole transport core comprises at least two silole rings. In one embodiment, the hole transport core comprises at least three fused rings. In one embodiment, the hole transport core comprises at least five fused rings. In one embodiment, the hole transport core is functionalized with at least one solubilizing group. In one embodiment, the hole transport core is functionalized with at least two solubilizing groups. In one embodiment, the hole transport core is functionalized with at least one solubilizing group which has a least four carbon atoms. In one embodiment, the hole transport core is functionalized with at least one solubilizing group which as an alkylene group comprising at least four carbon atoms. In one embodiment, the first and second arylamine group are the same arylamine group. In one embodiment, each of the first and second arylamine groups are independently represented by —N(R1)(R2), wherein R1 and R2 are optionally substituted aryl or heteroaryl groups which may be the same or different.

In one embodiment, each of the first and second arylamine groups are independently represented by —N(R1)(R2), wherein at least one of R1 and R2 is an optionally substituted phenyl group. In one embodiment, each of the first and second arylamine groups are independently represented by —N(R1)(R2), wherein at least one of R1 and R2 is an optionally substituted biphenyl group. In one embodiment, each of the first and second arylamine groups are independently represented by —N(R1)(R2), wherein at least one of R1 and R2 is an optionally substituted carbazole group. In one embodiment, each of the first and second arylamine groups are independently represented by —N(R1)(R2), wherein —N(R1)(R2) form an optionally substituted carbazole group. In one embodiment, each of the first and second arylamine groups are independently represented by —N(R1)(R2), wherein at least one of R1 and R2 is an optionally substituted naphthyl group. In one embodiment, each of the first and second arylamine groups are independently represented by —N(R1)(R2), wherein at least one of R1 and R2 is an optionally substituted thienobenzene group. In one embodiment, each of the first and second arylamine groups are independently represented by —N(R1)(R2), wherein at least one of R1 and R2 is an optionally substituted fluorene group. In one embodiment, each of the first and second arylamine groups are independently represented by —N(R1)(R2), wherein at least one of R1 and R2 is an optionally substituted group comprising at least two fused aromatic rings.

In one embodiment, the intractability group comprises a crosslinking group. In one embodiment, the intractability group comprises a non-crosslinking group. In one embodiment, the intractability group comprises at least one ethylenically unsaturated moiety. In one embodiment, the intractability group comprises a vinyl group. In one embodiment, the intractability group comprises a benzocyclobutane group. In one embodiment, the intractability group comprises an indenyl group. In one embodiment, the intractability group comprises a quaternary ammonium group. In one embodiment, the intractability group comprises a quaternary ammonium group comprising a tetraarylborate anion. In one embodiment, the intractability group comprises a quaternary ammonium group comprising a pentafluorophenylborate anion.

In one embodiment, the compound has a glass transition temperature of about 200° C. or less. In one embodiment, the compound is a first compound, and the composition further comprises at least one additional second compound, different from the first compound, which activates a polymerization reaction for the composition.

In one embodiment, the compound is a first compound, and the composition further comprises at least one additional second compound, different from the first compound, which comprises para-styrene units. In one embodiment, the compound is a first compound, and the composition further comprises at least one additional second arylamine compound, different from the first arylamine compound, wherein the second arylamine compound has only one crosslinking group. In one embodiment, the compound is a first compound, and the composition further comprises at least one second arylamine compound, different from the first arylamine compound, wherein the second arylamine compound has three or more crosslinking groups. In one embodiment, the compound is a first compound, and the composition further comprises at least one second arylamine compound, wherein the second aryl amine compound has a lower LUMO and lower or similar HOMO compared to the first and compound. Another embodiment provides a method comprising: providing a substrate comprising a hole injection layer, coating the substrate with at least one ink comprising at least one hole transport material comprising intractability groups to form a coated substrate, heating the coated substrate.

In one embodiment, the ink is subjected to pre-crosslinking before coating the ink on the substrate. In one embodiment, the ink is subjected to thermal pre-crosslinking before coating the ink on the substrate. In one embodiment, the ink is subjected to thermal pre-crosslinking to form a gel before coating the ink on the substrate. In one embodiment, the ink is subjected to thermal pre-crosslinking at at least 150° C. to form a gel before coating the ink on the substrate. In one embodiment, the ink is subjected to UV light pre-crosslinking before coating the ink on the substrate. In one embodiment, the coated substrate is subjected to UV light to induce pre-crosslinking before heating the coated substrate. In one embodiment, the coated substrate is heated to at least 200° C. In one embodiment, the coated substrate is heated to at least 250° C.

In one embodiment, after heating the coated substrate shows a uniform defect free continuous film coated on top of a substrate coated with hole injection layer in the optical microscope. In one embodiment, after heating the coated substrate shows a uniform defect free continuous film coated on top of a substrate coated with a non-aqueous hole injection layer in the optical microscope. In one embodiment, after heating the coated substrate is stable to toluene solvent wash so that retains at least 90% of initial thickness after toluene is spun on the substrate for one minute and then dried for five minutes at 100° C. In one embodiment, after heating the coated substrate is stable to toluene solvent wash so that retains at least 95% of initial thickness after toluene is spun on the substrate for one minute and then dried for five minutes at 100° C. In one embodiment, the coating of the coated substrate before crosslinking shows a Tg of 200° C. or less. In one embodiment, the coating of the coated substrate before crosslinking shows a Tg of 150° C. or less.

In one embodiment, the hole injection layer is an aqueous hole injection layer. In one embodiment, the hole injection layer is a non-aqueous hole injection layer. In one embodiment, the hole injection layer comprises a polymer. In one embodiment, the hole injection layer comprises a conjugated polymer. In one embodiment, the hole injection layer comprises a polythiophene. In one embodiment, the hole injection layer comprises a polythiophene comprising at least one alkoxy substituent. In one embodiment, the hole injection layer comprises a sulfonated polythiophene. In one embodiment, the hole injection layer comprises a polymeric arylamine. In one embodiment, the hole injection layer comprises a regioregular polythiophene. In one embodiment, the hole injection layer comprises a conjugated polymer which is soluble in water. In one embodiment, the hole injection layer comprises a conjugated polymer which is soluble in organic solvent.

In one embodiment, the method is further comprising the step of coating an emitting layer on the coated substrate.

In one embodiment, the ink comprises at least two hole transport materials comprising intractability groups. In one embodiment, the ink comprises at least two hole transport materials each comprising a different intractability group.

In one embodiment, the ink comprises a composition according to any of the hole transport compounds described herein. In one embodiment, the ink comprises a composition comprising at least two hole transport compounds as described herein.

In one embodiment, the compound is a first compound, and the composition further comprises at least one additional second compound, different from the first compound, which activates a polymerization reaction for the composition. In one embodiment, the compound is a first compound, and the composition further comprises at least one additional second compound, different from the first compound, which comprises para-styrene units. In one embodiment, the compound is a first compound, and the composition further comprises at least one additional second arylamine compound, different from the first arylamine compound, wherein the second arylamine compound has only one crosslinking group. In one embodiment, the compound is a first compound, and the composition further comprises at least one second arylamine compound, different from the first arylamine compound, wherein the second arylamine compound has three or more crosslinking groups. In one embodiment, the compound is a first compound, and the composition further comprises at least one second arylamine compound, wherein the second arylamine compound has a lower LUMO and lower or similar HOMO compared to the first and compound.

In one embodiment, the intractability groups are polymerizable groups.

An advantage for at least one embodiment is to provide high quality HTL films on different HIL layers including HIL layers that are relatively difficult to coat with high quality films.

An advantage for at least one embodiment is to provide stable HTL films on different HIL layers.

An additional advantage for at least one embodiment is to provide OLED devices with good lifetime and efficiency.

An additional advantage for at least one embodiment is to enable better film formation for solution EML layers coated on top of the hole transport layer.

DETAILED DESCRIPTION

Introduction

Figure 1:
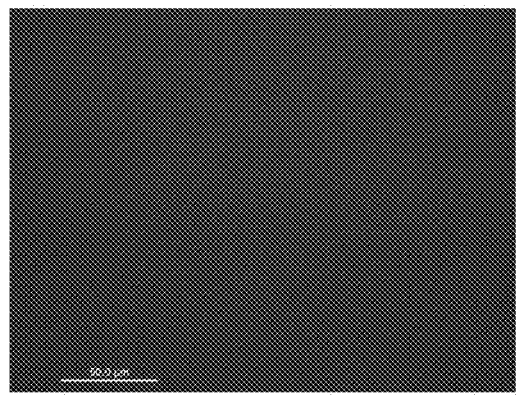
FIG. 1 illustrates one embodiment for an image on top of Plexcore® OC HIL (aqueous) 500× Magnification.

All references cited herein are incorporated by reference in their entirety.

Filed on the same day herewith is U.S. patent application Ser. No. 13/175,714, filed Jul. 1, 2011 entitled "HOLE TRANSPORT COMPOSITIONS AND RELATED DEVICES AND METHODS (II)" (assignee: Plextronics), which is hereby incorporated by reference in its entirety.

Organic electronics devices, including OLEDs, as well as materials to make organic electronic devices including hole injection layers and hole transport layers, are described in, for example, the following patent publications assigned to Plextronics, Inc.: WO 2006/036,755; WO 2006/086,480; WO 2008/073,149; WO 2009/126,918; WO 2009/111675; WO 2009/111339; WO 2010/051,259; WO 2010/059,240; WO 2010/059,646; and WO 2010/062,558. OLED devices can comprise a variety of sub-categories including, for example, PLEDs, SMOLEDs, PHOLEDs, WOLEDs, and the like. OLED devices, materials, and methods are also described in, for example, (1) *Highly Efficient OLEDS with Phosphorescent Materials* (Ed. H. Yerrin), 2008, Wiley-VCH, (2) *Organic Light Emitting Devices: Synthesis, Properties, and Applications* (Eds. Mullen, Scherf), 2006, (3) *Organic Light Emitting Methods and Devices*, (Li and Meng), 2007, CRC.

Electroluminescent devices are described in, for example, Friend et al., "Electroluminescence in Conjugated Polymers," *Nature,* 397, 121-128, Jan. 14, 1999. Hole injection and transport are described in, for example, Shen et al., "How to Make Ohmic Contact to Organic Semiconductors," *ChemPhysChem,* 2004, 5, 16-25. OLED devices are described in, for example, Forrest, "The Path to Ubiquitous and Low-Cost Organic Electronic Appliances on Plastic," *Nature,* 428, Apr. 29, 2004, 911-918.

Compounds and units within compounds which provide hole transport are known in the art. See, for example, U.S. Pat. Nos. 5,034,296; 5,055,366; 5,149,609; 5,589,320; 5,759,709; 5,895,692; and 7,125,633, as well as US Patent Publication Nos. 2005/0184287 and 2008/0286566. Hole transport materials, morphology, and devices (including arylamine compounds) are also described extensively in "Charge Carrier Transporting Molecular Materials and their Applications in Devices," Shirota et al., *Chem. Rev.,* 2007, 107, 953-1010.

Part I

Description of Single Hole Transporting Compounds with a Variety of Core, Arylamine, and Intractability Groups Individual hole transport materials or compounds are described. In addition, mixtures of two or more hole transport materials are also described.

Hole transport materials and compounds are known in the art. They typically comprise pi-electron systems. A leading example of a hole transport material is the arylamine set of compounds.

One embodiment provides, for example, a composition comprising: at least one compound comprising a hole transporting core, wherein the core is covalently bonded to a first arylamine group and also covalently bonded to a second arylamine group, and wherein the compound is covalently bonded to at least one intractability group, wherein the intractability group is covalently bonded to the hole transporting core, the first arylamine group, the second arylamine group, or a combination thereof, and wherein the compound has a molecular weight of about 5,000 g/mole or less.

The hole transporting core, arylamine, and intractability groups are describe more below.

Hole Transporting Core

The hole transporting core can be a bivalent, trivalent, or higher valent group which links at least to a first and a second arylamine group. This compound arrangement can be also represented by A1-C-A2, wherein A1 represents a first arylamine group, and A2 represents a second arylamine group, and C represents the hole transporting core. The one or more intractability groups can be bonded to one or more of A1, C, and/or A2. In addition, the compound can comprise additional arylamine groups either in the hole transporting core or in the groups linked to the arylamine groups outside of the core.

A variety of aryl or heteroaryl groups can be used in the hole transporting core. Examples of aryl and heteroaryl groups, which can be optionally substituted, are known in the art and include benzene, naphthalene, anthracene, phenanthrene, perylene, tetracene, pyrene, benzpyrene, chrysene, triphenylene, acenaphtene, fluorene, and those derived therefrom. Examples of heteroaryls include furan, benzofuran, thiophene, benzothiophene, pyrrole, pyrazole, triazole, imidazole, oxadiazole, oxazole, thiazole, tetrazole, indole, cabazole, pyrroloimidazole, pyrrolopyrazole, pyrrolopyrole, thienopyrrole, thienothiophene, furopyrrole, furofuran, thienofuran, benzoisoxazole, benzoisothiazole, benzoimidazole, pyridine, pyrazine, pyridazine, pyrimidine, triazine, quinoline, isoquinoline, cinnnoline, quinoxaline, phenanthridine, benzoimidazole, perimidine, quinazoline, quinazolinone, azulene, and those derived therefrom. The aryl or heteroaryl groups can comprise fused ring systems.

Aryl and heteroaryl groups can be optionally substituted with a variety of substituents and/or solubilizing groups. Examples can be (independently) H, F, alkyl, aryl, alkoxy, aryloxy, fluoroalkyl, fluoroaryl, fluoroalkoxy, fluoroaryloxy, as well as intractability groups described herein. Substituents on neighboring rings can fuse together to form a ring.

In one embodiment, for example, the hole transporting core comprises at least two aryl or heteroaryl rings. In one embodiment, the hole transporting core comprises at least three aryl or heteroaryl rings. In one embodiment, the hole transport core comprises only carbocyclic rings. In one embodiment, the hole transport core comprises at least one spiro moiety. Spiro moieties in a hole transport compounds are described in, for example, US Pat. Pub. No. 2004/0106004 (Li).

The hole transporting core can comprise all carbon and hydrogen atoms. Alternatively, the hole transporting core can comprise heteroatoms such as O, S, N, P, Si, Se, Te, and the like. In one embodiment, the hole transport core comprises at least one thiophene moiety. In one embodiment, the hole transport core comprises at least two thiophene moieties. In one embodiment, the hole transport core comprises at least one benzodithiophene moiety. In one embodiment, the hole transporting core comprises both O and S heteroatoms, as described further hereinbelow.

In one embodiment, the hole transport core comprises at least one heteroarylmoiety comprising at least one nitrogen. In one embodiment, the hole transport core comprises at least one heteroarylmoiety comprising at least two nitrogens. In one embodiment, the hole transport core comprises at least one piperazine moiety. In one embodiment, the hole transport core comprises at least one pyrrole ring. In one embodiment, the hole transport core comprises at least two pyrrole rings.

In one embodiment, the hole transport core comprises at least one silole ring. In one embodiment, the hole transport core comprises at least two silole rings.

The hole transporting core can comprise fused rings. In one embodiment, the hole transport core comprises at least two, or at least three, or at least four fused rings. In one embodiment, the hole transport core comprises at least five fused rings.

One or more substituent groups can be covalently bonded to the hole transporting core to increase solubility. A common example of such a solubilizing group is an optionally substituted alkyl or heteroalkyl moiety (an alkyl group, if used in a bivalent situation as spacer, can be also called alkylene; for example, propyl can be a propylene spacer). For example, C4 to C30, or C4 to C20, or C4 to C12 solubilizing groups can be used. Heteroatoms include, for example, oxygen, nitrogen, and sulfur. One skilled in the art can examine the impact of the substituent group on solubility. In one embodiment, the hole transport core is functionalized with at least one solubilizing group. In one embodiment, the hole transport core is functionalized with at least two solubilizing groups. In one embodiment, the hole transport core is functionalized with at least one solubilizing group which has a least four carbon atoms. In one embodiment, the hole transport core is functionalized with at least one solubilizing group which as an alkylene group comprising at least four carbon atoms. Other solubilizing groups are shown in the structures herein.

A variety of hole transporting cores are shown throughout the present disclosure including compounds based on combinations of substructures shown in Table 1 (below) and the working examples. Particular examples of hole transporting core groups comprising sulfur (along with representative arylamine groups, but without intractability groups except for as shown) are shown below, and show the hole transporting core covalently bonded to two arylamine groups:

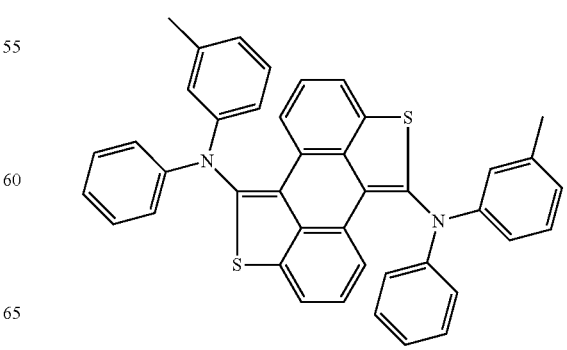

Compound/Core A-1 (no intractability groups shown)

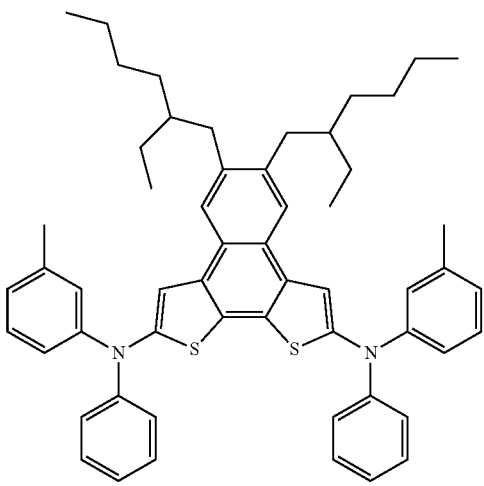 [SMILES: CCCCC(CC)Cc1cc2c(cc1CC(CC)CCCC)c1cc(N(c3ccccc3)c3cccc(C)c3)sc1c1sc(N(c3ccccc3)c3cccc(C)c3)cc21]

Compound/Core B-1 (no intractability groups shown). The branched alkyl solubilizing groups on the core can be varied including for example C4-C20 optionally substituted groups including alkyl groups.

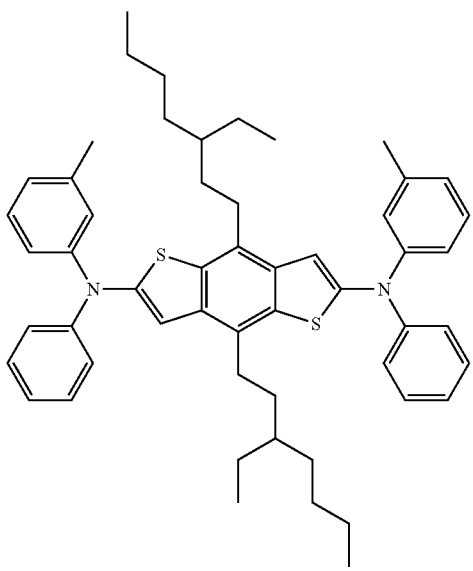 [SMILES: CCCCC(CC)CCc1c2cc(N(c3ccccc3)c3cccc(C)c3)sc2c(CCC(CC)CCCC)c2cc(N(c3ccccc3)c3cccc(C)c3)sc12]

Compound/Core C-1 (no intractability groups shown). The branched alkyl solubilizing groups on the core can be varied including for example C4-C20 optionally substituted groups including alkyl groups.

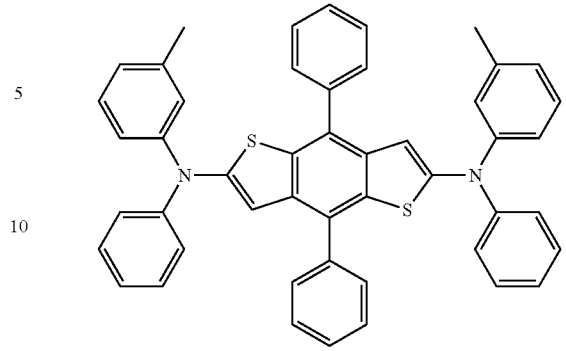

Compound/Core D-1 (no intractability groups shown).

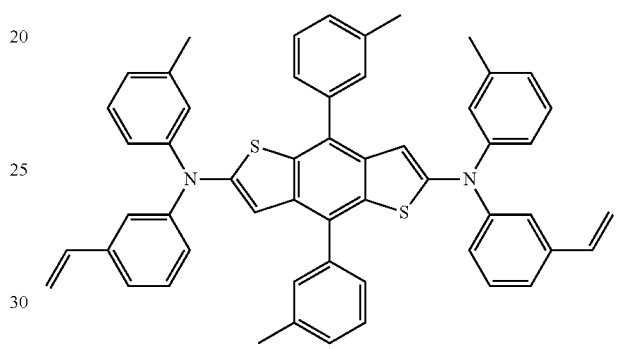

Compound/Core E-1, wherein two intractability groups are shown.

First and Second Arylamine Groups

Arylamine groups are generally known in the art. See, for example, US Pat. Pub. No. 2011/0017988 Yasukawa et. Al and other references cited herein. The arylamine group will have one valency on the nitrogen bonded to the hole transport core. The other two valencies on the nitrogen are bonded to aryl groups. This can be represented by N(R1)(R2)(R3), wherein R1-R3 are aryl groups which can be the same or different, independently of each other. The aryl-group can be a group free of heteroatoms or can be a heteroaryl group comprising at least one heteroatom. A variety of arylamine groups are shown throughout this disclosure including Table 1.

In one embodiment, the first and second arylamine groups are the same arylamine group. In one embodiment, the first and second arylamine groups are different arylamine groups.

In one embodiment, each of the first and second arylamine groups are independently represented by —N(R1)(R2), wherein R1 and R2 are optionally substituted aryl or heteroaryl groups which may be the same or different.

In one embodiment, each of the first and second arylamine groups are independently represented by —N(R1)(R2), wherein at least one of R1 and R2 is an optionally substituted phenyl group (the remaining valency on the arylamine is linked to the hole transporting core).

In one embodiment, each of the first and second arylamine groups are independently represented by —N(R1)(R2), wherein at least one of R1 and R2 is an optionally substituted biphenyl group.

In one embodiment, each of the first and second arylamine groups are independently represented by —N(R1)(R2), wherein at least one of R1 and R2 is an optionally substituted carbazole group.

In one embodiment, each of the first and second arylamine groups are independently represented by —N(R1)(R2), wherein —N(R1)(R2) form an optionally substituted carbazole group.

In one embodiment, each of the first and second arylamine groups are independently represented by —N(R1)(R2), wherein at least one of R1 and R2 is an optionally substituted naphthyl group.

In one embodiment, each of the first and second arylamine groups are independently represented by —N(R1)(R2), wherein at least one of R1 and R2 is an optionally substituted thienobenzene group.

In one embodiment, each of the first and second arylamine groups are independently represented by —N(R1)(R2), wherein at least one of R1 and R2 is an optionally substituted fluorene group.

In one embodiment, each of the first and second arylamine groups are independently represented by —N(R1)(R2), wherein at least one of R1 and R2 is an optionally substituted group comprising at least two fused aromatic rings.

Intractability, Polymerizable, and Crosslinking Groups

Intractability of hole transport materials is known in the art. See, for example, US Pat. Pub. Nos. 2009/0256117; 2010/0273007; and 2010/0292399. Intractability groups allow the materials to be sufficiently chemical and solvent resistant, allowing for solution processing.

In one embodiment, the intractability group comprises a polymerizable or crosslinking group. The crosslinking group allows for a covalent linkage between molecules and buildup of molecular weight to provide intractable, chemically resistant, and solvent resistant materials. In one embodiment, the intractability group comprises a non-crosslinking group. A non-crosslinking group can be a salt group, comprising cation and anion. Organic anions can be used including borates. Ammonium cations can be used.

In one embodiment, the intractability group can be linked to the rest of the molecule via a spacer. Examples of spacers include solubilizing groups, described herein, including alkylene groups. In one embodiment, the intractability group is a vinyl group, but is either linked to a non-aromatic group or is only linked to a single aromatic group as in a styrene conformation. In one embodiment, the intractability group is separated from a larger delocalized structure such as fused aromatic ring systems. This may, in some cases, improve stability. In one embodiment, the styrene group can be linked to the hole transporting core via a non-conjugated spacer such as an alkylene moiety.

In one embodiment, the intractability group comprises at least one ethylenically unsaturated moiety. In one embodiment, the intractability group comprises a vinyl group. In one embodiment, the vinyl group is linked to an oxygen atom (vinyleneoxy group) or in another embodiment to a carbon atom which is part of an aliphatic or aromatic group (e.g., propenyl; other examples include acryloyl, or methacryloyl). In one embodiment, the intractability group comprises a benzocyclobutane group. In one embodiment, the intractability group comprises an indene group (or indenyl, e.g., intractability group 4 in Table 1).

In one embodiment for a non-crosslinking group, the intractability group comprises a quaternary ammonium group. In one embodiment, the intractability group comprises a quaternary ammonium group comprising a tetraarylborate anion. In one embodiment, the intractability group comprises a quaternary ammonium group comprising a pentafluorophenylborate anion. A spacer group can be used to provide linkage between the quaternary ammonium group and the arylamine group. Several particular embodiments for compounds with intractability groups, which are not polymerizable groups, include compounds PLX-IG1 and PLX-IG2:

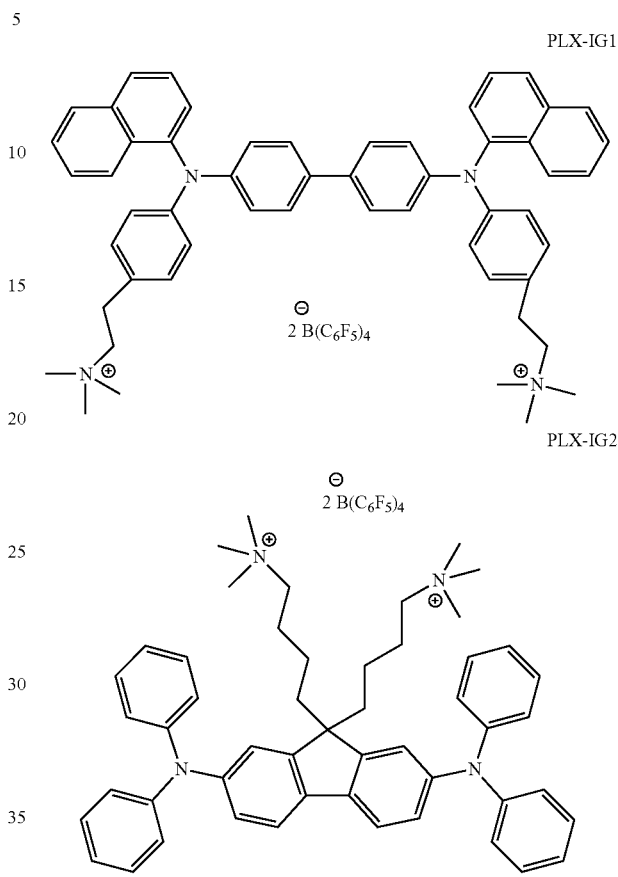

Arrangement of the Intractability Groups

At least three arrangement exist for arranging the intractability groups in the molecule with respect to the core and the arylamine groups, and representative embodiments for each are described herein.

In one first embodiment, for example, the compound comprises at least three intractability groups, and at least one intractability group is covalently bonded to the hole transport core, and at least one intractability group is covalently bonded to the first arylamine group, and at least one intractability group is covalently bonded to the second arylamine group.

In one second embodiment, for example, the intractability group is, or the intractability groups are, covalently bonded to the hole transport core but not the first arylamine group or the second arylamine group.

In one third embodiment, for example, the intractability group is, or the intractability groups are, covalently bonded to the first arylamine group, the second arylamine group, or both, but is not bonded to the hole transport core.

Number of Intractability Groups

In one embodiment, the compound comprises one intractability group. In one embodiment, the compound comprises two or more intractability groups. In other embodiments, the compound comprises three, four, five, or six or more intractability groups.

No particular upper limit exists, but the number of intractability groups can be 12 or less, or 10 or less, or 8 or less, or 6 or less.

19

Molecular Weight

In addition, the molecular weight (g/mol) for the hole transport compound can be adapted for an application. The molecular weight can be, for example, about 5,000 g/mol or less, or about 4,000 g/mol or less, or about 3,000 g/mol or less, or about 2,000 g/mol or less, or about 1,000 g/mol or less. In one embodiment, the compound's molecular weight is about 400 g/mol to about 5,000 g/mol, or about 400 g/mol to about 2,000 g/mol. In one embodiment, the compound's molecular weight is about 2,000 g/mol to about 5,000 g/mol. The molecular weight can be greater than, for example, about 250 g/mol, or greater than about 400 g/mol.

Table with Examples of HTL Core, Arylamine, and Intractability Groups

The following Table 1 provides specific examples of hole transporting core groups, the arylamine groups (whether first or second arylamine groups), and intractability groups. These can be arranged in any combination which is synthetically viable. For the HTL core groups shown in Table 1, the dangling bonds represent bonding sites for the arylamine group at the nitrogen atom. The R or R' groups shown in Table 1 can be, independently of each other, substituent or solubilizing groups as described herein including, for example, C1-C20 groups, or C4-C20 groups. The R or R' groups can be saturated or unsaturated, linear, cyclic, branched, and optionally substituted with functional groups known in the art.

TABLE 1

| | HTL Core Group | Arylamine Groups | Intractability Groups (IG) |
|---|---|---|---|
| 1 | 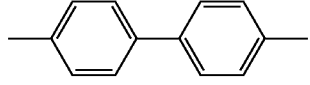 | 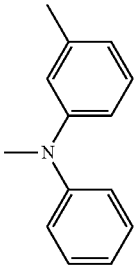 |  |
| 2 | 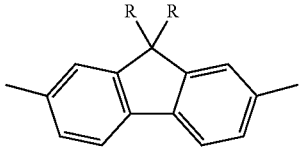 | 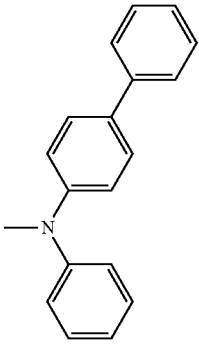 [SMILES: CN(c1ccccc1)c1ccc(-c2ccccc2)cc1] | 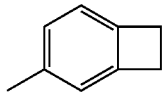 |
| 3 | 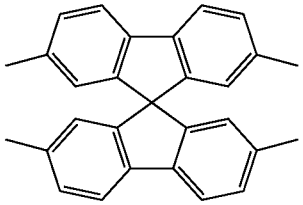 | 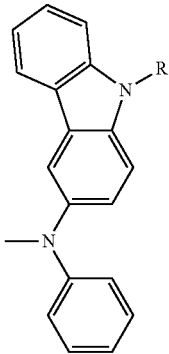 | 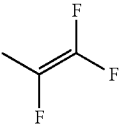 |

TABLE 1-continued
| | HTL Core Group | Arylamine Groups | Intractability Groups (IG) |
|---|---|---|---|
| 4 | 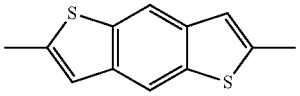 | 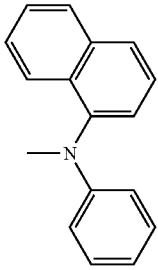 [SMILES: CN(c1ccccc1)c1cccc2ccccc12] | 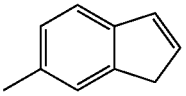 |
| 5 | 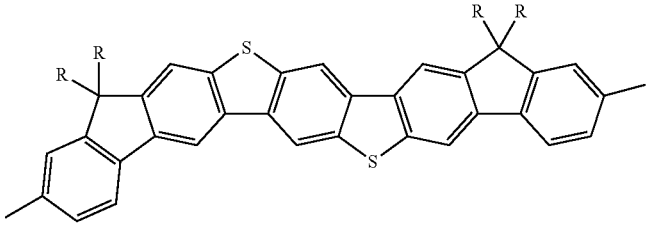 | 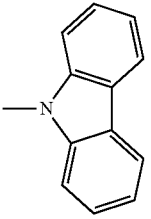 | 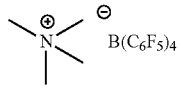 B(C₆F₅)₄ |
| 6 | 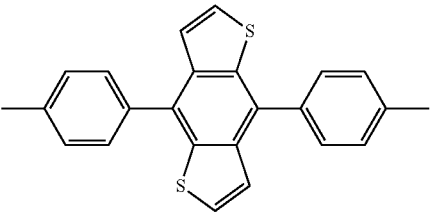 | 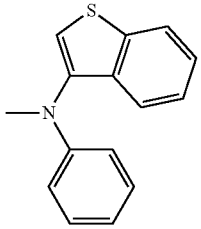 [SMILES: CN(c1ccccc1)c1csc2ccccc12] | |
| 7 | 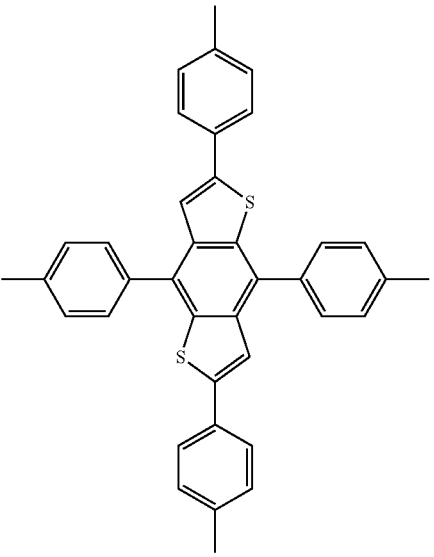 | 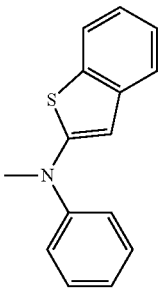 [SMILES: CN(c1ccccc1)c1cc2ccccc2s1] | |

TABLE 1-continued

| | HTL Core Group | Arylamine Groups | Intractability Groups (IG) |
|---|---|---|---|
| 8 | | | |
| 9 | | | |
| 10 | | | |
| 11 | | | |
| 12 | | | |

TABLE 1-continued
| | HTL Core Group | Arylamine Groups | Intractability Groups (IG) |
|---|---|---|---|
| 13 | 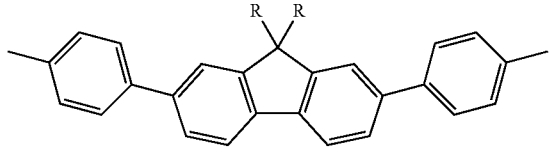 | 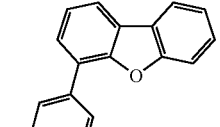 | |
| 14 | 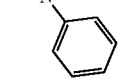 | 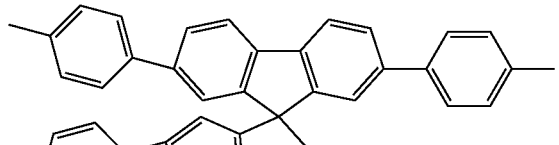 | |
| 15 | 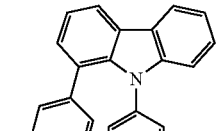 | 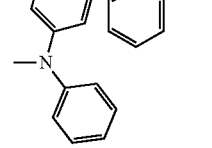 | |
| 16 | 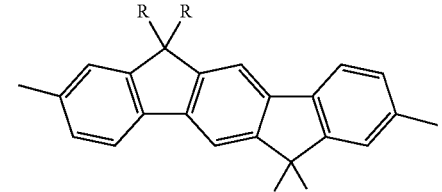 | | |
| 17 | 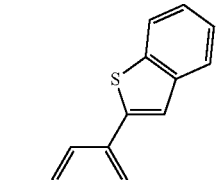 | | |
| 18 | 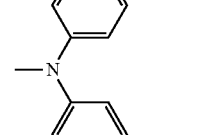 | | |

TABLE 1-continued

| | HTL Core Group | Arylamine Groups | Intractability Groups (IG) |
|---|---|---|---|
| 19 | | | |
| 20 | | | |
| 21 | | | |
| 22 | | | |
| 23 | | | |
| 24 | | | |

TABLE 1-continued
| | HTL Core Group | Arylamine Groups | Intractability Groups (IG) |
|---|---|---|---|
| 25 | 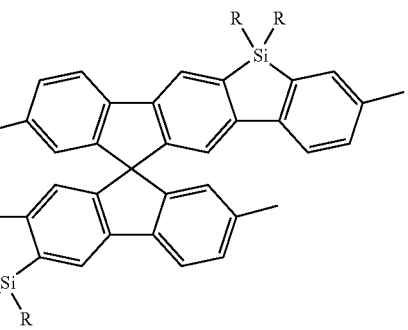 | | |
| 26 | 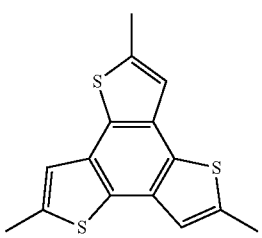 | | |
| 27 | 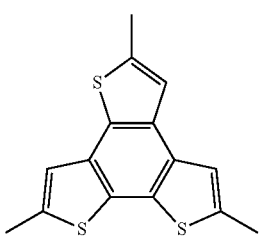 | | |
| 28 | 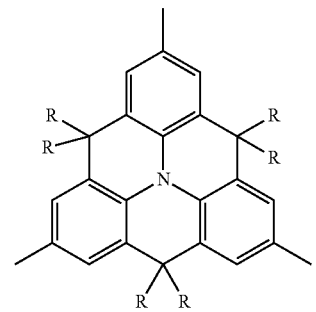 | | |
| 29 | 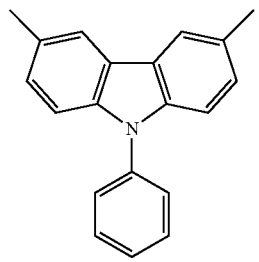 | | |

TABLE 1-continued
| | HTL Core Group | Arylamine Groups | Intractability Groups (IG) |
|---|---|---|---|
| 30 | 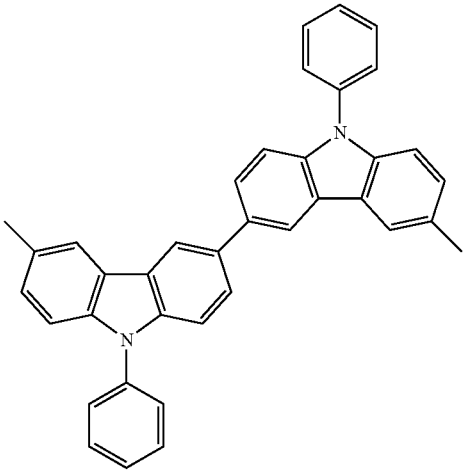 | | |
| 31 | 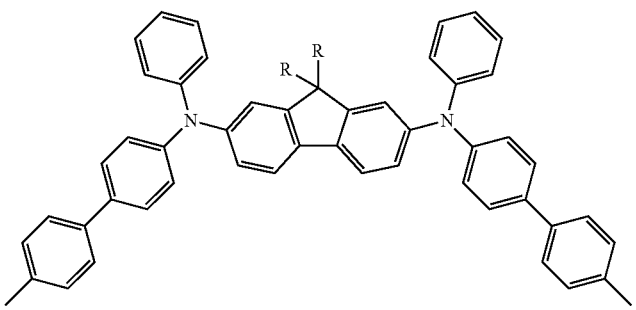 | | |
Additional Specific Compounds
Additional specific hole transporting compounds are shown below (note that the $C_6H_{13}$ groups are shown below as representative; they could be, for example, any R groups such as C4 to C20 alkyl groups including linear or branched or cyclic):
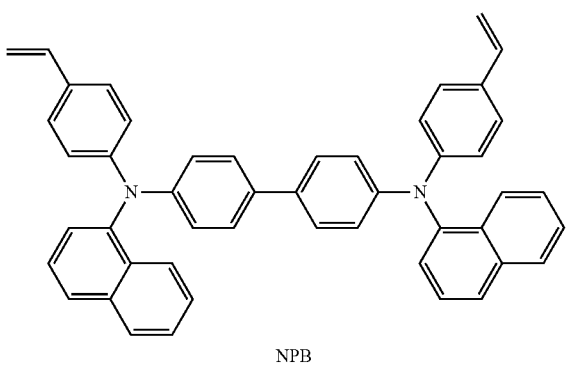
NPB
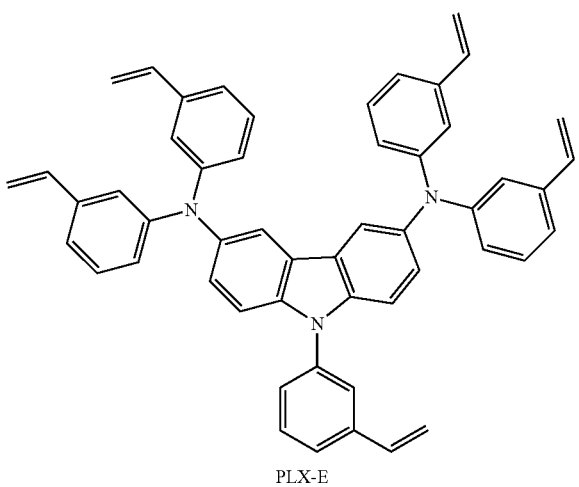
PLX-E -continued
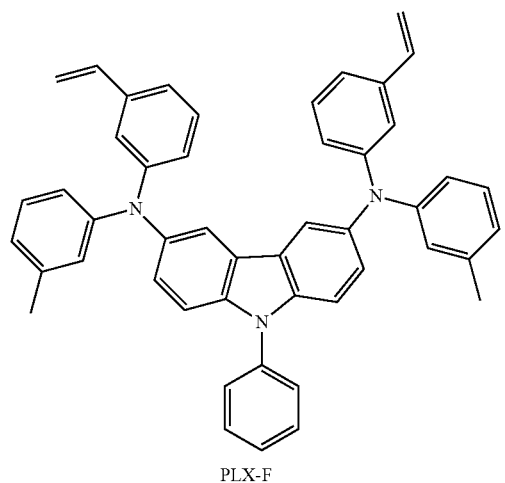
PLX-F
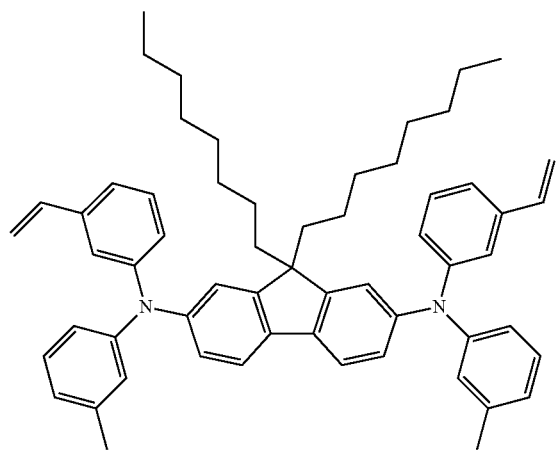
PLX-D
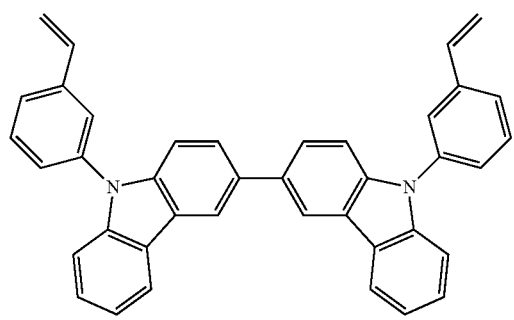
PLX-G
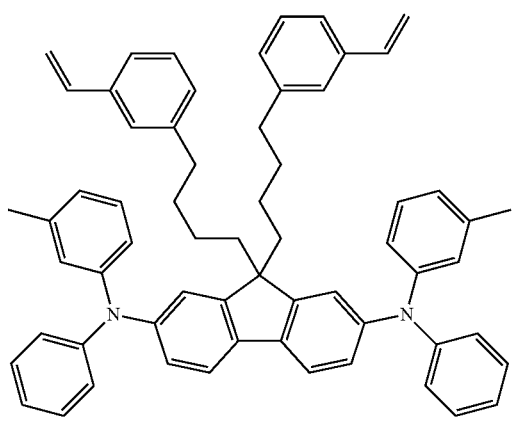
PLX-H
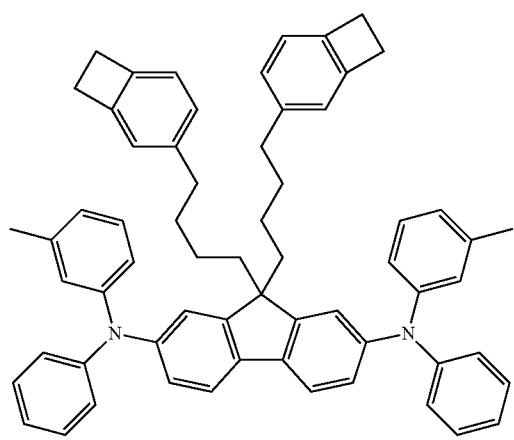
PLX-I -continued
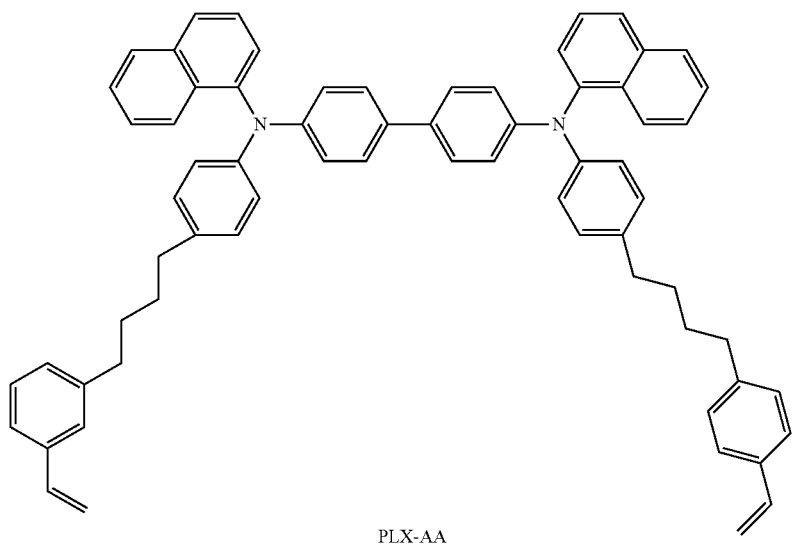
PLX-AA
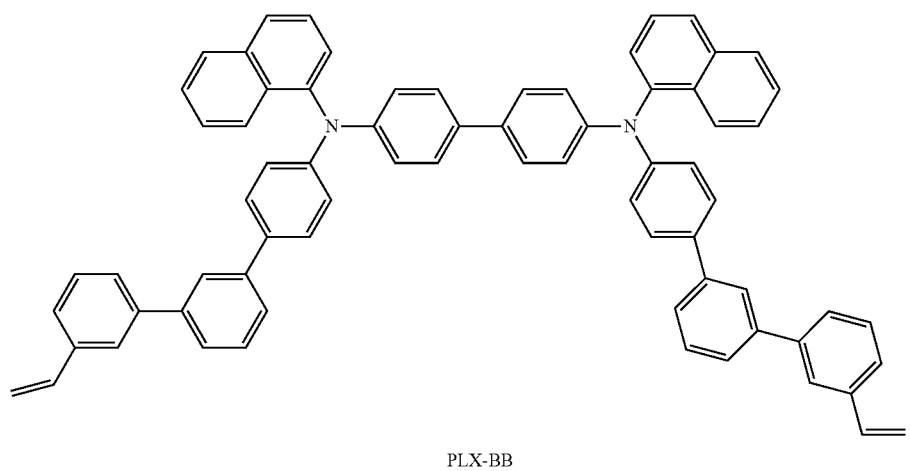
PLX-BB
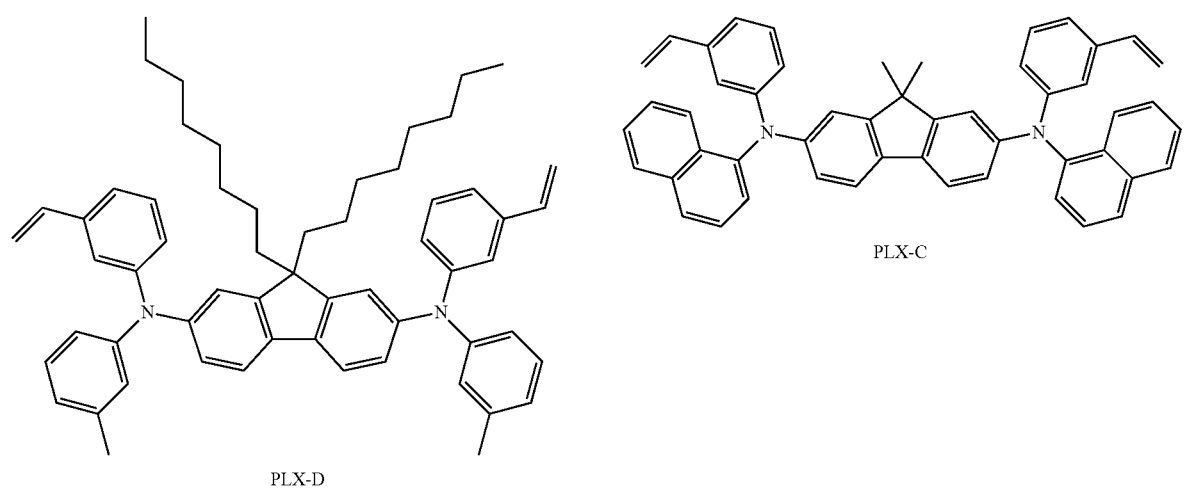
PLX-D
PLX-C -continued
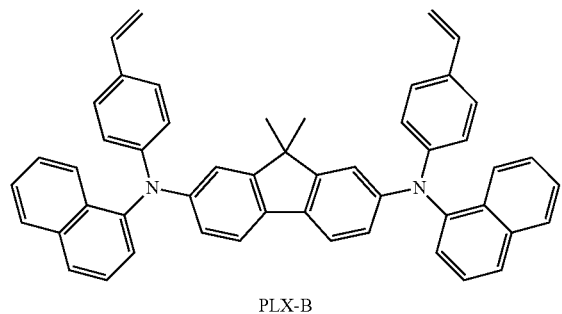
PLX-B
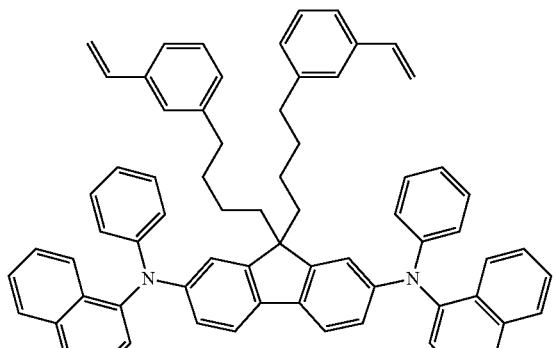
PLX-K
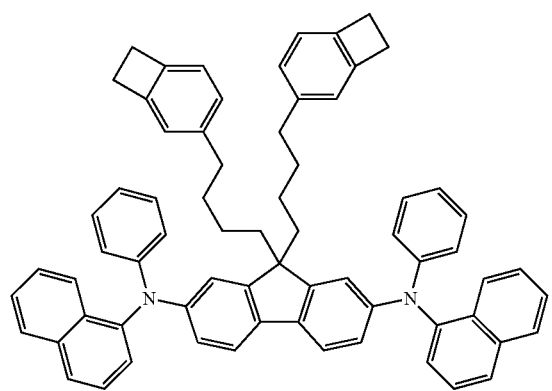
PLX-L
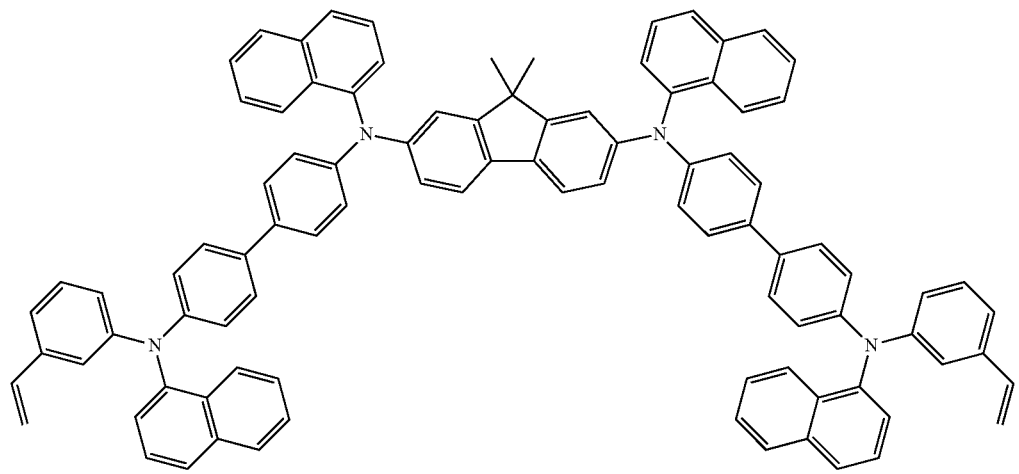
PLX-M -continued
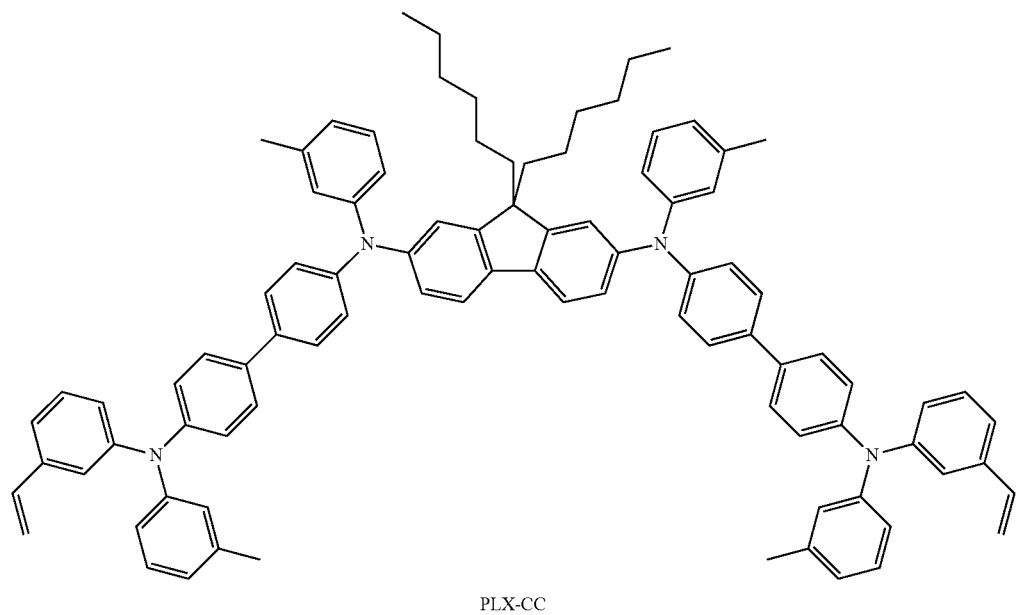
PLX-CC
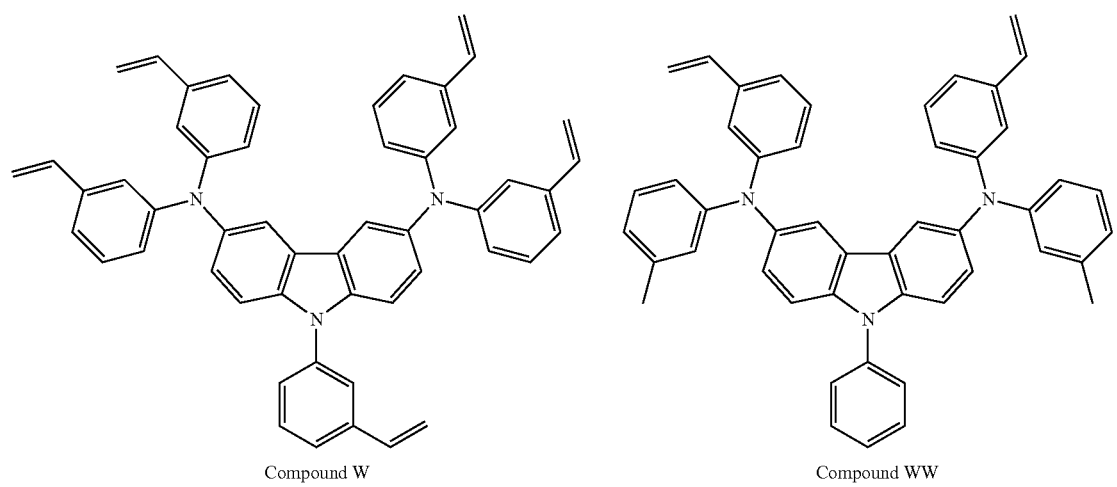
Compound W
Compound WW
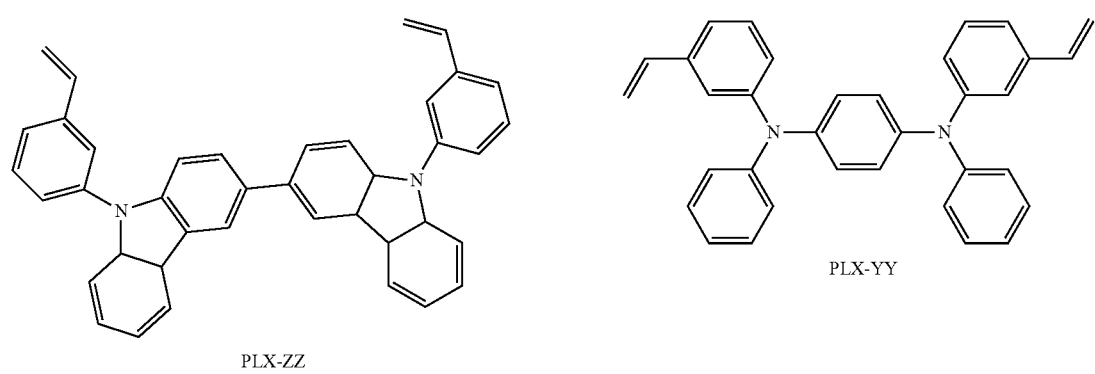
PLX-ZZ
PLX-YY -continued
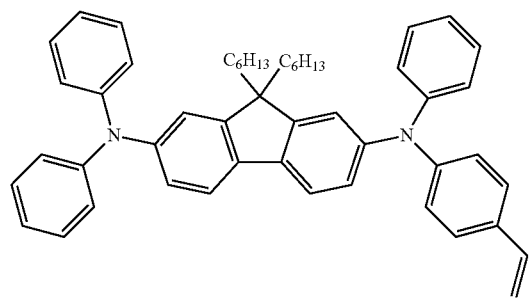
PLX-XX
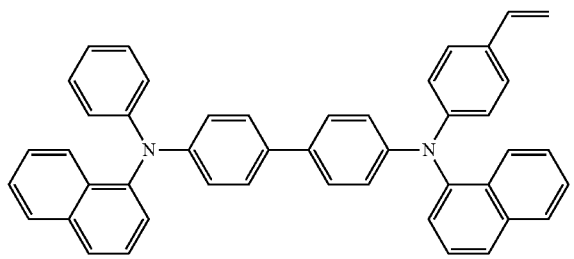
PLX-WW
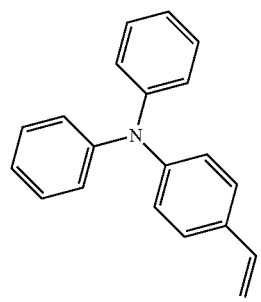
PLX-VV
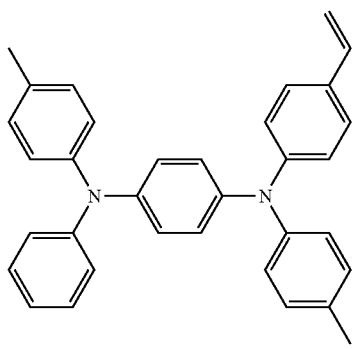
PLX-UU
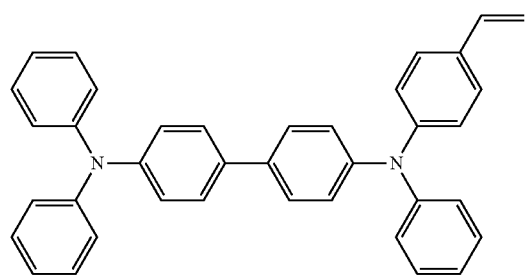
PLX-TT
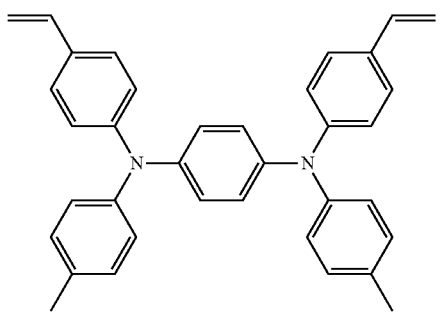
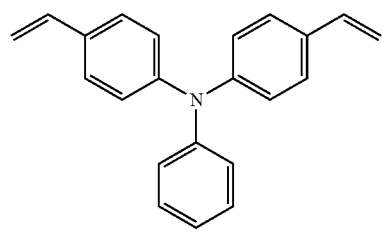
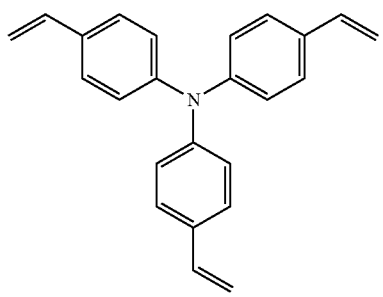
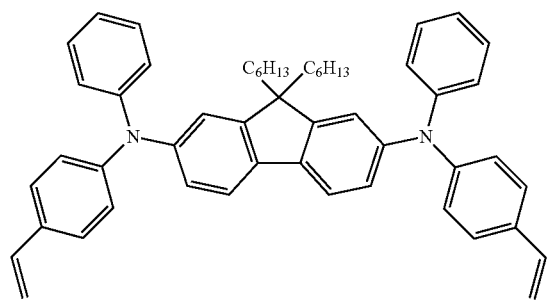
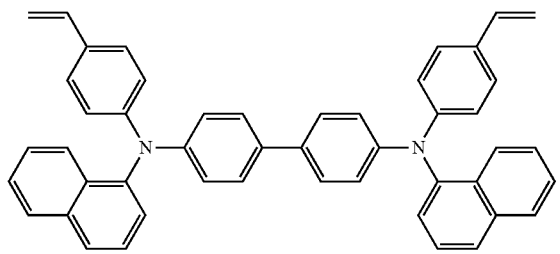

-continued
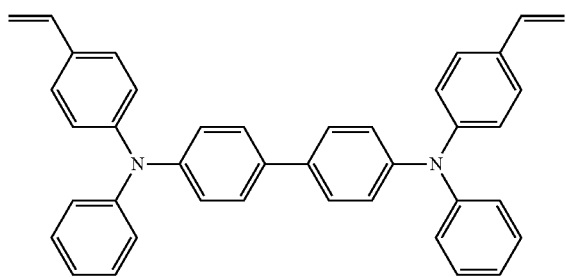
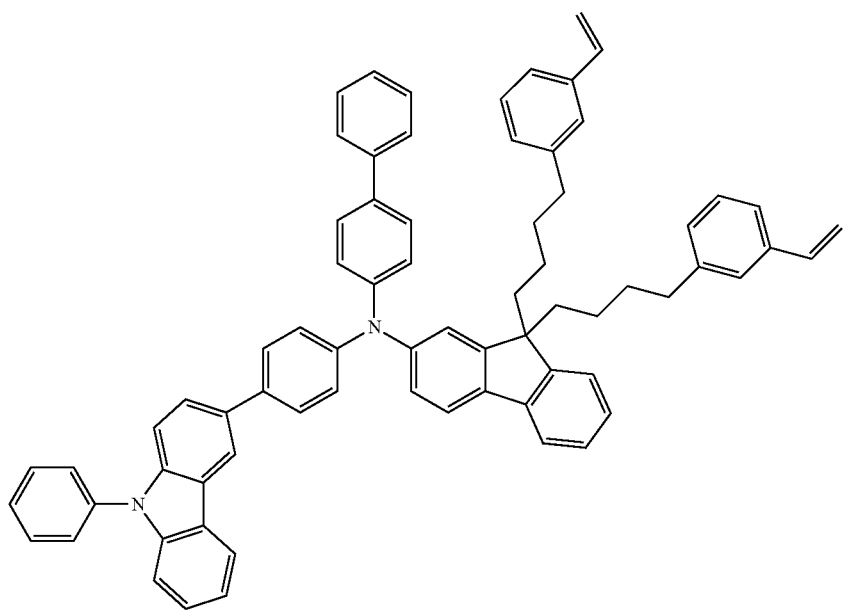
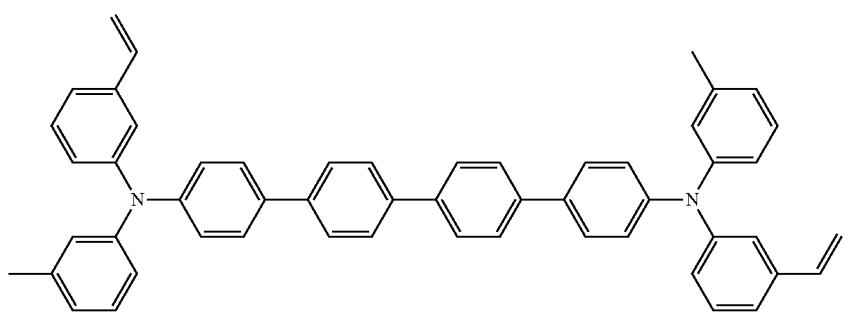
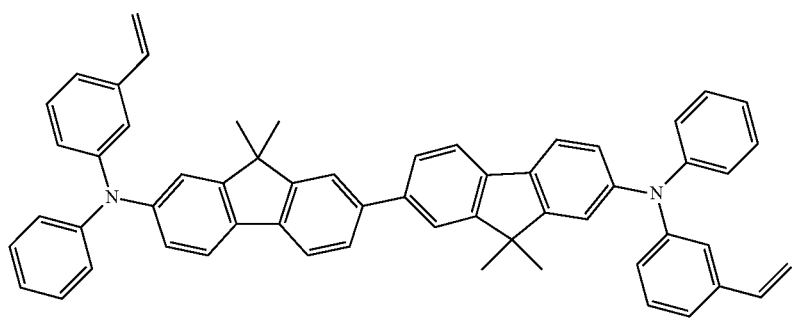

-continued

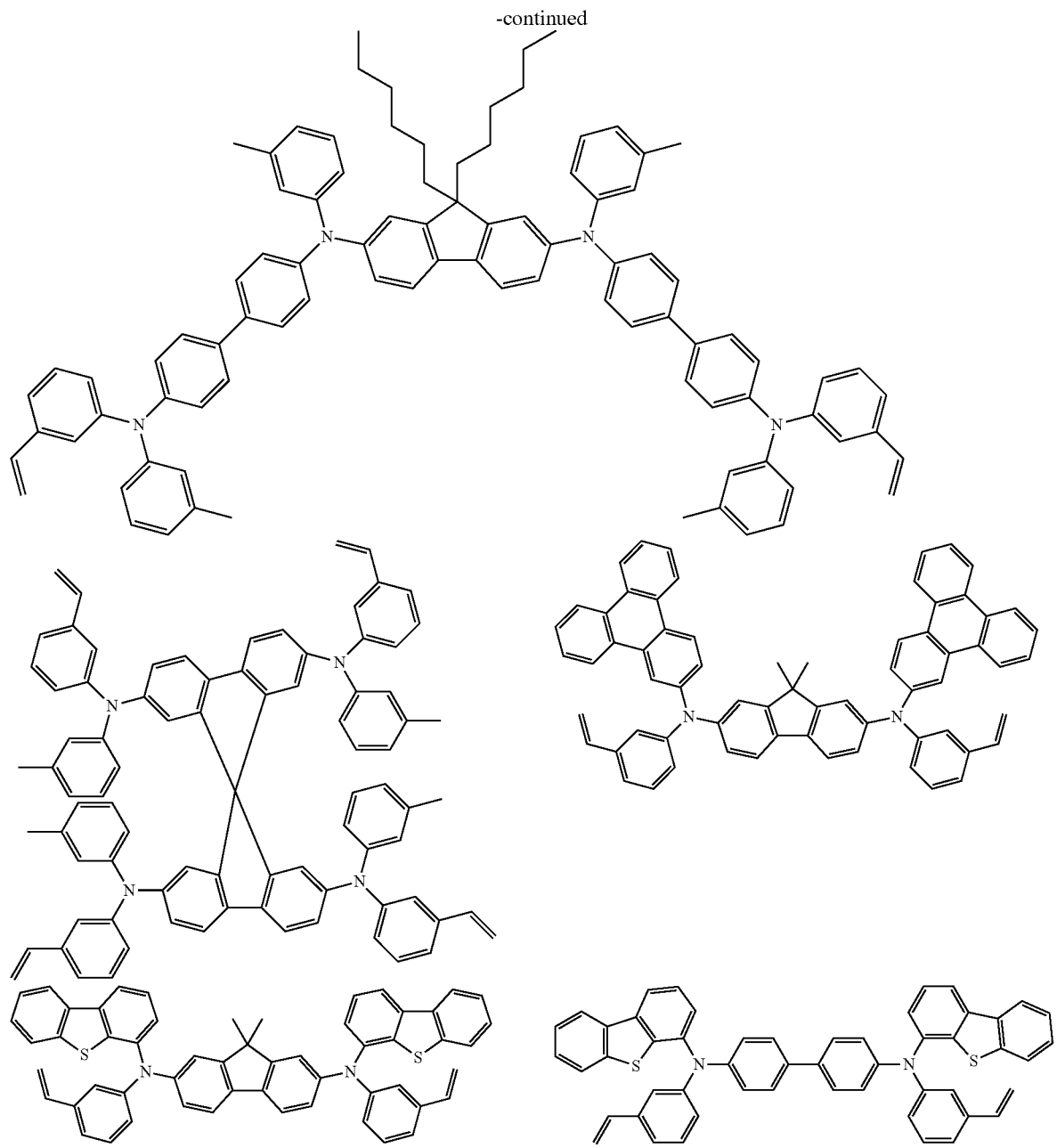

Part II
Mixtures of Hole Transporting Compounds

In Part II, compositions can be prepared which comprise two or more hole transporting compounds. Compounds as described above in Part I can be selected for use in mixtures including binary mixtures. In particular, however, for compounds in these mixtures, for example, the core can comprise, for example, fluorene, phenyl, or biphenyl moieties. In particular, the fluorene core is of interest for the mixtures. The careful formulation of the mixtures can provide for good coating of HIL layers including non-aqueous HIL layers.

For example, one embodiment provides a composition comprising: at least one first compound and at least one second compound different from the first, wherein the at least one first compound comprises a hole transporting core which is a fluorene core, wherein the hole transporting core is covalently bonded to a first arylamine group and also covalently bonded to a second arylamine group, and wherein the core is further covalently bonded to at least two solubilizing groups comprising at least four carbon atoms, and wherein the solubilizing groups are optionally substituted with intractability groups; wherein the at least one second compound comprises a hole transporting core which is a fluorene core, wherein the hole transporting core is covalently bonded to a first arylamine group and also covalently bonded to a second arylamine group, wherein the second compound further comprises at least one intractability group which may be bonded to the first arylamine group, the second arylamine group, or both; and wherein the first and second compounds have molecular weight of about 5,000 g/mole or less.

Relative Mass Proportion of First and Second Compounds

The relative mass proportion of the first and second compounds can be adapted for a particular application. For example, in one embodiment, the relative amounts of the first and second compounds are about 99:1 to about 1:99 by weight, respectively. In another embodiment, the relative amounts of the first and second compounds are about 90:10 to about 10:90 by weight, respectively. In another embodiment, the relative amounts of the first and second compounds are about 80:20 to about 20:80 by weight, respectively. In another embodiment, the relative amounts of the first and second compounds are about 70:30 to about 30:70 by weight, respectively. In another embodiment, the relative amounts of the first and second compounds are about 60:40 to about 40:60 by weight, respectively.

In one embodiment, the relative amounts of the first and second compounds are about 20:80 to about 40:60 by weight, respectively.

In one embodiment, the relative amounts of the first and second compounds are about 99:1 to about 80:20 by weight, respectively.

In one embodiment, the relative amounts of the first and second compounds are about 40:60 to about 60:40 by weight, respectively.

In one embodiment, the relative amounts of the first and second compounds are about 80:20 to about 60:40 by weight, respectively.

Symmetry of First and Second Arylamine Groups

In one embodiment, for the first compound, the first and send arylamine groups are the same group. In one embodiment, for the second compound, the first and send arylamine groups are the same group. In one embodiment, the first and second arylamine groups are different for the first and second compounds.

Molecular Weights

The molecular weight (g/mol) of the hole transporting compound used in mixtures can be adapted for a particular application and can be independently selected for each compound. For example, in one embodiment, the molecular weight of the first compound is about 5,000 or less, and the molecular weight of the second compound is about 5,000 or less. In another embodiment, the molecular weight of the first compound is about 3,000 or less, and the molecular weight of the second compound is about 3,000 or less. In one embodiment, the molecular weight of the first compound is about 2,000 or less, and the molecular weight of the second compound is about 2,000 or less. In one embodiment, the molecular weight of the first compound is about 1,000 or less, and the molecular weight of the second compound is about 1,000 or less. The molecular weight of the first and second compounds can be, for example, at least about 100, or at least about 200, or at least about 300, or at least about 400, or at least about 500.

Number of Arylamine Groups

In the mixtures, the hole transporting compounds can comprise first and second arylamine groups. In one embodiment, the first compound has only two arylamine groups, and the second compound has only two arylamine groups. In another embodiment, the first or second compound has three, four, five, or even six or more aryl amine groups. The core, which links the first and second arylamine groups, can comprise third, forth, fifth, and sixth or more arylamine groups.

Bonding Sites on the Core Fluorene

The hole transporting core can be based on a fluorene moiety, and the numbering scheme for fluorene substituents is known in the art. In one embodiment, the core fluorene groups of the first and second compounds are bonded to the arylamines at the 2 and 7 positions of the fluorene group, and the core fluorene group is bonded to the substituents or solubilizing groups at the 9 position.

In one embodiment, the two substituents or solubilizing groups bonded to the fluorene core are the same groups. In one embodiment, the two substituents or solubilizing groups bonded to the fluorene core are different groups. The two or more substituents or solubilizing groups can be selected independently of each other. They can be, for example, C4 to C20 groups.

Length of Substituents or Solubilizing Groups—First Compound

The length of the substituents or solubilizing groups can be adapted for a particular application. For example, for the first compound, the two substituents or solubilizing groups can comprise at least four carbon atoms, at least five carbon atoms, or at least six carbon atoms, or at least seven carbon atoms, or at least eight carbon atoms. The substitutent or solubilizing group can be, for example, a C4-C20 group including a straight chain, a branched group, or a cylic group. Examples include optionally substituted alkyl groups. Unsaturated groups can be present including double or triple bonds.

Distribution of the Intractability Groups on Arylamines—Second Compound

In one embodiment, the second compound comprises at least one intractability group which is bonded to the first arylamine group, and at least one intractability group which is bonded to the second arylamine group.

Types of Intractability Groups

In one embodiment, the intractable groups are crosslinking polymerizable groups. In another embodiment, the intractable groups are ethylenically unsaturated groups. They can be vinyl including vinyl bonded to phenyl creating a styrene unit, whether para or meta substituted.

Types of Intractability Groups—Second Compound

In one embodiment, the intractability group for the second compound is vinyl. In one embodiment, the intractability group for the second compound is vinyl which is covalently bonded to a phenyl ring to form a styrene unit.

Types of Groups Bonded to the Arylamine

In one embodiment, at least one of the arylamine groups comprises an optionally substituted naphthyl group bonded to nitrogen. In at least one embodiment, at least one of the arylamine groups comprises an both an optionally substituted naphthyl group and an optionally substituted phenyl group bonded to nitrogen.

Solubility of First and Second Compounds

In one embodiment, the solubility of the first compound can be at least 0.1 mg/mL, or at least 0.9 mg/mL, or at least or at least 2 mg/mL, as measured by dissolving the hole transport material in toluene or other suitable solvent at 25° C.

In one embodiment, the solubility of the first compound can be at least 0.1 mg/mL, or at least 0.9 mg/mL, or at least 2 mg/mL, as measured by dissolving the hole transport material in toluene or other suitable solvent at 25° C.

Embodiments Including PLX-A (Working Examples)

In one embodiment, for the first compound, the solubilizing group is substituted with the intractability group, and for the second compound the core further comprises at least two solubilizing groups comprising at least four carbon atoms.

In one embodiment, the relative amounts of the first and second compounds are about 20:80 to about 40:60 by weight, respectively.

In one embodiment, the relative amounts of the first and second compounds are about 25:75 to about 35:65 by weight, respectively.

In one embodiment, the first compound the intractability group is benzocyclobutane.

In one embodiment, for the second compound the core further comprises at least two solubilizing groups comprising at least eight carbon atoms.

In one embodiment, for the second compound, the solubilizing groups do not comprise intractability groups.

In one embodiment, the first compound and the second compound comprise different intractability groups.

In one embodiment, the first compound is represented by:

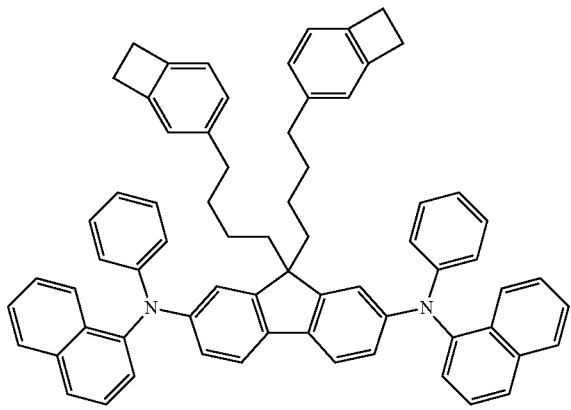 [SMILES: c1ccc(N(c2ccc3c(c2)C(CCCCc2ccc4c(c2)CC4)(CCCCc2ccc4c(c2)CC4)c2cc(N(c4ccccc4)c4cccc5ccccc45)ccc2-3)c2cccc3ccccc23)cc1]

In one embodiment, the first compound is represented by:

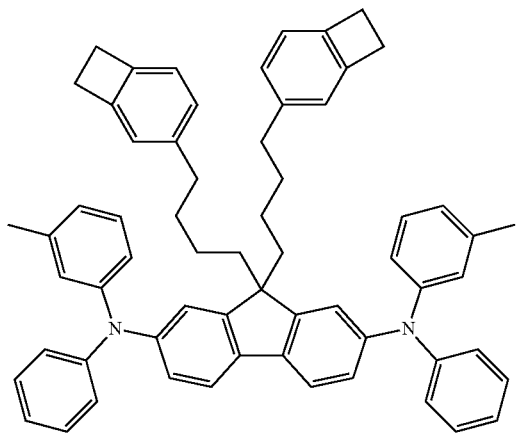

In one embodiment, the second compound is represented by:

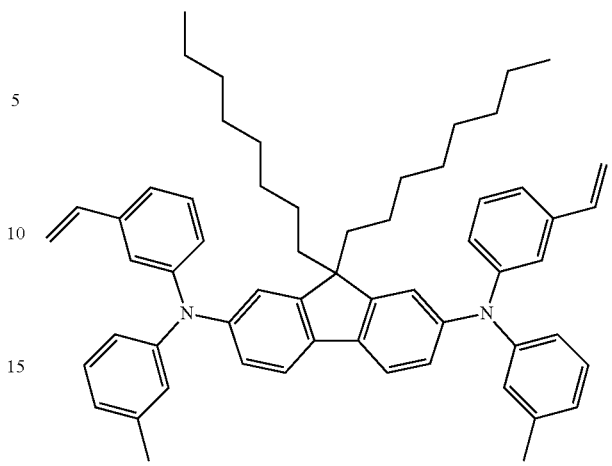

In one embodiment, the first compound is represented by:

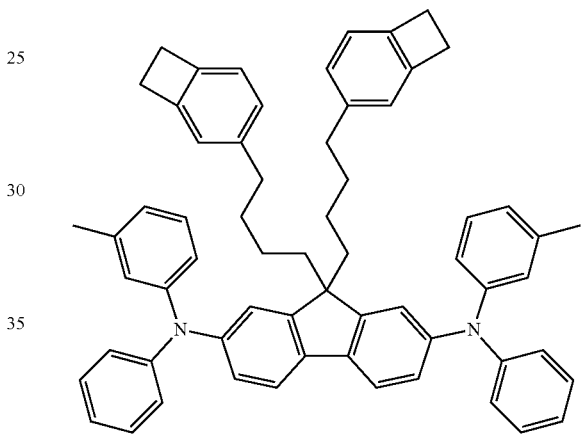

and the second compound is represented by:

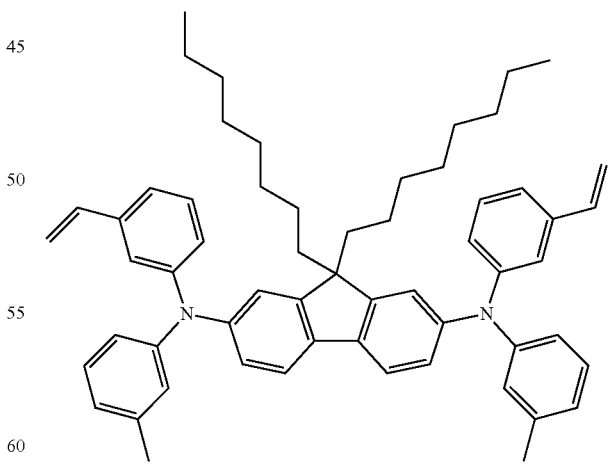

Embodiments Including Ink B (Working Examples)

In one embodiment, for the first compound, the solubilizing group of the core is unsubstituted with intractability group.

In one embodiment, the relative amounts of the first and second compounds are about 99:1 to about 80:20 by weight, respectively. In one embodiment, the relative amounts of the first and second compounds are about 95:5 to about 85:15 by weight, respectively.

In one embodiment, for the first compound the intractability group is on at least one of the arylamine groups and is vinyl.

In one embodiment, for the second compound the core further comprises to groups bonded to fluorene which are C3, C2, or C1 groups.

In one embodiment, for the second compound intractability groups bonded to the first and second arylamine which are vinyl bonded to phenyl to form a para-styrene.

In one embodiment, the first compound does not comprise intractability groups bonded to the core.

In one embodiment, the first compound is represented by:

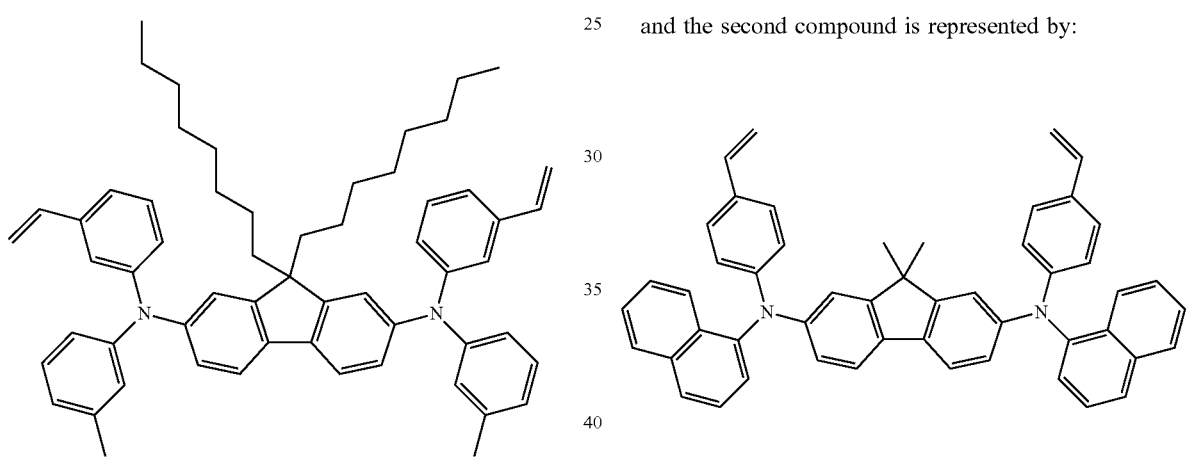

In one embodiment, the second compound is represented by:

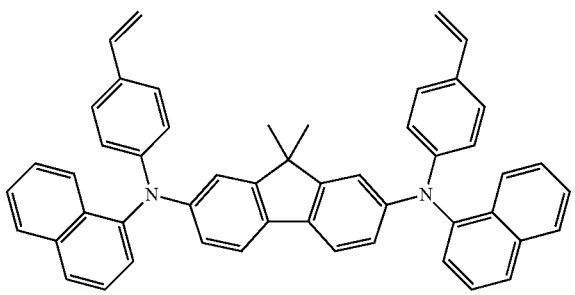 [SMILES: C=Cc1ccc(N(c2ccc3c(c2)C(C)(C)c2cc(N(c4ccc(C=C)cc4)c4cccc5ccccc45)ccc2-3)c2cccc3ccccc23)cc1]

In one embodiment, the first compound is represented by:

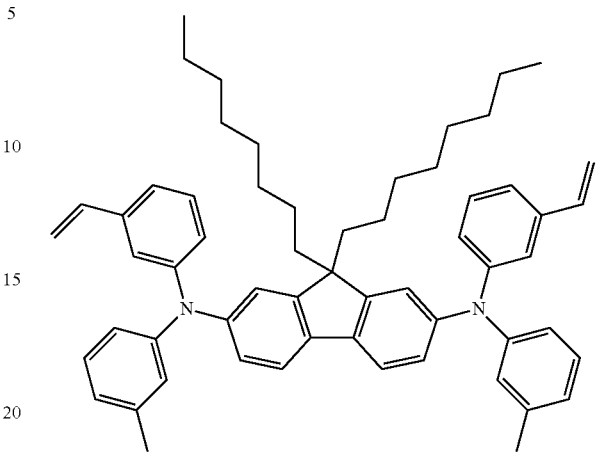

and the second compound is represented by:

Embodiments Including Ink C (Working Examples)

In one embodiment, for the first compound, the solubilizing group is substituted with the intractability group and for the second compound, the core does not comprise at least two solubilizing groups comprising at least four carbon atoms.

In one embodiment, the relative amounts of the first and second compounds are about 80:20 to about 20:80 by weight, respectively. In one embodiment, the relative amounts of the first and second compounds are about 60:40 to about 40:60 by weight, respectively.

In one embodiment, for the first compound the intractability group is vinyl. In one embodiment, for the first compound the intractability group is vinyl bonded to a phenyl to form a styrene unit.

In one embodiment, for the second compound the core further comprises to groups bonded to fluorene which are C3, C2, or C1 groups.

In one embodiment, for the second compound intractability groups bonded to the first and second arylamine which are vinyl bonded to phenyl to form a para-styrene.

In one embodiment, the first compound is represented by:

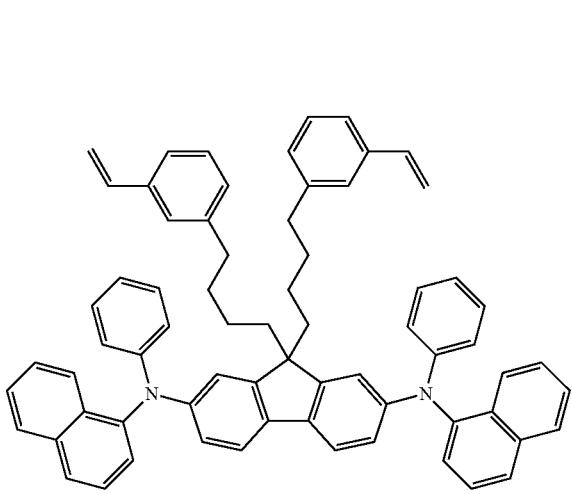 [SMILES: C=Cc1cccc(CCCCC2(CCCCc3cccc(C=C)c3)c3cc(N(c4ccccc4)c4cccc5ccccc45)ccc3-c3ccc(N(c4ccccc4)c4cccc5ccccc45)cc32)c1]

In one embodiment, the second compound is represented by:

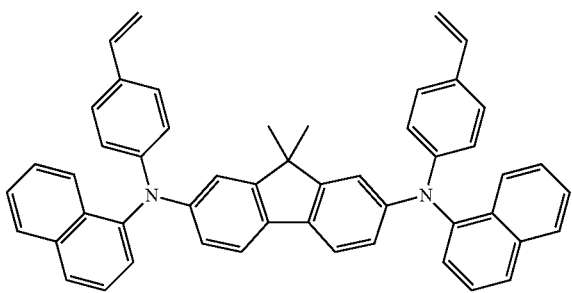 [SMILES: C=Cc1ccc(N(c2ccc3c(c2)C(C)(C)c2cc(N(c4ccc(C=C)cc4)c4cccc5ccccc45)ccc2-3)c2cccc3ccccc23)cc1]

lp;3pIn one embodiment, the first compound is represented by:

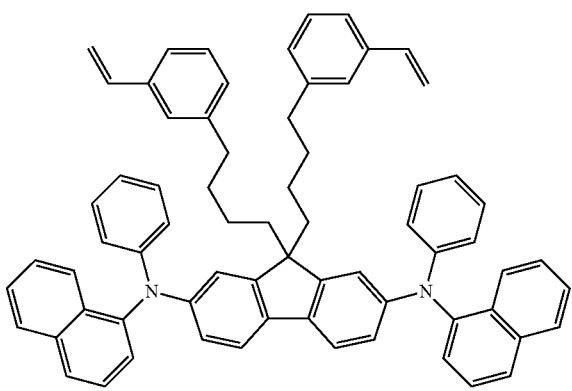 [SMILES: C=Cc1cccc(CCCCC2(CCCCc3cccc(C=C)c3)c3cc(N(c4ccccc4)c4cccc5ccccc45)ccc3-c3ccc(N(c4ccccc4)c4cccc5ccccc45)cc32)c1]

and the second compound is represented by:

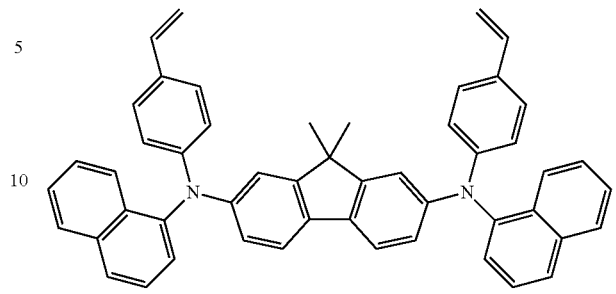

Polymerization Activators

The hole transporting formulations based on compounds of Parts I and II can be adapted with use of additional components such as polymerization activators.

In one embodiment, the compound of Part I is a first compound, and the composition further comprises at least one additional second compound, different from the first compound, which activates a polymerization reaction for the composition.

In one embodiment, the compound of Part I is a first compound, and the composition further comprises at least one additional second compound, different from the first compound, which comprises para-styrene units.

In one embodiment, the compound of Part I is a first compound, and the composition further comprises at least one additional second arylamine compound, different from the first arylamine compound, wherein the second arylamine compound has only one crosslinking group.

In one embodiment, the compound of Part I is a first compound, and the composition further comprises at least one second arylamine compound, different from the first arylamine compound, wherein the second arylamine compound has three or more crosslinking groups.

In one embodiment, the compound of Part I is a first compound, and the composition further comprises at least one second arylamine compound, wherein the second arylamine compound has a lower LUMO and lower or similar HOMO compared to the first and compound.

For example, in one embodiment for a binary blend, the composition further comprises at least one third compound, different from the first and second compounds, which activates a polymerization reaction for the composition.

In one embodiment for a binary blend, for example, the composition further comprises at least one third compound, different from the first and second compounds, which comprises para-styrene units.

Examples of activators or compounds having the vinyl group in a para position on the styrene moiety are shown below:

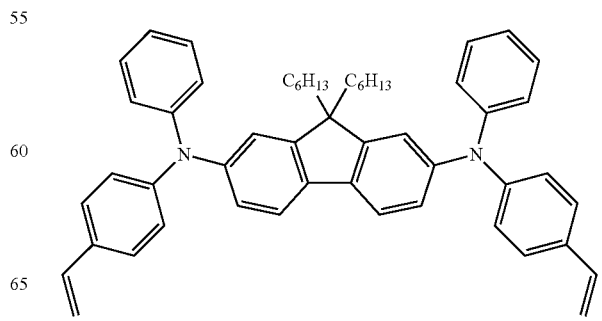

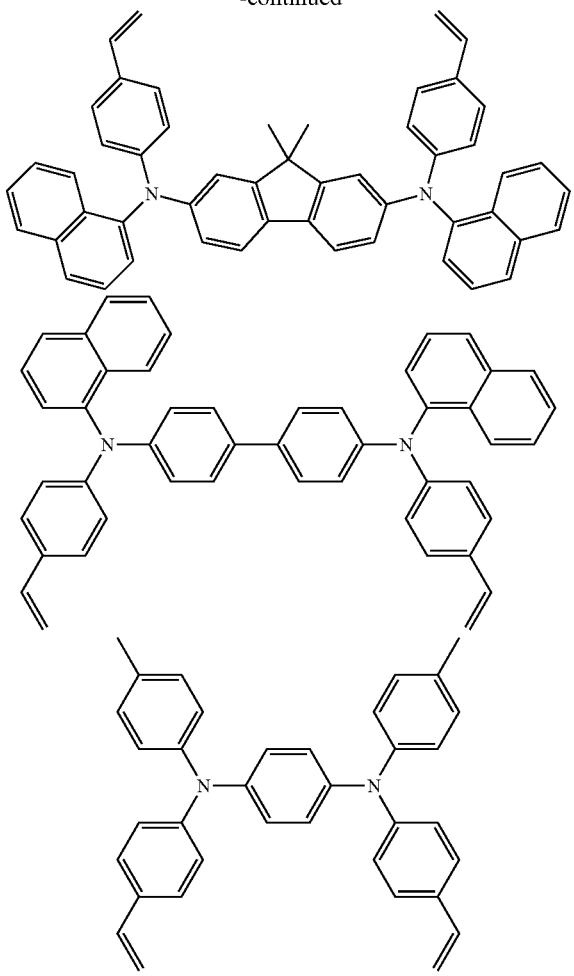

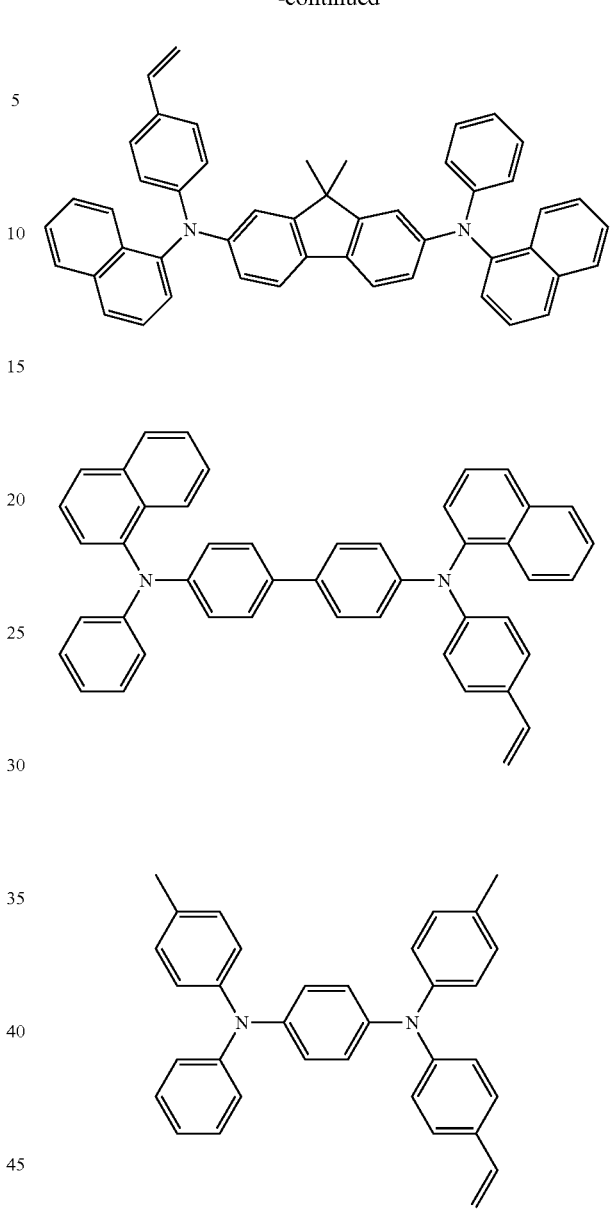

The activator can be used in amounts of, for example, 20 wt. % or less, or 10 wt. % or less, or 5 wt. % or less, with respect to the hole transporting compounds.

One Crosslinking Group

In another formulation strategy, the degree of crosslinking for formulations based on the compounds of Parts I and II can be adapted to help control parameters such as film shrinkage. For example, in one embodiment, the composition further comprises at least one third arylamine compound, different from the first and second arylamine compounds, wherein the third arylamine compound has only one crosslinking group. The crosslinking moiety can be a vinyl group in a para position for a styrene.

Examples include:

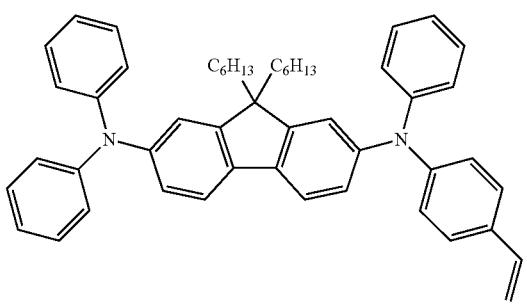

(again, the hexyl groups are representatitve; they can be, for example, any R C4 to C20 group).

Three or More Crosslinking Groups

In still another formulation strategy, the degree of crosslinking in formulations based on the compounds in Parts I and II can be adapted also to control the solvent resistance including increasing solvent resistance. For example, in one embodiment, the composition further comprises at least one third arylamine compound, different from the first and second arylamine compounds, wherein the third arylamine compound has three or more crosslinking groups, or four or more crosslinking groups, or five or more crosslinking groups. The crosslinking groups can be, for example, vinyl groups of a styrene unit. Examples include:

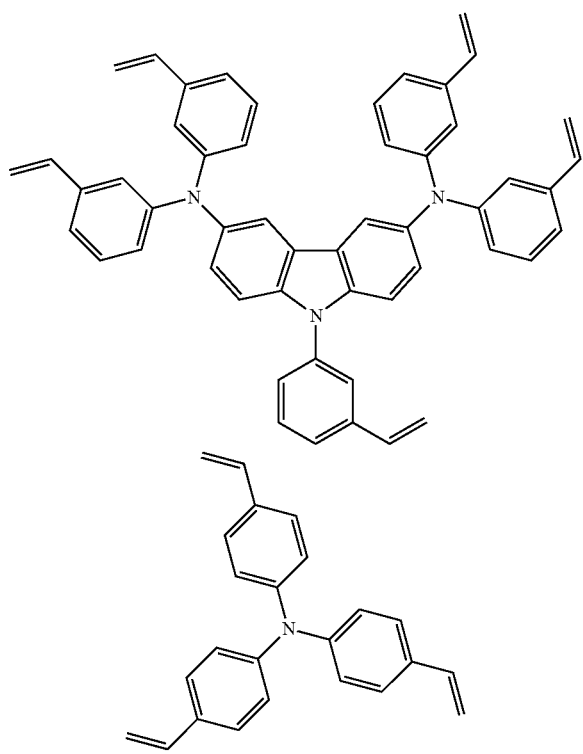

One can adapt the degree of crosslinking per molecular unit to provide a desired result.

Stabilizer

In one embodiment, the composition further comprises at least one third arylamine compound, wherein the third arylamine compound has a lower LUMO and lower or similar HOMO compared to the first and second compounds. Inclusion of such a moiety can help in quenching any electrons leaked into the hole transport layer from the emissive layer, hence stabilizing the HTL from any degradation because of electron current.

An example of a stabilizer is:

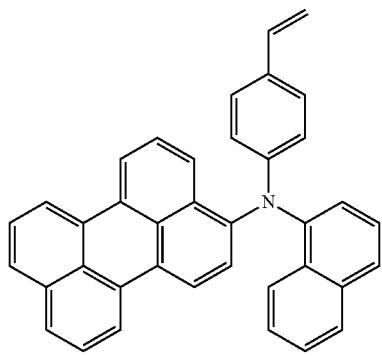 [SMILES: C=Cc1ccc(N(c2cccc3ccccc23)c2ccc3c4cccc5cccc(c6cccc2c63)c54)cc1]

Exclusion of Polymer

The composition can be free or substantially free of polymeric materials before crosslinking. For example, the composition can be free or substantially free of materials having a molecular weight of more than 5,000 g/mole or more, or free of materials having a molecular weight of more than 10,000 g/mol. The composition, before crosslinking, can comprise only materials having lower molecular weights such as below 5,000 g/mol, or below 2,000 g/mole, or below 1,000 g/mol. The amount of polymer can be less than 1 wt. %, or less than 0.1 wt. %, or less than 0.01 wt. %, for example.

Purity of Materials

The compounds and materials described herein generally should be purified as much as possible to have a good device performance. For example, impurities such as metals (e.g., Pd, Sn) or halogens (e.g., Cl, Br) should be reduced to less than 100 ppm, or less than 80 ppm, or less than 60 ppm, or less than 40 ppm, or less than 20 ppm.

Synthesis of Hole Transporting Compounds

Figure 10:
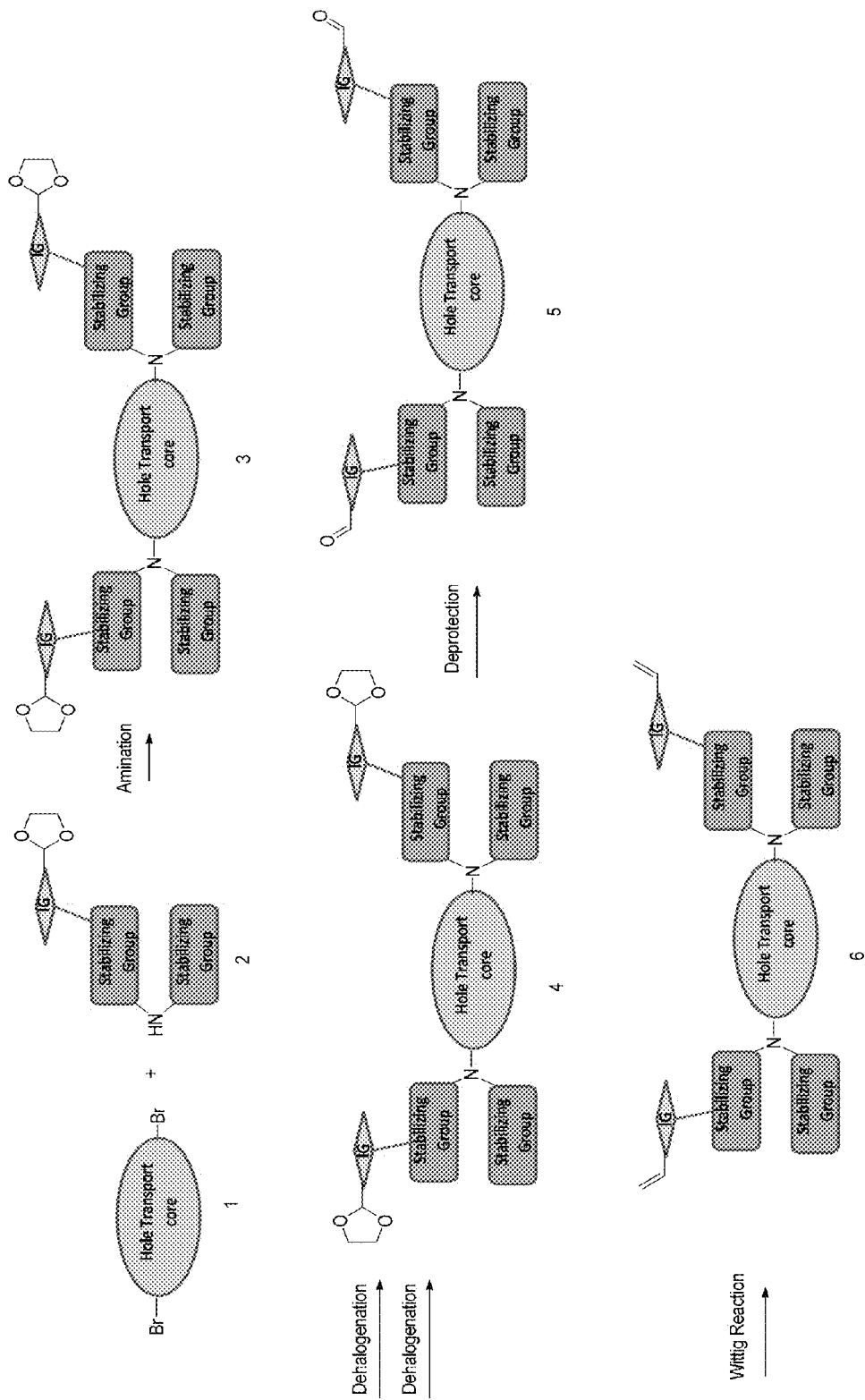
FIG. 10 illustrates a schematic of synthesis strategy.

One skilled in the art can use organic chemistry to link together the core moiety, the arylamine moieties, and the intractability group or groups. Synthesis is described in, for example, March's Advanced Organic Chemistry, 6$^{th}$ Ed., Wiley, 2007, as well as in references cited herein. For example, a schematic for synthesis of hole transporting compounds is shown in FIG. 10. Examples of major reactions for HTL synthesis include amination, dehalogenation, deprotection, and Wittig reactions. Additional synthetic methods are shown in the working examples.

The hole transport formulations, mixtures, and compounds described herein can be further processed into inks, films, and devices.

Part III

Inks, Methods of Making Films and Devices

Inks and Solvent System

The compositions described herein can be used in solid or can be formulated into liquid form as inks. Hence, in one embodiment, the composition further comprises a solvent system to form an ink. Solvent systems are known. See, for example, WO 2010/093592 (Cheon et al.).

The solid content of the ink can be adapted for a particular application. In one embodiment, the composition further comprises a solvent system to form an ink, wherein the solid content of the ink is at least 0.1 w/w % of solvent, or at least 0.3 w/w % of the solvent, or at least 1 w/w % of solvent.

The solvent system can comprise one solvent, two solvents, or three or more solvents (e.g., solvent blends can be used). Organic solvents can be used. In one embodiment, the solvent system comprises toluene as solvent.

Solvents can include aromatic hydrocarbons in the neutral and oxidized forms. Solvents such as tetrahydrofuran, chloroform, or aromatic hydrocarbons in the neutral and oxidized forms can be used. Additional solvents include tetrahydrofuran, chloroform, alkylated benzenes, halogenated benzenes, NMP, DMF, DMAc, DMSO, methyl ethyl ketone, cyclohexanone, chloroform, dichloromethane, acetone, THF, dioxanes, ethyl acetate, ethyl benzoate, ethylene carbonate, propylene carbonate, or combinations thereof.

For environmental compliance, one or more nonhalogenated solvents may be selected. Halogenated solvents can be substantially or totally excluded (e.g., used in less than 10%, or less than 5%, or less than 1%, or less than 0.1% by volume of total solvent carrier). In weighing such additional factors, it may be helpful to consult references such as, for example, Cheremisnoff, N. P., *Industrial Solvents Handbook*, 2$^{nd}$ Ed. (Marcel Dekker, New York, 2003); Ash, M, *Handbook of Solvents*, 2$^{nd}$ Ed. (Syapse Information Resources, 2003); Wypych, G., *Handbook of Solvents (Chemical)* (Noyes Publications, 2000); Hansen, C. M., Durkee, J. and Kontogeorgis, G, *Hanson Solubility Parameters: A User's Handbook* (Taylor and Francis, 2007); all of which are incorporated by reference in their entireties.

Solvents to be considered may include ethers (optionally substituted with C1-C10 alkyl chains) such as anisole, ethoxybenzene, dimethoxy benzenes and glycol ethers, such as: ethylene glycol diethers such as 1,2-dimethoxy ethane, 1,2-diethoxy ethane, 1,2-dibutoxy ethane; diethylene glycol diethers such as diethylene glycol dimethyl ether, diethylene glycol diethyl ether; propylene glycol diethers such as propylene glycol dimethyl ether, propylene glycol diethyl ether, propylene glycol dibutyl ether; dipropylene glycol di ethers such as dipropylene glycol dimethyl ether, dipropylene glycol diethyl ether, dipropylene glycol dibutyl ether; also, higher analogs (tri- and tetra-) of the ethylene glycol and propylene glycol ethers mentioned above.

Still other solvents can be considered, such as ethylene glycol monoether acetates and propylene glycol monoether acetates, wherein the ether can be selected, for example, from: methyl, ethyl, n-propyl, iso-propyl, n-butyl, sec-butyl, tert-butyl, cyclohexyl. Also, higher glycol ether analogs of above list such as di-, tri- and tetra-. Examples include, but are not limited to, propylene glycol methyl ether acetate, 2-ethoxyethyl acetate, 2-butoxyethyl acetate.

Yet other possible solvents include aliphatic and aromatic ketones such as acetonyl acetone, methyl isobutyl ketone, methyl isobutenyl ketone, 2-hexanone, 2-pentanone, acetophenone, ethyl phenyl ketone, cyclohexanone, cyclopentanone.

Additional possible solvents include N,N-dimethyl formamide, N,N-dimethyl acetamide, N-methyl pyrrolidone, dimethyl sulfoxide, tetramethylene sulfoxide, acetonitrile, benzonitrile, ethylene carbonate, propylene carbonate, and the like.

Other examples include cyclic ethers such as, for example, tetrahydropyran (THP). Solvent can be used such that polymerization of the solvent can be avoided. Another example is methoxyproprionitrile.

The one or more solvents can be used in varying proportions to improve the ink characteristics such as substrate wettability, ease of solvent removal, viscosity, surface tension, and jettability.

Alternatively, it may be useful to select more than one solvent, for example, a first solvent and a second solvent. In one example, the solutes can have a higher solubility in the first solvent than in the second solvent. The hole transporting compound can also have a higher solubility in the second solvent than in the first solvent. The solvent can be selected such that the first solvent can be removed at a faster rate than the second solvent in a drying step.

Reacted and Dried Form of Compositions

Also described herein are compositions, wherein the reactive compositions are either partially reacted or fully reacted. For example, in one embodiment, the intractable groups are polymerizable groups, and the polymerizable groups are reacted. In one embodiment, a composition is prepared by reaction of the intractability groups of the first and second compound of the compositions described herein.

The compositions can be converted into films by methods known in the art. Hence, in one embodiment, the intractable groups are polymerizable groups, and the polymerizable groups are reacted, and the composition is in the form of a thin film.

Methods of Forming Films

Coated substrates can be formed. One or more layers of film can be added to a preexisting film or substrate. For example, another embodiment provides a method comprising: providing a substrate comprising a hole injection layer, coating the substrate with at least one ink comprising at least one hole transport material comprising intractability groups to form a coated substrate, heating the coated substrate. The hole transport material can comprise one or more of the compositions described herein.

In one embodiment, the ink is subjected to pre-crosslinking before coating the ink on the substrate. In one embodiment, the ink is subjected to thermal pre-crosslinking before coating the ink on the substrate. In one embodiment, the ink is subjected to thermal pre-crosslinking to form a gel before coating the ink on the substrate. In one embodiment, the ink is subjected to thermal pre-crosslinking at at least 150° C. to form a gel before coating the ink on the substrate. In one embodiment, the ink is subjected to UV light pre-crosslinking before coating the ink on the substrate.

In one embodiment, the coated substrate is subjected to UV light to induce pre-crosslinking before heating the coated substrate.

In one embodiment, the coated substrate is heated to at least 200° C. In one embodiment, the coated substrate is heated to at least 250° C.

The quality of the film can be examined by optical microscopy, looking for film defects, formation of aggregates and beads, dewetting of the film, and pinholes.

In one embodiment, which is comparative, after heating, the coated substrate shows films with beads formed on the top layer interspersed with the area of the lower film where the top hole transport layer film has dewetted (in the optical microscope).

In one embodiment, after heating, the coated substrate shows defect free, smooth and continuous films conforming and wetting well on the lower lying hole injection layer (in the optical microscope).

Films can be evaluated at both low and high magnifications to isolate the presence of both large and small scale defects and ensure an overall smooth continuous coating.

The film formation can be carried out by methods known in the art including drop coating, spin coating, ink jet printing, slot die coating, nozzle printing, screen printing, and the like.

Characterizing Films

In one embodiment, after heating the coated substrate is stable to toluene solvent wash so that retains at least 90% of the initial thickness before the wash. In one embodiment, after heating the coated substrate is stable to toluene solvent wash so that retains at least 95% of the initial thickness before the wash.

In one embodiment, after heating the coated substrate is stable to immersion in toluene for 5-10 minutes so that it retains at least 90% of the initial thickness before wash and does not show an increase in the thickness beyond 110% of the initial thickness.

In one embodiment, after heating the coated substrate is stable to immersion in toluene for 5-10 minutes so that it retains at least 95% of the initial thickness before wash and does not show an increase in the thickness beyond 105% of the initial thickness.

The film quality (smoothness) can be evaluated by atomic force microscopy, and films can show an rms roughness of 5 nm or below. The AFM micrographs can help to ensure good film quality at the nanoscale and also helps in understanding film morphology and its effect on device performance.

On the films deposited on the substrates, other measurements can be performed such as AC2 can be used to measure the HOMO energy of films. Absorption measurements (UV-VIS) can be done to calculate the bandgap of the hole transport material. The LUMO can be estimated by subtracting the band gap from the HOMO. Also photoluminescence measurements can be done on the hole transport films to study their emission characteristics.

In one embodiment, the coating of the coated substrate shows a Tg of less than 200° C., or less than 150° C.

Substrate and Hole Injection Layer

Solution processing for OLED fabrication is known in the art. Orthogonal solubility principles can be used. In particular, the hole transport compounds and formulations can be applied on top of a hole injection layer (HIL) material or film. The hole injection layers can be materials soluble in water or organic solvents. Solution process can provide depositing materials from a liquid medium, including solutions, dispersions, emulsions, or other forms.

In one embodiment, the hole injection layer is an aqueous hole injection layer. For example, the HIL layer material can be soluble in water.

In one embodiment, the hole injection layer is a non-aqueous hole injection layer. For example, the HIL layer material can be soluble in organic solvent.

In one embodiment, the hole injection layer comprises a polymer. In one embodiment, the hole injection layer comprises a conjugated polymer. In one embodiment, the hole injection layer comprises a polythiophene. In one embodiment, the hole injection layer comprises a polythiophene comprising at least one alkoxy substituent. In one embodiment, the hole injection layer comprises a sulfonated polythiophene. In one embodiment, the hole injection layer comprises a polymeric arylamine. In one embodiment, the hole injection layer comprises a regioregular polythiophene. In one embodiment, the hole injection layer comprises a conjugated polymer which is soluble in water. In one embodiment, the hole injection layer comprises a conjugated polymer which is soluble in organic solvent.

For example, hole injection layers are described in the following US Patent Publications (assignee: Plextronics): 2006/0078761; 2008/0248313; 2009/0256117; 2009/0230361; 2010/0108954; 20100292399; 2010/0072462; 2010/0109000; 2011/0147725, which are all hereby incorporated by reference in their entireties.

Examples of aqueous hole injection layers are described in 2008/0248313 (Seshadri et al.)

Examples of non-aqueous hole injection layers are described in 2006/0078761 and 2009/0256117 (Seshadri et al.). For example, the HIL can be based on a 3,4-disubstituted polythiophene including a poly(3,4-dialkoxythiophene).

OLED devices are also fabricated with emitting layers and other layers known in the art of OLED devices. In one embodiment, the method further comprises the step of coating an emitting layer on the coated substrate.

In one embodiment, the ink comprises at least two hole transport materials comprising intractability groups. In one embodiment, the ink comprises at least two hole transport materials each comprising a different intractability group. The two different intractability groups can be adapted to function together during film formation. For example, one might react at a lower temperature, and one might react at a higher temperature. In general, one tries to have all or as many as possible of the intractability groups to react.

Device Fabrication and Characterization

Devices can be fabricated by methods known in the art and can be characterized by methods known in the art.

Figure 11:
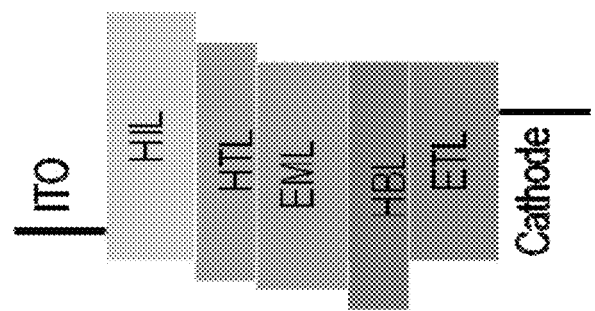
FIG. 11 illustrates an embodiment for an OLED device.

As illustrated in FIG. 11, an organic light emitting diode can comprise a series of layers including, for example, ITO: Transparent anode, typically
HIL: Hole injection layer to facilitate charge injection
HTL: Hole transport layer which carries charges
EML: Emissive layer where light is emitted
HBL: Hole blocking layer to prevent charge leakage
ETL: Electron transport layer to facilitate charge injection
Cathode Layers can be supported by substrates including flexible, or rigid, or organic, or inorganic substrates.

Additional examples of layers and devices, and related methods of making, testing, and using, can be found in, for example, US Patent Publication Nos. 2005/0184287; 2006/0032528; 2008/0286566; 2009/0159877; 2010/0187500; 2010/0187510; 2010/0207109; 2010/0213446; 2010/0244665; WO 07076146; WO 07079103; WO 07120143; WO 07145979; WO 08024378; WO 08024379; WO 08024380; WO 08106210; WO 08150872; WO 08150943; WO 09018009; WO 09052085; WO 09055532; WO 09067419; WO 09097377; WO 09140570.

Applications

OLEDs can be used in, for example, display or lighting applications. Other applications are described in, for example, (1) *Highly Efficient OLEDS with Phosphorescent Materials* (Ed. H. Yerrin), 2008, Wiley-VCH, (2) *Organic Light Emitting Devices: Synthesis, Properties, and Applications* (Eds. Mullen, Scherf), 2006, (3) *Organic Light Emitting Methods and Devices*, (Li and Meng), 2007, CRC. See also Shirota et al., *Chem. Rev.*, 2007, 107, 953-1010 for OLEDs, OPVs, OFETs, and other applications.

Embodiments from U.S. Provisional 61/361,147

Embodiments described more fully in priority U.S. provisional application 61/361,147 filed Jul. 2, 2010 (assignee: Plextronics) are also provided for herein including hole transport materials, and this priority provisional is fully incorporated by reference in its entirety for all purposes herein.

For example, one embodiment provides a composition comprising: at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present. In one embodiment, the compound further comprises at least one, or at least two, or at least four crosslinking group. In one embodiment, the compound further comprises at least one crosslinking group, and the compound is crosslinked. In one embodiment, the compound further comprises at least one crosslinking group which is a vinyl, perfluorocyclobutane, oxetane, silane, or benzocyclobutene group. In one embodiment, the compound further comprises at least one crosslinking group which comprises ethylenic unsaturation. In one embodiment, the compound comprises at least one crosslinking group which is vinyl. In one embodiment, the compound further comprises at least one crosslinking group which comprises ethylenic unsaturation optionally linked to the compound with a spacer group. In one embodiment, the compound further comprises at least one crosslinking group which comprises ethylenic unsaturation optionally linked to the compound with a spacer group, wherein the spacer group is —$(CH_2)_n$—, wherein n is 0-6. In one embodiment, the compound further comprises at least one crosslinking group which comprises ethylenic unsaturation linked to the compound with a spacer group, wherein the spacer group is —$(CH_2)_n$—, wherein n is 1-6. In one embodiment, the compound comprises at least one, or at least two, or at least four arylamine groups. In one embodiment, the compound comprises at least one arylamine group, wherein the arylamine group comprises a carbazole group. In one embodiment, the compound comprises at least one arylamine group, wherein the arylamine group is a tertiary arylamine. In one embodiment, the compound comprises at least one, or at least two thiophene groups. In one embodiment, the compound comprises at least one benzodithiophene group. In one embodiment, the compound comprises at least one benzo[1,2-b:4,5-b']dithiophene group. In one embodiment, the compound comprises at least two sulfur atoms, at least two oxygen atoms, and at least two sulfur-oxygen interactions. In one embodiment, the compound comprises at least one benzodithiophene group which is substituted at the four and eight positions with an optionally substituted aryl ring.

In one embodiment, the compound comprises at least one benzodithiophene group which is substituted at the four and eight positions with an optionally substituted aryl ring comprising an oxygen-containing substituent. In one embodiment, the compound is represented by B1-A-B2, wherein B1 and B2 independently can be the same or different. In one embodiment, the compound is represented by B1-A-B2, wherein B1 and B2 independently can be the same or different, and A comprises at least one benzodithiophene group, and B1 and B2 each comprise at least one arylamine group. In one embodiment, the compound is represented by B1-A-B2, wherein B1 and B2 independently can be the same or different, and A comprises at least one benzodithiophene group, and B1 and B2 each comprise at least two arylamine groups. In one embodiment, the compound is represented by B1-A-B2, wherein B1 and B2 independently can be the same or different, and A comprises at least one benzodithiophene group, and B1 and B2 each comprise at least two arylamine groups, wherein B1 and B2 are linked to the benzodithiophene group at the 2 and 6 positions of the benzodithiophene group. In one embodiment, the compound is represented by:

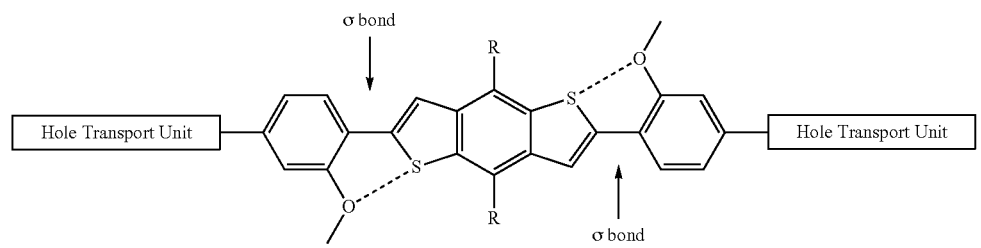

In one embodiment, the sulfur and the oxygen are linked by three carbon atoms. In one embodiment, the sulfur and the oxygen are linked by a linkage moiety comprising at least three carbon atoms including at least one sigma bond. In one embodiment, the compound comprises at least 12, or at least 15, benzene rings. In one embodiment, the compound comprises at least 12 benzene rings, at least two thiophene rings, and at least two nitrogen atoms. In one embodiment, the compound comprises at least 15 benzene rings, at least two thiophene rings, and at least four nitrogen atoms. In one embodiment, the compound is soluble in organic solvent such as toluene. In one embodiment, the compound shows a mobility of at least $10^{-5}$ cm$^2$/Vs, or at least $10^{-4}$ cm$^2$/Vs, or at least $7.64 \times 10^{-4}$ cm$^2$/Vs, or the compound is soluble in organic solvent, and the compound shows a mobility of at least $7.64 \times 10^{-4}$ cm$^2$/Vs. In one embodiment, the sulfur-oxygen interaction can be detected by x-ray diffraction. In one embodiment, the sulfur-oxygen interaction can be detected by an NMR method. In one embodiment, the composition further comprises at least one additional, different hole transporting compound. In one embodiment, the compound has a molecular weight of about 2,000 or less. In one embodiment, the compound has a molecular weight of about 800 to about 2,000. In one embodiment, the compound has an ionization potential of about −5.2 eV to about −5.7 eV. In one embodiment, the compound comprises at least one crosslinking group which has been crosslinked, and the composition shows a 95% solvent wash resistance for toluene. In one embodiment, the compound comprises a benzodithiophene core linked at the 2 and 6 positions to a hole transporting unit, each unit comprising two arylamine groups, wherein each hole transporting unit is further functionalized with at least one crosslinking group. In one embodiment, the compound comprises a benzodithiophene core linked at the 2 and 6 positions to a hole transporting unit, each unit comprising at least one arylamine group, wherein the benzodithiophene is functionalized at the 4 and 8 positions with at least one crosslinking group. In one embodiment, the compound comprises at least one crosslinking group which has been crosslinked, at least four arylamine groups, at least one benzodithiophene group, has a molecular weight of about 2,000 or less before crosslinking, is soluble in organic solvent before crosslinking, and has a hole mobility of at least $10^{-4}$ cm$^2$/Vs after crosslinking.

Another embodiment provides a composition comprising: at least one compound comprising at least one first thiophene ring moiety, and also comprising at least one first benzene ring moiety, wherein the first thiophene ring moiety is covalently bonded to the first benzene ring moiety at the 2 or 5 position of the thiophene ring to form a thiophene substituent for the first benzene ring moiety, and wherein the first benzene ring moiety comprises at least one oxygen atom ortho to thiophene ring substituent of the first benzene ring moiety, and further wherein the first benzene ring moiety is linked to at least one arylamine group.

Another embodiment provides a composition comprising: at least one arylamine hole transporting compound having a molecular weight of about 5,000 or less, wherein the compound comprises at least one sulfur atom which is part of a thiophene ring, and at least one oxygen atom, wherein the sulfur and oxygen atom are positioned in the compound so that a sulfur-oxygen intramolecular interaction is present, wherein the compound further comprises at least one crosslinking group.

Another embodiment provides a composition comprising: at least one arylamine compound comprising at least one first thiophene ring moiety, and also comprising at least one first benzene ring moiety, wherein the first thiophene ring moiety is covalently bonded to the first benzene ring moiety at the 2 or 5 position of the thiophene ring to form a thiophene substituent for the first benzene ring moiety, and wherein the first benzene ring moiety comprises at least one oxygen atom ortho to thiophene ring substituent of the first benzene ring moiety, and further wherein the first benzene ring moiety is linked to at least one arylamine group, and wherein the compound further comprises at least one crosslinking group.

Another embodiment provides a composition prepared by crosslinking a composition comprising at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present, wherein the compound further comprises at least one crosslinking group.

Another embodiment provides a device comprising: at least one anode, at least one cathode, at least one light emission layer, at least one hole transporting layer, wherein the hole transport layer comprises a composition prepared by crosslinking a composition comprising at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present, wherein the compound further comprises at least one crosslinking group.

Another embodiment provides a coated substrate comprising a coating composition prepared by crosslinking a composition comprising at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present, wherein the compound further comprises at least one crosslinking group. Another embodiment provides at least one composition comprising: at least one solvent, at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present, wherein the compound further comprises at least one crosslinking group. Another embodiment provides a method comprising: providing at least one ink composition comprising at least one solvent, and at least one hole transporting compound having a molecular weight of about 5,000 or less, wherein the compound comprises at least one sulfur atom and at least one oxygen atom, wherein the sulfur and oxygen atom are positioned in the compound so that a sulfur-oxygen intramolecular interaction is present, wherein the compound further comprises at least one crosslinking group; coating the composition onto a substrate, removing the at least one solvent, crosslinking to provide a coated substrate.

Another embodiment provides a composition comprising at least one moiety represented by formula (I)

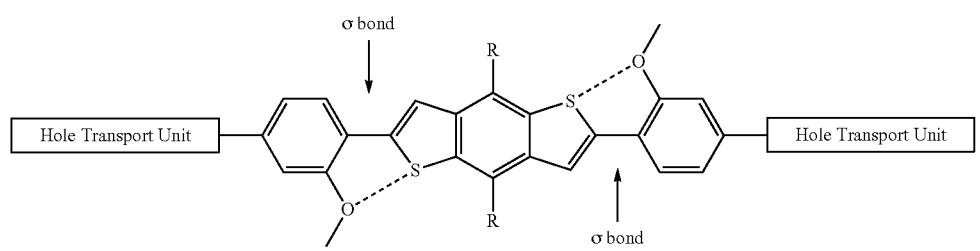

wherein the hole transporting units further comprise at least one crosslinking group. In one embodiment, provided is a composition comprising a crosslinked form of the moiety represented by formula (I).

Another embodiment provides a composition comprising: at least one hole transporting compound having a molecular weight of about 5,000 or less, wherein the compound comprises at least two benzodithiophene moieties, and at least two fluorene moieties linked to the benzodithiophene moieties, and wherein the compound comprises at least two sulfur atoms and at least two oxygen atoms, wherein the sulfur and oxygen atoms are positioned in the compound so that a sulfur-oxygen intramolecular interaction is present.

Methods of making these compounds are also described in the priority provisional application.

WORKING EXAMPLES

Additional embodiments are provided in the following working examples.

Working Example 1: Synthesis of PLX-D

Synthesis of 9,9-dioctyl-N2,N7-di-m-tolyl-9H-fluorene-2,7-diamine (1)

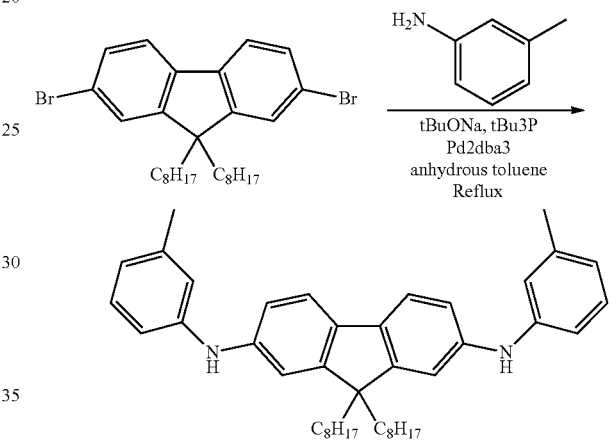

To an oven-dried three-neck round-bottom flask under nitrogen, were added 600 mL anhydrous toluene obtained from the solvent dispenser, 50.0 g 9,9-dioctyl-2,7-dibromofluorene, and 23.7 mL m-toluidine. After the reaction mixture was degassed with strong nitrogen flow for 30 minutes, 43.81 g sodium tert-butoxide, 3.34 g tris(dibenzylideneacetone)dipalladium(0) ($Pd_2dba_3$), and 2.22 g tri-tert-butyl phosphine in 30 mL anhydrous toluene were added. The reaction mixture was heated to reflux. After three hours, the heating was turn off, and the reaction was allowed to cool down to room temperature. The reaction mixture was filtered through a Celite/silica gel plug. The product (51.9 g) was purified by flash chromatography using hexane, 1% then 3% ethyl acetate in hexane for first column, and using the same eluents for second column. The structure was confirmed by NMR.

Synthesis of 2

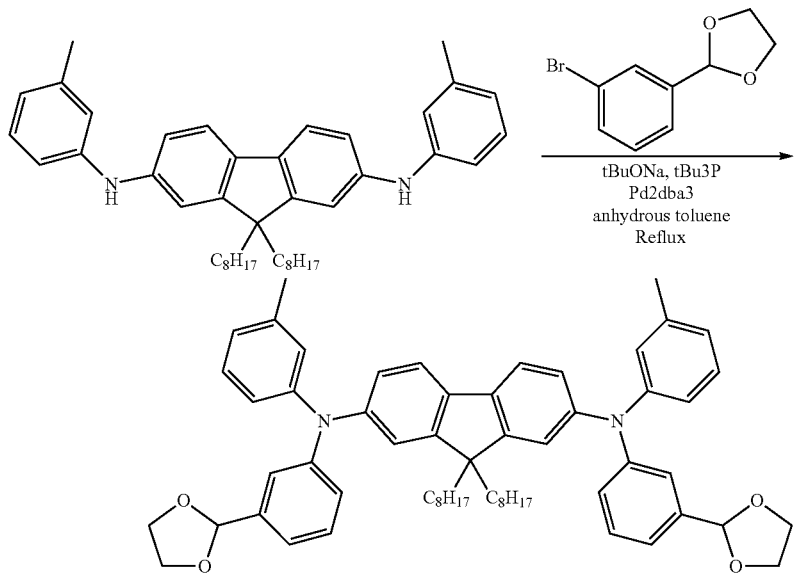

Synthesis of N2,N7-bis(3-(1,3-dioxolan-2-yl)phenyl)-9,9-dioctyl-N2,N7-di-m-tolyl-9H-fluorene-2,7-diamine (2)

To an oven-dried three-neck round-bottom flask under nitrogen, were added 1000 mL anhydrous toluene obtained from the solvent dispenser, 51.0 g 9,9-dioctyl-N2,N7-di-m-tolyl-9H-fluorene-2,7-diamine, and 38.3 mL 2-(3-bromophenyl)-1,3-dioxolane. After the reaction mixture was degassed with strong nitrogen flow for 30 minutes, 24.31 g sodium tert-butoxide, 3.09 g tris(dibenzylideneacetone)dipalladium(0) ($Pd_2dba_3$), and 2.05 g tri-tert-butyl phosphine in 40 mL anhydrous toluene were added. The reaction mixture was heated to reflux. After 2 hours, the heating was turn off, and the reaction was allowed to cool down to room temperature. The reaction mixture was filtered through a Celite/silica gel plug. The product (61.7 g) was purified by flash chromatography using hexane and 5% ethyl acetate in hexane for first column, and using the same eluents for second column. The structure was confirmed by NMR.

Synthesis of 3

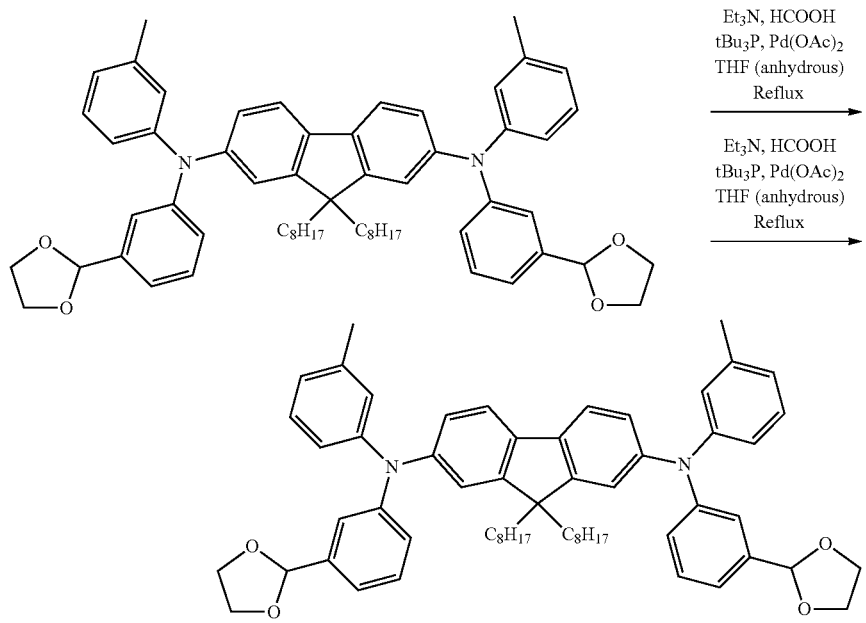

Dehalogenation of N2,N7-bis(3-(1,3-dioxolan-2-yl)phenyl)-9,9-dioctyl-N2,N7-di-m-tolyl-9H-fluorene-2,7-diamine To a clean and dry round bottom flask under nitrogen, were added 60.0 g N2,N7-bis(3-(1,3-dioxolan-2-yl)phenyl)-9,9-dioctyl-N2,N7-di-m-tolyl-9H-fluorene-2,7-diamine, 1000 mL anhydrous THF, 92.79 mL triethylamine, and 25.12 mL formic acid. After the reaction mixture was degassed with strong nitrogen flow for 30 minutes, 1.49 g palladium (II) acetate and 2.02 g tri-tert-butyl phosphine in 30 mL toluene were added. After the reaction was heated to reflux for 4 hours, the heat was removed and the reaction was allowed to cool down to room temperature. The reaction mixture was filtered through a Celite/silica gel plug, and the solvent was removed by evaporation. The crude product was dried under vacuum, and was carried on second dehalogenation reaction without further purification.

To a clean and dry round bottom flask under nitrogen, were added 60.0 g N2,N7-bis(3-(1,3-dioxolan-2-yl)phenyl)-9,9-dioctyl-N2,N7-di-m-tolyl-9H-fluorene-2,7-diamine, 1000 mL anhydrous THF, 92.79 mL triethylamine, and 25.12 mL formic acid. After the reaction mixture was degassed with strong nitrogen flow for 30 minutes, 1.49 g palladium (II) acetate and 2.02 g tri-tert-butyl phosphine in 30 mL toluene were added. After the reaction was heated to reflux for 4 hours, the heat was removed and the reaction was allowed to cool down to room temperature. The reaction mixture was filtered through a Celite/silica gel plug. The product (34.0 g) was purified by flash chromatography using hexane, 10% and 15% ethyl acetate in hexane. The structure was confirmed by NMR.

Synthesis of 4

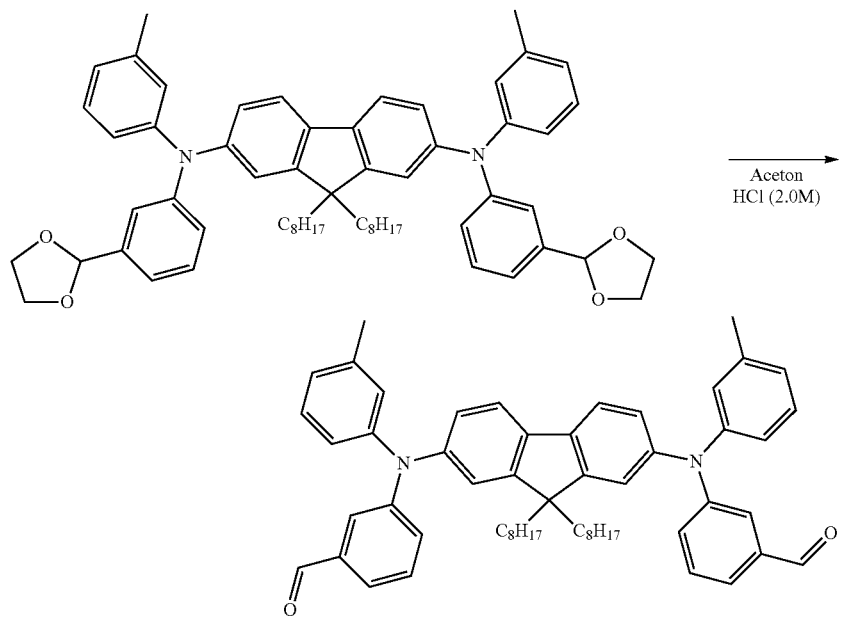

Synthesis of 3,3'-((9,9-dioctyl-9H-fluorene-2,7-diyl)bis(m-tolylazanediyl))dibenzaldehyde To a three-neck round-bottom flask, were added 34.0 g N2,N7-bis(3-(1,3-dioxolan-2-yl)phenyl)-9,9-dioctyl-N2, N7-di-m-tolyl-9H-fluorene-2,7-diamine and in 1000 mL acetone. 189.5 mL 2 M hydrochloric acid solution was added slowly to the reaction mixture through an addition funnel. The reaction was monitored by TLC. After the reaction was done showed by TLC, the solvent was removed by evaporation. 1000 mL Ethyl acetate was added, and the reaction mixture was extracted using DI water (3×750 mL). The combined organic layer was dried over magnesium sulfate. After filtration, the solvent was removed by evaporation. The product (27.8 g) was obtained, and was carried on to next reaction without further purification. The structure was confirmed by NMR.

Synthesis of 5 (PLX-D)

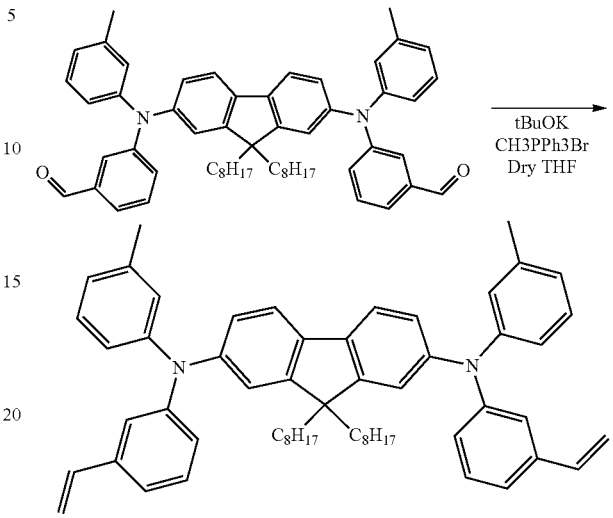

Synthesis of 9,9-dioctyl-N2,N7-di-m-tolyl-N2,N7-bis(3-vinylphenyl)-9H-fluorene-2,7-diamine To a oven-dried three-neck round-bottom flask under nitrogen, were added 500 mL anhydrous THF, 11.95 g potassium tert-butoxide, and 36.82 g methyltriphenylphosphonium bromide. The mixture was stirred for 30 min. 27.8 g 3,3'-((9,9-dioctyl-9H-fluorene-2,7-diyl)bis(m-tolylazanediyl))dibenzaldehyde in 500 mL anhydrous THF was added through an additional funnel dropwise to the reaction mixture over 30 min. After the reaction was stirred for 2 hours, the reaction solution was filtered through a Celite/silica gel plug, and solvent was removed by evaporation. The product was first purified by flash chromatography using 100% hexane and then 1% ethyl acetate in hexane. The structure was confirmed by NMR. The further purification was performed by dissolving the column pure solid in minimal amount of HPLC acetone and then precipitating in HPLC Methanol, giving the final product (9.79 g). The structure was confirmed by NMR.

Working Example 2: Synthesis of PLX-I

Synthesis of 6

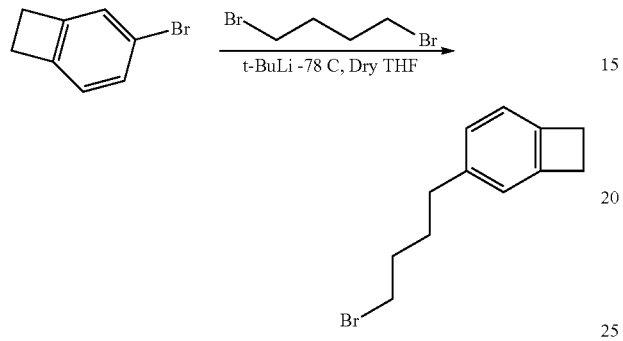

Synthesis of 3-(4-bromobutyl)bicyclo[4.2.0]octa-1 (6),2,4-triene

To an oven-dried three-neck round-bottom flask equipped with an additional funnel and thermometer under nitrogen, were added 500 mL anhydrous THF and 25.0 g 4-bromobenzocyclobutane. The reaction mixture was then cooled down to −73° C. in acetone/dry ice bath. 161 mL tert-Butyllithium (2M) was added drop by drop to the reaction through the addition, while keeping the reaction temperature below −65° C. After addition of tert-butyl lithium, the dry ice/acetone bath was removed and the reaction was allowed to warm up to −20° C., and then cooled down to −73° C. in dry ice/acetone bath. 65.7 mL 1,4-dibromobutane was added drop-wise via syringe, ensuring the reaction temperature stayed lower than −65° C. The reaction was allowed to slowly warm to room temperature overnight. The reaction was quenched by the addition of isopropanol (25 mL), and the solvent was removed by rotary evaporation. Ethyl acetate (500 mL) was added and then extracted with DI water (1000 mL×2) and brine (200 mL×5). The combined organic layer was dried over anhydrous magnesium sulfate, and the solvent was removed by evaporation. The excess starting material, 1,4-dibromobutane, was removed by vacuum distilled at 90° C. Filtration through a Celite/silica gel plug afforded 24.1 g NMR and GC-MS pure product.

Synthesis of 7

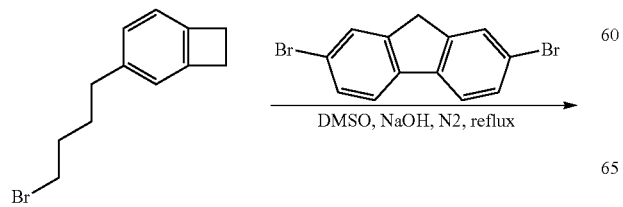

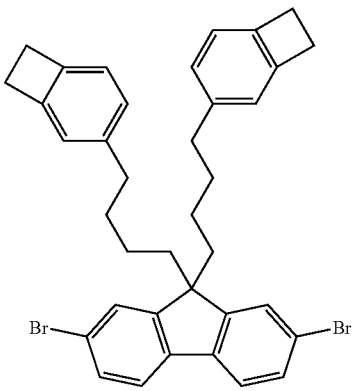

Synthesis of 9-(4-(bicyclo[4.2.0]octa-1(6),2,4-trien-3-yl)butyl)-9-(4-(bicyclo[4.2.0]octa-1,3,5-trien-3-yl)butyl)-2,7-dibromo-9H-fluorene To an oven-dried three-neck round-bottom flask under nitrogen, were added 25.97 g of 2,7-dibromofluorene, 32.06 g sodium hydroxide, 1.33 g KI, and 300 mL anhydrous DMSO. The 46 g 3-(4-bromobutyl)bicyclo[4.2.0]octa-1(6), 2,4-triene 300 mL anhydrous DMSO was added via cannula. The reaction was heated to 80° C. After 4 hours, the reaction was quenched by the addition of DI water (10 mL). The excess salt was removed by filtration. 500 mL Ethyl acetate was added, and extracted with DI water (3×300 mL) and brine (3×300 mL). The combined organic layer was dried over anhydrous magnesium sulfate. Magnesium sulfate was removed by filtration, and the solvent was removed by rotary evaporation. The product (43 g) was purified by flash chromatography using hexane. The structure was confirmed by NMR.

Synthesis of 8 (PLX-I)

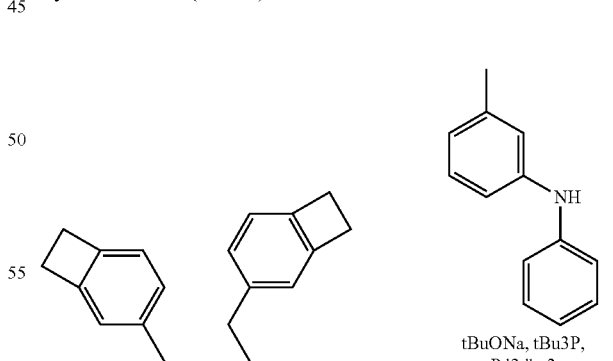

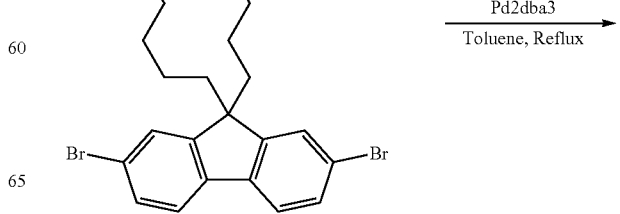

73
-continued

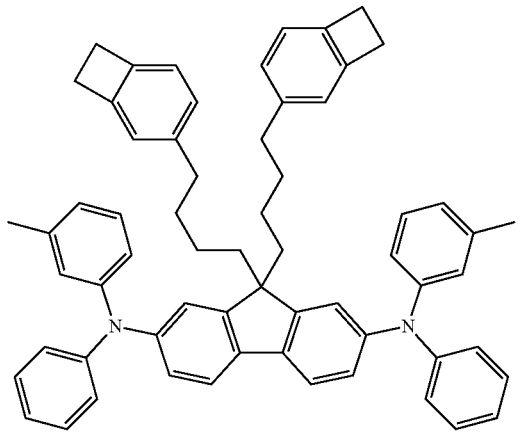

Synthesis of 9-(4-(bicyclo[4.2.0]octa-1(6),2,4-trien-3-yl)butyl)-9-(4-(bicyclo[4.2.0]octa-1,3,5-trien-3-yl)butyl)-N2,N7-diphenyl-N2,N7-di-m-tolyl-9H-fluorene-2,7-diamine To an oven-dried three-neck round-bottom flask under nitrogen, were added 600 mL anhydrous toluene, 14.3 g 9-(4-(bicyclo[4.2.0]octa-1(6),2,4-trien-3-yl)butyl)-9-(4-(bicyclo[4.2.0]octa-1,3,5-trien-3-yl)butyl)-2,7-dibromo-9H-fluorene, and 9.2 mL 3-methyldiphenylamine. After the reaction mixture was degassed with strong nitrogen flow for 30 minutes, 6.44 g sodium tert-butoxide, 0.82 g tris(dibenzylideneacetone)dipalladium(0) (Pd$_2$dba$_3$), and 0.54 g tri-tert-butyl phosphine in 15 mL toluene were added. The reaction mixture was heated to reflux. After three hours, the heating was turn off, and the reaction was allowed to cool down to room temperature. The reaction mixture was filter through a Celite/silica gel plug. The product (13.1 g) was purified by flash chromatography using hexane, 1% then 5% ethyl acetate in hexane solution. The structure was confirmed by NMR.

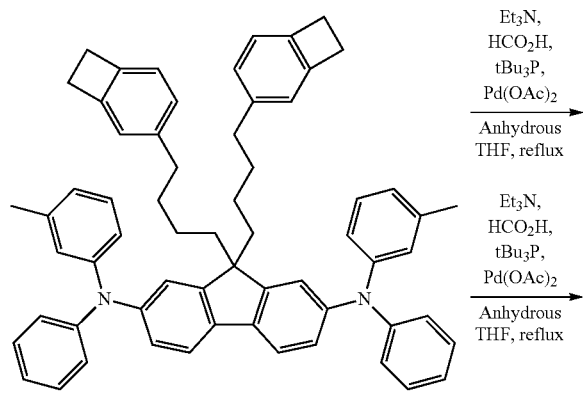

74
-continued

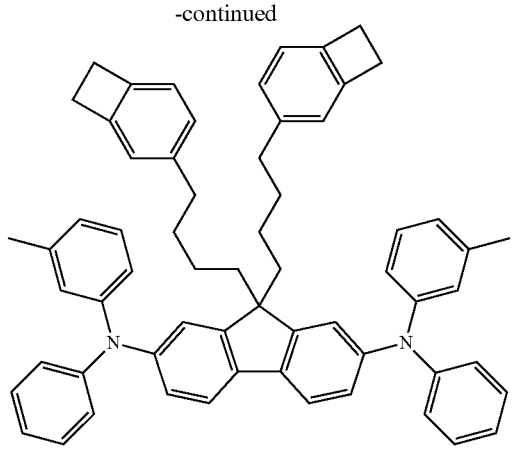

Dehalogenation of 9-(4-(bicyclo[4.2.0]octa-1(6),2,4-trien-3-yl)butyl)-9-(4-(bicyclo[4.2.0]octa-1,3,5-trien-3-yl)butyl)-N2,N7-diphenyl-N2,N7-di-m-tolyl-9H-fluorene-2,7-diamine To a clean and dry round bottom flask under nitrogen, were added 13.1 g 9-(4-(bicyclo[4.2.0]octa-1(6),2,4-trien-3-yl)butyl)-9-(4-(bicyclo[4.2.0]octa-1,3,5-trien-3-yl)butyl)-N2,N7-diphenyl-N2,N7-di-m-tolyl-9H-fluorene-2,7-diamine, 500 mL anhydrous THF, 21.6 mL triethylamine, and 5.8 mL formic acid. After the reaction mixture was degassed with strong nitrogen flow for 30 minutes, 0.35 g palladium (II) acetate and 0.47 g tri-tert-butyl phosphine in 15 mL toluene were added to reaction mixture. After the reaction was heated to reflux for 4 hours, the heat was removed and the reaction was allowed to cool down to room temperature. The reaction mixture was filter through a Celite/silica gel plug, and the solvent was removed by evaporator. The crude product was subjected to a second dehalogenation without further purification.

To a clean and dry round bottom flask under nitrogen, were added 13.1 g 9-(4-(bicyclo[4.2.0]octa-1(6),2,4-trien-3-yl)butyl)-9-(4-(bicyclo[4.2.0]octa-1,3,5-trien-3-yl)butyl)-N2,N7-diphenyl-N2,N7-di-m-tolyl-9H-fluorene-2,7-diamine, 500 mL anhydrous THF, 21.6 mL triethylamine, and 5.8 mL formic acid. After the reaction mixture was degassed with strong nitrogen flow for 30 minutes, 0.35 g palladium (II) acetate and 0.47 g tri-tert-butyl phosphine in 15 mL toluene were added to the reaction mixture. After the reaction was heated to reflux for 4 hours, the heat was removed and the reaction was allowed to cool down to room temperature. The reaction mixture was filter through a Celite/silica gel plug, and the solvent was removed by evaporator. The product was first purified by flash chromatography using hexane and 1% ethyl acetate in hexane. The structure was confirmed by NMR. The further purification was performed by dissolving the column pure solid in minimal amount of HPLC acetone and then precipitating in HPLC Methanol, giving final product (12.38 g). The structure was confirmed by NMR.

Working Example 3: Synthesis of PLX-C

Synthesis of 9

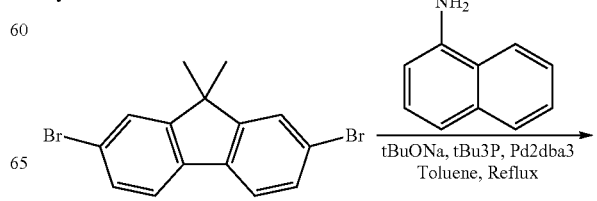

-continued

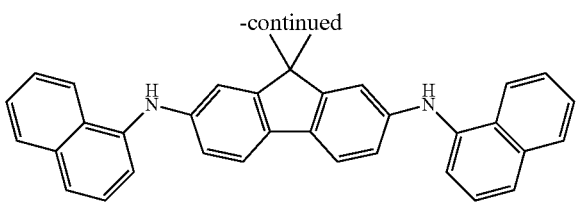

Synthesis of 9,9-dimethyl-N2,N7-di(naphthalen-1-yl)-9H-fluorene-2,7-diamine

To an oven-dried three-neck round-bottom flask under nitrogen, were added 1000 mL anhydrous toluene obtained from the solvent dispenser, 50.05 g 2,7-dibromo-9,9-dimethyl-9H-fluorene, 48.89 g naphthalen-1-amine. After the reaction mixture was degassed with strong nitrogen flow for 30 minutes, 41.02 g sodium tert-butoxide, 5.21 g tris(dibenzylideneacetone)dipalladium(0) (Pd$_2$dba$_3$), and 3.52 g tri-tert-butyl phosphine in 15 mL toluene were added. The reaction mixture was heated to reflux. After three hours, the heating was turn off, and the reaction was allowed to cool down to room temperature. The reaction mixture was filter through a Celite/silica gel plug. The crude product was first purified by flash chromatography initially using hexane, and 2.5% then 5% ethyl acetate in hexane. The final pure product was purified by sublimation. The structure was confirmed by NMR.

Synthesis of 10

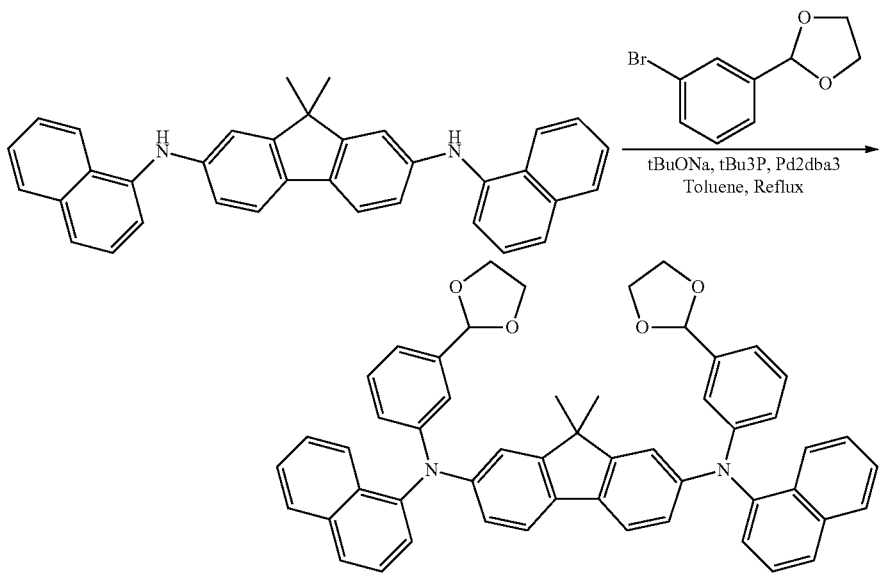

Synthesis of N2,N7-bis(3-(1,3-dioxolan-2-yl)phenyl)-9,9-dimethyl-N2,N7-di(naphthalen-1-yl)-9H-fluorene-2,7-diamine To an oven-dried three-neck round-bottom flask under nitrogen, were added 500 mL anhydrous dioxane, 5.8 g 9,9-dimethyl-N2,N7-di(naphthalen-1-yl)-9H-fluorene-2,7-diamine, 5.9 mL of 2-(Bromophenyl)-1,3-dioxalane. After the reaction mixture was degassed with strong nitrogen flow for 30 minutes, 3.25 g sodium tert-butoxide, 0.45 g tris(dibenzylideneacetone)dipalladium(0) (Pd$_2$dba$_3$), and 0.30 g tri-tert-butyl phosphine in 10 mL toluene were added. The reaction mixture was heated to reflux. After four hours, the heating was turn off, and the reaction was allowed to cool down to room temperature. The reaction mixture was filter through a Celite/silica gel plug. The product (4.1 g) was purified by flash chromatography initially using hexane, and 10% then up to 30% ethyl acetate in hexane.

Synthesis of 11

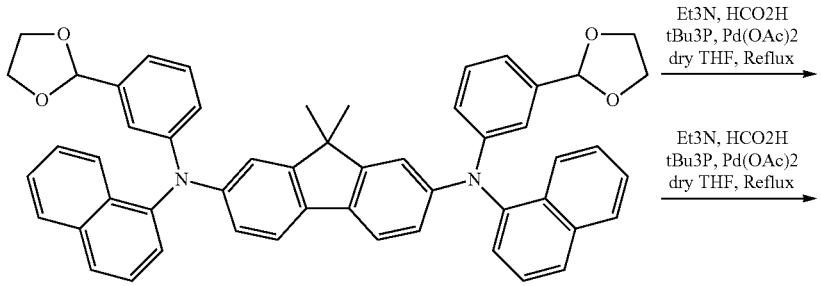

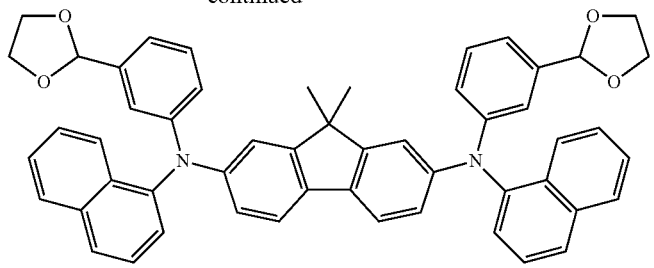

Dehalogenation of N2,N7-bis(3-(1,3-dioxolan-2-yl)phenyl)-9,9-dimethyl-N2,N7-di(naphthalen-1-yl)-9H-fluorene-2,7-diamine To a clean and dry round bottom flask under nitrogen, were added 8.0 g N2,N7-bis(3-(1,3-dioxolan-2-yl)phenyl)-9,9-dimethyl-N2,N7-di(naphthalen-1-yl)-9H-fluorene-2,7-diamine, 500 mL anhydrous THF, 14.43 mL triethylamine, and 3.91 mL formic acid. After the reaction mixture was degassed with strong nitrogen flow for 30 minutes, 0.232 g palladium (II) acetate and 0.314 g tri-tert-butyl phosphine in 5 mL toluene were added. After the reaction was heated to reflux overnight, the heat was removed and the reaction was allowed to cool down to room temperature. The reaction mixture was filter through a Celite/silica gel plug, and the solvent was removed by evaporator. The crude product was carried on second dehalogenation without further purification.

To a clean and dry round bottom flask under nitrogen, were added 8.0 g N2,N7-bis(3-(1,3-dioxolan-2-yl)phenyl)-9,9-dimethyl-N2,N7-di(naphthalen-1-yl)-9H-fluorene-2,7-diamine, 500 mL anhydrous THF, 14.43 mL triethylamine, and 3.91 mL formic acid. After the reaction mixture was degassed with strong nitrogen flow for 30 minutes, 0.232 g palladium (II) acetate and 0.314 g tri-tert-butyl phosphine in 5 mL toluene were added. After the reaction was heated to reflux overnight, the heat was removed and the reaction was allowed to cool down to room temperature. The reaction mixture was filter through a Celite/silica gel plug, and the solvent was removed by evaporator. The crude product was carried on second dehalogenation without further purification.

Synthesis of 12

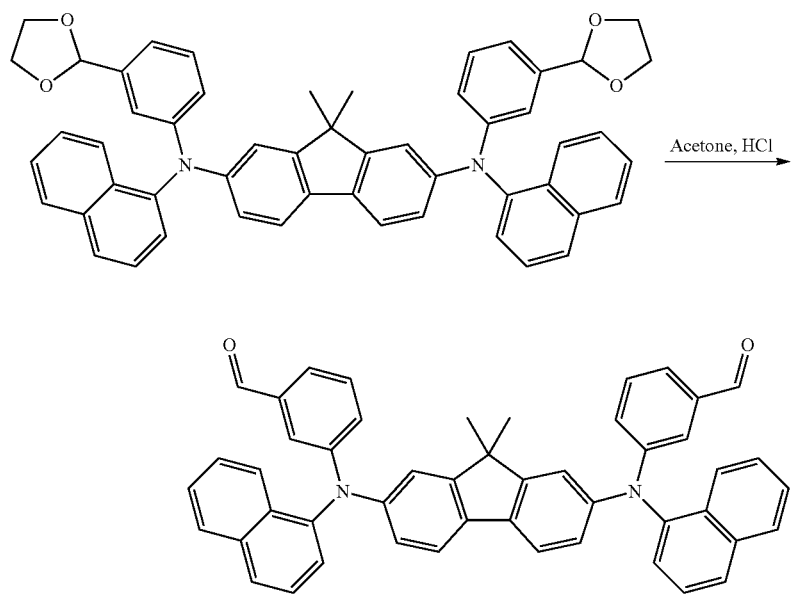

Synthesis of 3,3'-((9,9-dimethyl-9H-fluorene-2,7-diyl)bis(naphthalen-1-ylazanediyl))dibenzaldehyde To a three-neck round-bottom flask, were added 8.0 g N2,N7-bis(3-(1,3-dioxolan-2-yl)phenyl)-9,9-dimethyl-N2,N7-di(naphthalen-1-yl)-9H-fluorene-2,7-diamine and in 100 mL acetone. 41.1 mL 2 M hydrochloric acid solution was added slowly to the reaction mixture through an addition funnel. After TLC showed the reaction was done, the solvent was removed by evaporation. 200 mL Ethyl acetate was added, and the reaction mixture was extracted using DI water (4×200 mL). The organic layer was dried over sodium sulfate. After filtration, the solvent was removed by evaporation. The product (6.9 g) was obtained after drying under vacuum, and was carried on to next step without further purification. The structure was confirmed by NMR.

Synthesis of 13 (PLX-C)

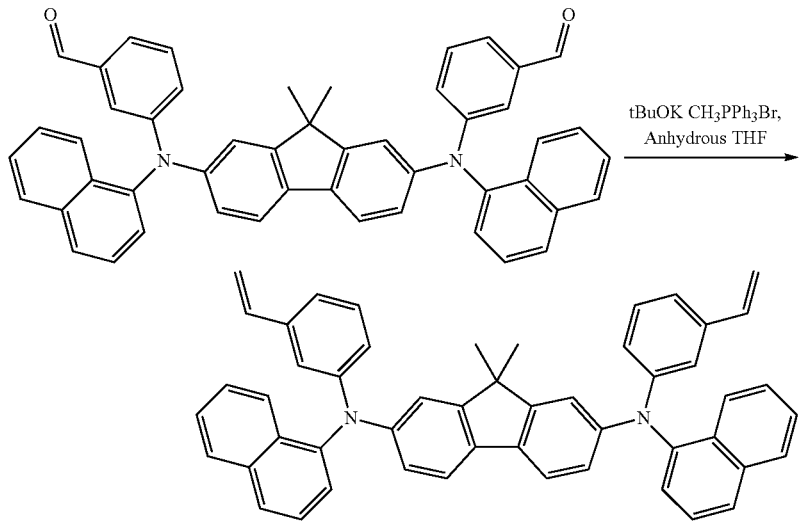

Synthesis of 9,9-dimethyl-N2,N7-di(naphthalen-1-yl)-N2,N7-bis(3-vinylphenyl)-9H-fluorene-2,7-diamine To an oven-dried three-neck round-bottom flask under nitrogen, were added 500 mL anhydrous THF, 3.51 g potassium tert-butoxide, and 10.80 g methyltriphenylphosphonium bromide. The mixture was stirred for 10 min. 6.9 g 3,3'-((9,9-dimethyl-9H-fluorene-2,7-diyl)bis(naphthalen-1-ylazanediyl))dibenzaldehyde in 250 mL anhydrous THF was added through an additional funnel dropwise to the reaction mixture over 30 min. The reaction solution was filtered through a Celite/silica gel plug, and solvent was removed by rotary evaporation. The product was first purified by flash chromatography using hexane and 1% ten 2% ethyl acetate in hexane. The structure was confirmed by NMR. The further purification was performed by dissolving the column pure solid in minimal amount of HPLC acetone and then precipitating in HPLC Methanol, giving final product (1.57 g). The structure was confirmed by NMR.

Example 4: Synthesis of PLX-B

Synthesis of 14

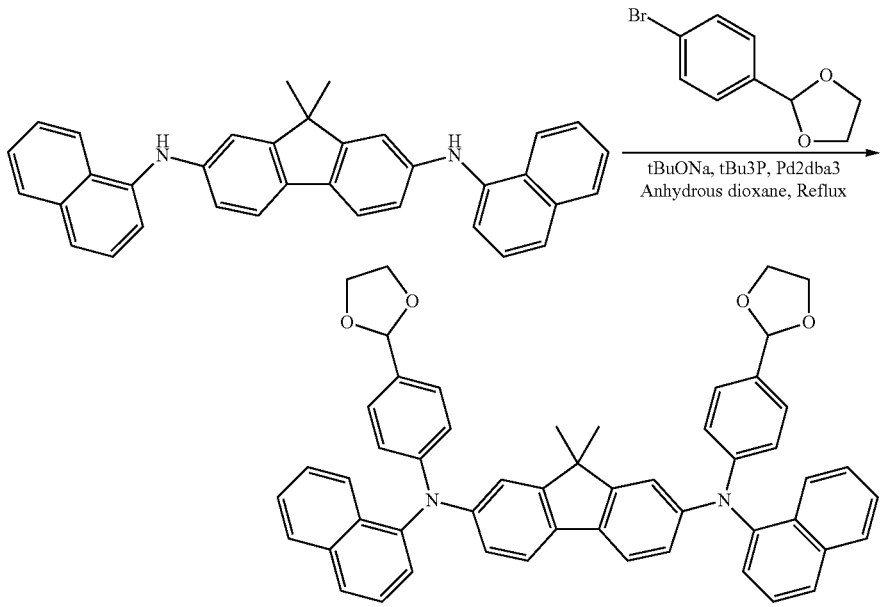

Synthesis of N2,N7-bis(4-(1,3-dioxolan-2-yl)phenyl)-9,9-dimethyl-N2,N7-di(naphthalen-1-yl)-9H-fluorene-2,7-diamine To an oven-dried three-neck round-bottom flask under nitrogen, were added 700 mL anhydrous dioxane, 5.0 g 9,9-dimethyl-N2,N7-di(naphthalen-1-yl)-9H-fluorene-2,7- diamine, and 4.8 mL of 2-(4-bromophenyl)1,3-dioxalane. After the reaction mixture was degassed with strong nitrogen flow for 30 minutes, 3.05 g sodium tert-butoxide, 0.38 g tris(dibenzylideneacetone)dipalladium(0) (Pd$_2$dba$_3$), and 0.26 g tri-tert-butyl phosphine in 10 mL toluene were added. The reaction mixture was heated to reflux. After four hours, the heating was turn off, and the reaction was allowed to cool down to room temperature. The reaction mixture was filtered through a Celite/silica gel plug. Purification by flash chromatography using hexane, and 5% then up to 30% ethyl acetate in hexane afforded product (3.0 g) with 3 spots on TLC plate. NMR shows that they were the product and deprotected aldehyde by-products. The following re-protected reaction was performed.

To an oven-dried three-neck round-bottom flask equipped with Dean-Stark under nitrogen, were added 250 mL toluene, 3.0 g column purified products, 4.6 mL of ethylene glycol, and 0.150 g of p-toluenesulfonic acid monohydrate. The reaction mixture was reflux, and the Dean Stark trap was drained as much as possible throughout the day but left full overnight. After there was only single spot on TLC plate, the heating was turn off, and the reaction was allowed to cool down to room temperature. The reaction mixture was extracted with DI water (4×200 mL), and the combined aqueous layer was extracted with methyl tert-butyl ether (2×200 mL). The combined organic layer was dried over sodium sulfate. Sodium sulfate was removed by filtration, and solvent was removed by evaporation. The crude product was dissolved in 20 mL acetone and precipitated into 500 mL MeOH. Solids was obtained by filtration and dried under vacuum, giving 2.42 g product. The structure was confirmed by NMR.

Synthesis of 15

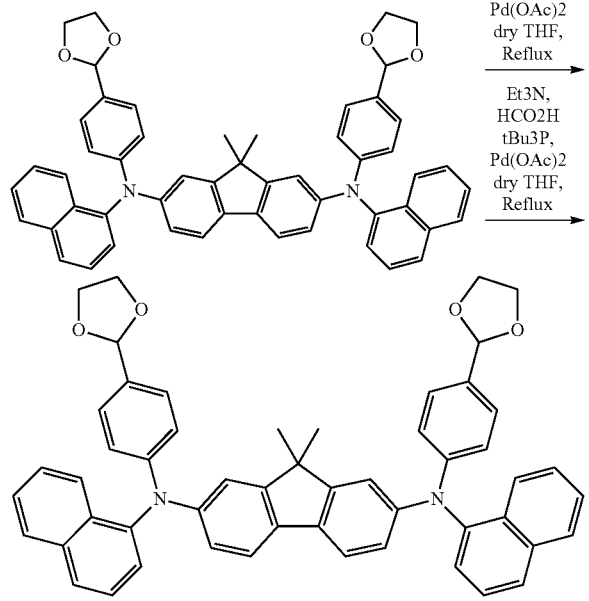

Dehalogenation of 9 N2,N7-bis(4-(1,3-dioxolan-2-yl)phenyl)-9,9-dimethyl-N2,N7-di(naphthalen-1-yl)-9H-fluorene-2,7-diamine To a clean and dry round bottom flask under nitrogen, were added 2.4 g N2,N7-bis(4-(1,3-dioxolan-2-yl)phenyl)-9,9-dimethyl-N2,N7-di(naphthalen-1-yl)-9H-fluorene-2,7-diamine, 250 mL anhydrous THF, 4.36 mL triethylamine, and 1.18 mL formic acid. After the reaction mixture was degassed with strong nitrogen flow for 30 minutes, 0.07 g palladium (II) acetate and 0.095 g tri-tert-butyl phosphine in 5 mL toluene were added. After the reaction was heated to reflux overnight, the heat was removed and the reaction was allowed to cool down to room temperature. The reaction mixture was filter through a Celite/silica gel plug, and the solvent was removed by evaporator. The crude product was carried on second dehalogenation without further purification.

To a clean and dry round bottom flask under nitrogen, were added 2.4 g N2,N7-bis(4-(1,3-dioxolan-2-yl)phenyl)-9,9-dimethyl-N2,N7-di(naphthalen-1-yl)-9H-fluorene-2,7-diamine, 250 mL anhydrous THF, 4.36 mL triethylamine, and 1.18 mL formic acid. After the reaction mixture was degassed with strong nitrogen flow for 30 minutes, 0.07 g palladium (II) acetate and 0.095 g tri-tert-butyl phosphine in 5 mL toluene. After the reaction was heated to reflux overnight, the heat was removed and the reaction was allowed to cool down to room temperature. The reaction mixture was filter through a Celite/silica gel plug, and the solvent was removed by evaporator. The crude product was carried on to next deprotection reaction without further purification.

Synthesis of 16

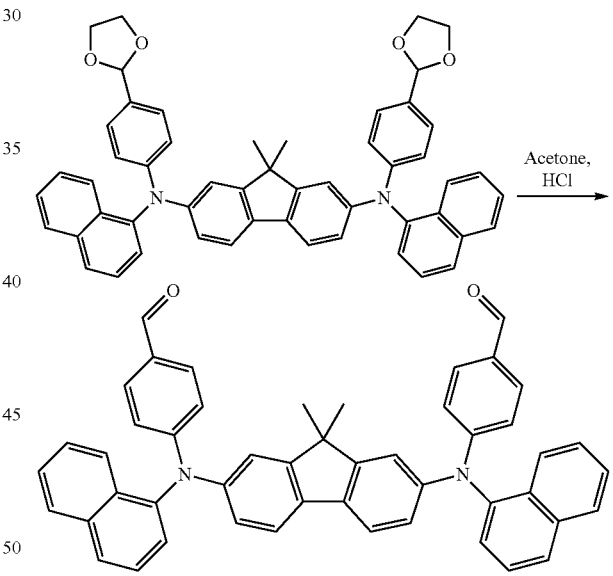

Synthesis of 4,4'-((9,9-dimethyl-9H-fluorene-2,7-diyl)bis(naphthalen-1-ylazanediyl))dibenzaldehyde To a three-neck round-bottom flask, were added 2.42 g N2,N7-bis(4-(1,3-dioxolan-2-yl)phenyl)-9,9-dimethyl-N2,N7-di(naphthalen-1-yl)-9H-fluorene-2,7-diamine and in 250 mL acetone. 20 mL 2 M hydrochloric acid solution was added slowly to the reaction mixture through an addition funnel. After TLC showed the reaction was done, the solvent was removed by evaporation. 400 mL Ethyl acetate was added, and the reaction mixture was extracted using DI water (4×200 mL). The organic layer was dried over sodium sulfate. After filtration, the solvent was removed by evaporation. The product (1.7 g) was purified by flash chromatography using hexane, and 5% and up to 15% ethyl acetate in hexane. The structure was confirmed by NMR.

Synthesis of 17 (PLX-B)

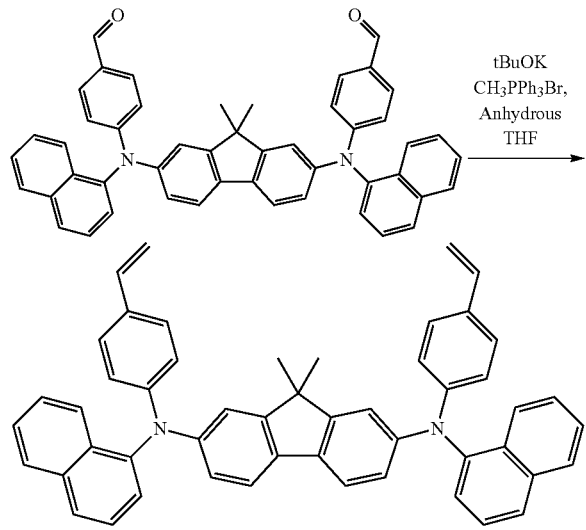

Synthesis of 9,9-dimethyl-N2,N7-di(naphthalen-1-yl)-N2,N7-bis(4-vinylphenyl)-9H-fluorene-2,7-diamine To an oven-dried three-neck round-bottom flask under nitrogen, were added 175 mL anhydrous THF, 0.91 g potassium tert-butoxide, and 2.78 g methyltriphenylphosphonium bromide. The mixture was stirred for 10 min. 1.7 g 4,4'-((9,9-dimethyl-9H-fluorene-2,7-diyl)bis(naphthalen-1-ylazanediyl))dibenzaldehyde in 125 mL anhydrous THF was added through an additional funnel dropwise to the reaction mixture over 30 min. The reaction solution was filtered through a Celite/silica gel plug, and solvent was removed by rotary evaporation. The product (0.95 g) was purified by flash chromatography using 100% hexane and then 1% ethyl acetate in hexane. The structure was confirmed by NMR.

Example 5

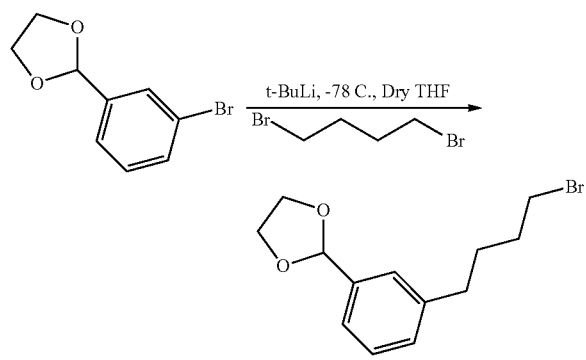

Synthesis of 2-(3-(4-bromobutyl)phenyl)-1,3-dioxolane

To a clean and dry 2000 ml round bottom flask equipped with a 500 ml addition funnel, low temperature thermometer and magnetic stir bar was transferred anhydrous tetrahydrofuran (800.0 ml) under nitrogen. 2-(3-bromophenyl)-1,3-dioxolane (33.0 ml, 0.2183 mol) was added to this flask by syringe. The reaction vessel was placed into a dry ice/acetone bath until a temperature of <−65° was achieved. The reaction mixture was then allowed to stir for 45 minutes at a stirring speed of 550 rpm in order to verify the integrity of the stirring apparatus at this temperature. Tert-butyllithium solution (257.0 ml, 0.4690 mol) was transferred to the addition funnel by cannula, then added dropwise to the reaction never allowing the temperature to rise above −65° C. Following addition, the reaction was allowed to stir for a period of 30 minutes. The vessel was then removed from the dry ice/acetone bath and allowed to warm to a temperature of −20° C. The vessel was then again placed into the dry ice/acetone bath until a temperature of <−65° was achieved. 1,4-dibromobutane (103.5 ml, 0.8740 mol) was added to the reaction dropwise via syringe, maintaining the current temperature. The reaction was allowed to stir for 30 minutes at this temperature following addition. The reaction was slowly warmed to room temperature over the following 12 hours. After warming, the reaction was quenched by the addition of isopropanol (20.0 ml) via syringe.

After quenching, solvent was removed by rotary evaporation using a maximum temperature of 70° C. Methyl tert-butyl ether (700.0 ml) was added and the solution was washed with deionized water (200.0 ml×8). The organic fraction was collected and dried over anhydrous sodium sulfate. Solids were then removed by vacuum filtration over a bed of Celite. Solvent was removed by rotary evaporation using a maximum temperature of 70° C. The crude product was then purified by vacuum distillation at 100° C. for 4 hours to remove most of 1,4-dibromobutane. Further purification was carried out by automatic flash column chromatography on silica gel using 3% ethyl acetate/97% hexane as an eluent. This provided pure product confirmed by NMR and GC-MS.

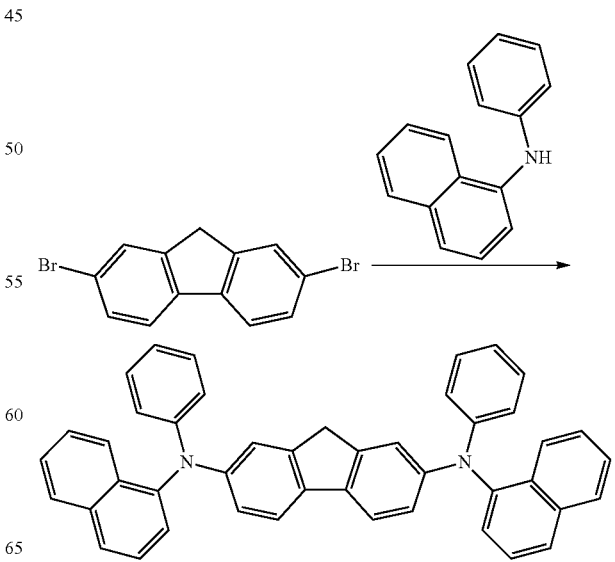

Synthesis of N2,N7-di(naphthalen-1-yl)-N2,N7-diphenyl-9H-fluorene-2,7-diamine

To a 2-liter three-neck round bottom flask was added anhydrous toluene (1000 mL) by cannula. 2,7-dibromofluorene (50.0 g) was added to this flask, then stirred until all dissolved. N-phenyl-1-naphthylamine (81.14 g) was then added. The reaction vessel was purged with a strong nitrogen flow for 30 minutes, followed by the addition of sodium tert-butoxide (44.5 g) by funnel. Tris(dibenzylideneacetone)dipalladium(0) (5.65 g) was added to the reaction. Tri-tert-butyl phosphine (3.75 g) in anhydrous toluene (20 mL) was added via syringe. The reaction was heated to reflux for 2 hours and reaction completion was confirmed by thin-layer chromatography. The vessel was removed from heat and allowed to cool to room temperature. The reaction solution was filtered through a celite/silica gel plug and solvent was then removed by rotary evaporation. The crude material was initially purified by flash chromatography, followed by sublimation to yield NMR pure product.

equipment was removed from the inert atmosphere glovebox. Attached a mineral oil bubbler to the reaction flask. The reaction vessel was then placed into a cool water bath. The N2,N7-di(naphthalen-1-yl)-N2,N7-diphenyl-9H-fluorene-2,7-diamine/anhydrous DMF solution was then added to the reaction slowly dropwise via syringe. The reaction was allowed to stir in the water bath for 30 minutes. The vessel was then removed from the bath and allowed to stir at room temperature for an additional 30 minutes. A solution of 2-(3-(4-bromobutyl)phenyl)-1,3-dioxolane (5.71 g) in anhydrous DMF (15 mL) was then prepared and added to the reaction dropwise via syringe. The reaction was allowed to stir at room temperature for 1 hour, then placed into an oil bath of 80 C for an additional 1 hour. Reaction completion was confirmed by thin-layer chromatography and was removed from heat. The reaction was quenched by slowly adding, portion-wise, to slightly iced DI water (400 mL) with vigorous stirring. Ethyl acetate (100 mL) was then added to this flask and stirred for 15 minutes. This mixture was poured into a 2-liter separatory funnel and another

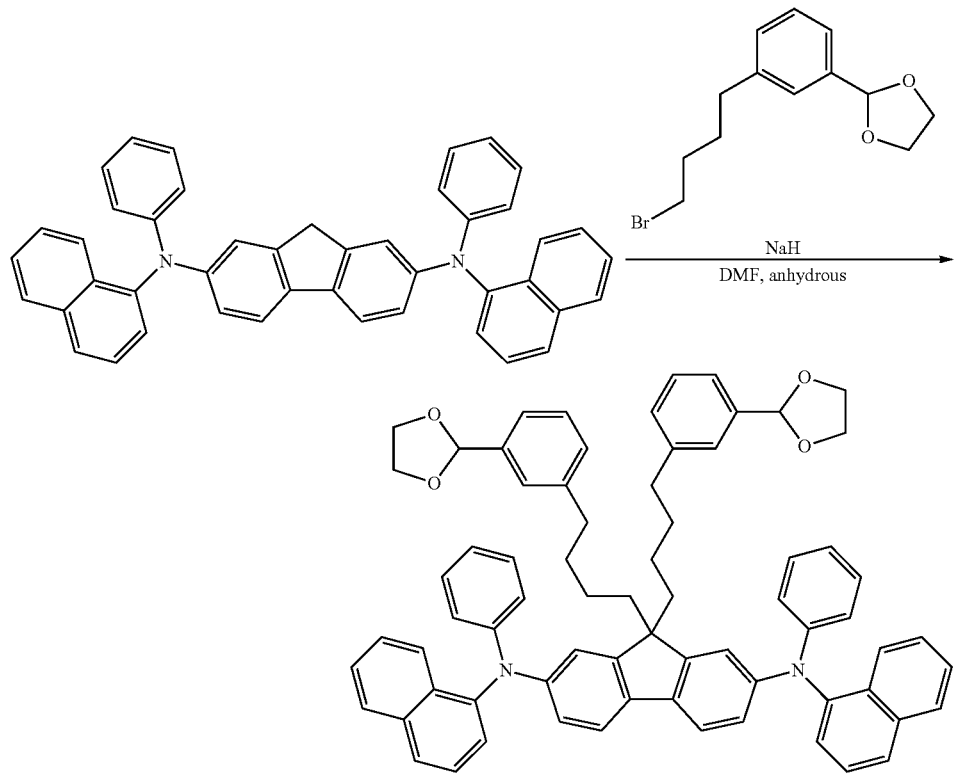

Synthesis of 9,9-bis(4-(3-(1,3-dioxolan-2-yl)phenyl)butyl)-N2,N7-di(naphthalen-1-yl)-N2,N7-diphenyl-9H-fluorene-2,7-diamine A 1-liter three-neck round bottom flask equipped with a magnetic stir bar, high-temperature thermometer, and addition funnel was placed into an inert atmosphere glovebox. This flask was charged with sodium hydride (0.63 g) and sealed with rubber septa. A solution of N2,N7-di(naphthalen-1-yl)-N2,N7-diphenyl-9H-fluorene-2,7-diamine (5.00 g) in anhydrous N,N-dimethylformamide (DMF) (125 mL) was prepared in an inert atmosphere. At this point, all portion of ethyl acetate (100 mL) was added. The aqueous phase was extracted again with ethyl acetate (350 mL) and all the organic fractions were combined and washed with DI water (3×350 mL). The resulting organic fraction was dried with anhydrous sodium sulfate, and the solids were removed by gravity filtration. Silica gel was added to the resulting dry solution and solvent was removed by rotary evaporation leaving the crude material adsorbed to silica. Flash chromatography was carried out using ethyl acetate/hexane as a solvent system. Further purification by precipitation from a minimum amount of acetone into cold methanol (2×950 mL) yielded NMR pure product.

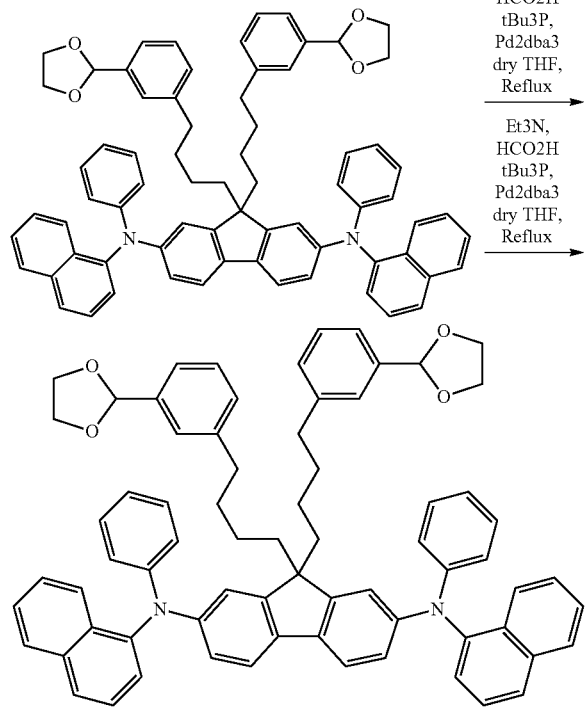

First dehalogenation of 9,9-bis(4-(3-(1,3-dioxolan-2-yl)phenyl)butyl)-N2,N7-di(naphthalen-1-yl)-N2,N7-diphenyl-9H-fluorene-2,7-diamine A 1-liter three-neck round bottom flask was charged with 9,9-bis(4-(3-(1,3-dioxolan-2-yl)phenyl)butyl)-N2,N7-di(naphthalen-1-yl)-N2,N7-diphenyl-9H-fluorene-2,7-diamine (12.3 g). Anhydrous tetrahydrofuran (THF) (500 mL) was then added to this flask. Triethylamine (17.0 mL) and formic acid (4.6 mL) were then added to the reaction via syringe. The reaction vessel was purged with a strong nitrogen flow for 30 minutes. Palladium (II) acetate (0.27 g) was added to the reaction. Tri-tert-butyl phosphine (0.36 g) in anhydrous toluene (10 mL) was then added by syringe and the reaction was heated to reflux. After 2 hours, the reaction was removed from heat and allowed to cool to room temperature. The reaction solution was filtered through a celite and silica gel plug. Solvent was removed by rotary evaporation.

Second dehalogenation of 9,9-bis(4-(3-(1,3-dioxolan-2-yl)phenyl)butyl)-N2,N7-di(naphthalen-1-yl)-N2,N7-diphenyl-9H-fluorene-2,7-diamine A 1-liter three-neck round bottom flask was charged with 9,9-bis(4-(3-(1,3-dioxolan-2-yl)phenyl)butyl)-N2,N7-di(naphthalen-1-yl)-N2,N7-diphenyl-9H-fluorene-2,7-diamine (12.3 g). Anhydrous tetrahydrofuran (THF) (500 mL) was then added to this flask. Triethylamine (17.0 mL) and formic acid (4.6 mL) were then added to the reaction via syringe. The reaction vessel was purged with a strong nitrogen flow for 30 minutes. Palladium (II) acetate (0.27 g) was added to the reaction. Tri-tert-butyl phosphine (0.36 g) in anhydrous toluene (10 mL) was then added by syringe and the reaction was heated to reflux. After 2 hours, the reaction was removed from heat and allowed to cool to room temperature. The reaction solution was filtered through a celite and silica gel plug. Solvent was removed by rotary evaporation.

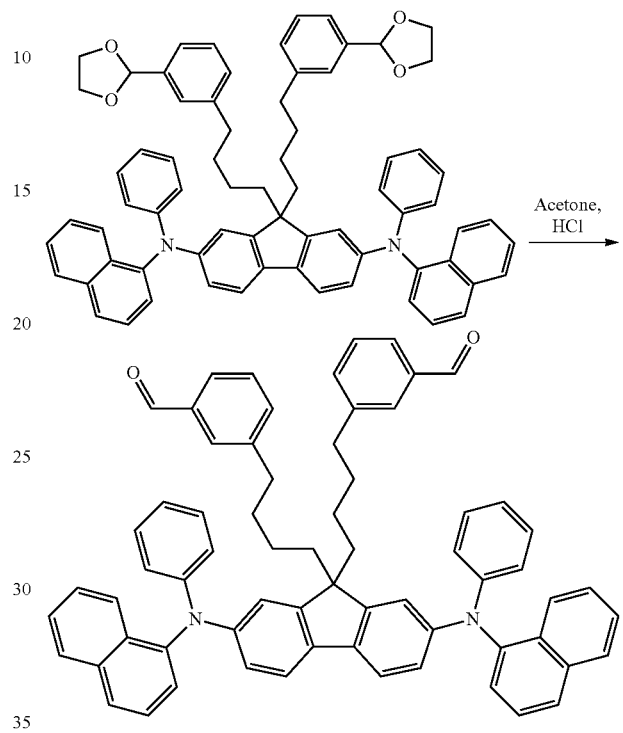

Synthesis of 3,3'-((2,7-bis(naphthalen-1-yl(phenyl)amino)-9H-fluorene-9,9-diyl)bis(butane-4,1-diyl))dibenzaldehyde To 1-liter three-neck round bottom flask equipped with a magnetic stir bar and an addition funnel was transferred a solution of 9,9-bis(4-(3-(1,3-dioxolan-2-yl)phenyl)butyl)-N2,N7-di(naphthalen-1-yl)-N2,N7-diphenyl-9H-fluorene-2,7-diamine (12.3 g) in acetone (500 mL). Hydrochloric acid solution (61.0 mL, 2.0M) was transferred to the addition funnel atop the reaction flask by syringe. The acid solution was added to the reaction dropwise with vigorous stirring. The reaction was allowed to stir for an additional 30 minutes following the addition of acid. Reaction completion was confirmed by thin-layer chromatography and solvent was removed by rotary evaporation. Ethyl acetate (750 mL) was added to the resulting mixture and this solution was washed with DI water (5×200 mL). The organic fraction was collected and dried over anhydrous magnesium sulfate. Solids were removed by gravity filtration. Silica gel was added to the solution and solvent was removed by rotary evaporation leaving the crude material adsorbed to silica. Crude product was initially purified by flash column chromatography using ethyl acetate/hexane as an eluent. The resulting material was dissolved in a minimum amount of acetone and precipitated into cold methanol (3×750 mL). The solids collected by vacuum filtration were dried and determined to be pure product by NMR.

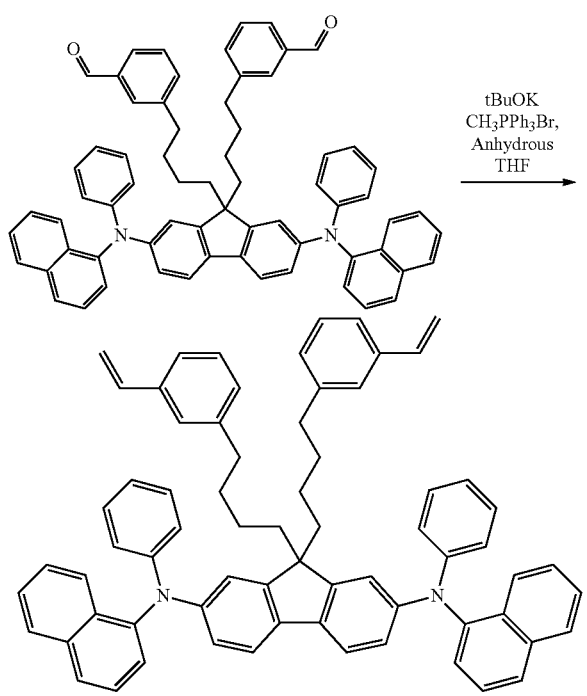

Synthesis of N2,N7-di(naphthalen-1-yl)-N2,N7-diphenyl-9,9-bis(4-(3-vinylphenyl)butyl)-9H-fluorene-2,7-diamine To a 1-liter three-neck round-bottom flask under nitrogen, were added anhydrous THF (400 mL), sodium tert-butoxide (2.69 g), methyltriphenylphosphonium bromide (8.28 g). The reaction mixture was allowed to stir for 10 min. Then 3,3'-((2,7-bis(naphthalen-1-yl(phenyl)amino)-9H-fluorene-9,9-diyl)bis(butane-4,1-diyl))dibenzaldehyde (7.12 g) in anhydrous THF (15 mL) was added dropwise through an additional funnel. After 30 min, the reaction mixture was filtered through a Celite/Silica gel plug. The solvent was removed by evaporation. Purification by flash chromatography (1-3% ethyl acetate in hexane) afforded 6.8 g NMR pure product. The product was dissolved in HPLC grade acetone, and precipitation in MeOH gave final product (6.32 g).

Example 6: Ink Formulation

Inks were formulated with a series of organic solvents used in lab cell device fabrication including toluene, chlorobenzene, and o-xylene. Anhydrous solvent was purged with argon overnight to remove any residual oxygen present in the solvent; the purged solvent was then used for the formulation of the HTL ink. All the inks were formulated in the glove box under nitrogen environment and stored in amber vials and any exposure from light is avoided to prevent any kind of photo-degradation and photo-oxidation.

To formulate an ink called PLX-A, HTL materials PLX-D and PLX-I were blended in the ratio 70:30 by weight and dissolved in toluene at 1 wt/wt % total solid content. Both molecules were weighed and mixed in a vial, and the purged solvent was added thereafter. No heating was required to dissolve the materials in the ink.

To formulate Ink B (below), materials PLX-D and PLX-B were blended in a 90:10 by weight ratio and dissolved in toluene at 1 wt/wt % total solids content.

To formulate Ink C (below), materials PLX-L and PLX-B were blended in a 50:50 by weight ratio and dissolved in toluene at 1 wt/wt % total solids content.

Example 7: Film Formation

An ink called PLX-N was prepared from PLX-D by thermally polymerizing in solution. A concentrated solution of the monomer was made at 30% wt. total solids in oxygen-free argon-purged toluene. The monomer solution and stirbar were charged to a cleaned pressure reactor. The reaction was heated in a sandbath at 150-155° C. in a nitrogen glovebox. Heated reaction for 13 hours at which time a gel had formed. Reaction was cooled and diluted to 1% total solids heated back to 80° C. to dissolve all solids. This solution was then filtered through a 1 um glass filter to provide a 0.32% total solids ink.

To study the film properties of aforementioned inks such as PLX-A, the ink was pre-filtered using a 0.45 um PTFE filter and then dispensed onto the substrate and spin coated on top of a hole injection layer.

Film Studies

The HOMO of PLX-A is −5.28 eV, and has about 100% film retain after toluene wash.

The HOMO of Ink B is −5.36 eV, and has about 100% film retain after toluene wash.

The HOMO of Ink C is −5.38 eV, and has about 100% film retain after toluene wash.

HTL Characterization (PLX-A)

| Parameter | Units | Value/Assessment |
| --- | --- | --- |
| HOMO (from AC2) | eV | 5.28 |
| LUMO (calculation) | eV | 2.04 |
| Band Gap (from absorption spectrum) | eV | 3.24 |
| Film Solvent Resistance to Toluene | % thickness change | About zero (about 100% film retained) |
| Viscosity | cP | 0.67 cP @ 25° C. |

Example 8: Optical Microscopy and Film Quality

For PLX-A, the optical microscopy images at 500× shows good film quality (FIG. 1), and the Root mean square roughness from AFM was 0.24 nm.

Figure 2:
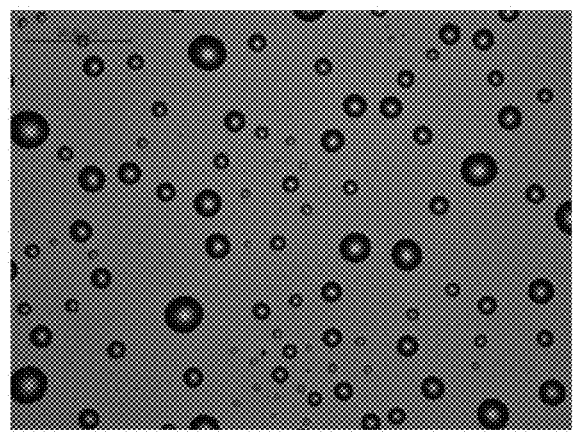
FIG. 2 illustrates one embodiment for an initial film formation on non-aqueous HIL (500×).

In contrast, when annealing small molecule HTL materials PLX-A on top of NQ (NQ is non-aqueous) based HILs, beading up of the films was observed (FIG. 2).

While not being limited by theory, the problem may be dependent on the Tg and lower molecular weight.

Example 9: Prepolymerization

The molecular weight of the material was increased via carrying out a prepolymerization reaction to offset the Tg and reduce the rate of aggregate/bead formation. The prepolymerization was carried out via three different approaches:

1) Thermal Pre Crosslinking

Figure 3:
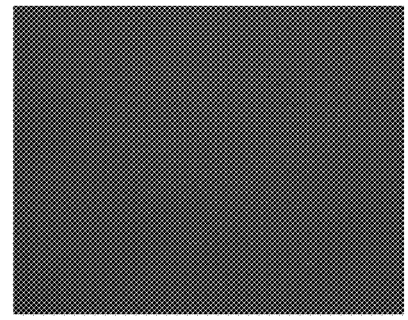
FIG. 3 illustrates one embodiment for pre-polymer by cross-linking reaction of PLX-D (500×), with film annealing 200° C.

The HTL, PLX-D, was dissolved in oxygen-free argon-purged toluene at higher concentrations (30 wt/wt %) and then heated in a pressure reactor in a sand bath placed in a glove box to 150-155° C. until a gel was formed. This gel was then redissolved in toluene to achieve the target concentration. With the increase in the molecular weight the beading up issue was successfully resolved as shown in the micrograph of FIG. 3.

2) UV Precrosslinking on Ink

Figure 4:
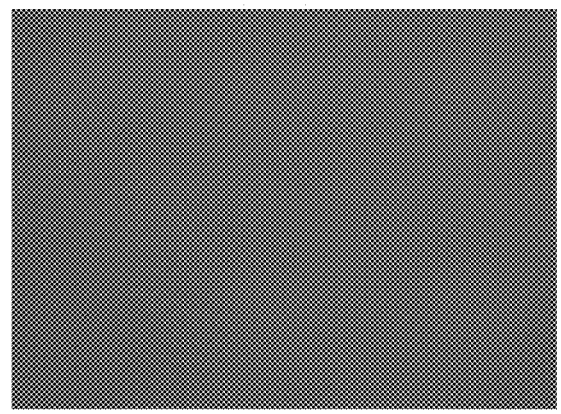
FIG. 4 illustrates an embodiment for UV-Modified ink (500×).

HTL compound W (structure above) was dissolved in oxygen free toluene to formulate the ink. After HTL ink was prepared, the ink was exposed to UV light for partially cross-linking. After the UV exposure, the ink thickened and was diluted back to the target ink concentration to achieve the required film thickness. Then the ink was spun and annealed at 200° C. The optical microscopy at 500× image showed good film quality (FIG. 4). The same experiment was also tried with blends of Compound W and PLX-D yielding similar results.

3) UV Precrosslinking on Film

Figure 5:
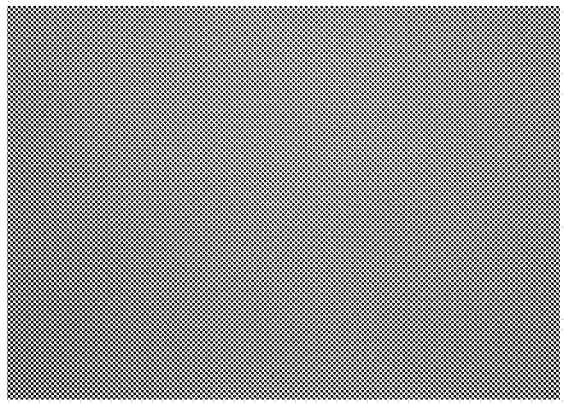
FIG. 5 illustrates an additional embodiment for a modified crosslinking process (500×).

HTL PLX-D was dissolved in oxygen free toluene to formulate the ink. After the HTL ink was spun on HIL, the film was annealed under UV and then under thermal (200° C.) annealing. The optical microscopy at 500× image shows good film quality (FIG. 5).

Example 10: Meta Versus Para, PLX-B vs PLX-C

Figure 6:
FIG. 6 illustrates an additional embodiment for PLX-C (500×), film annealed at 200° C.
Figure 7:
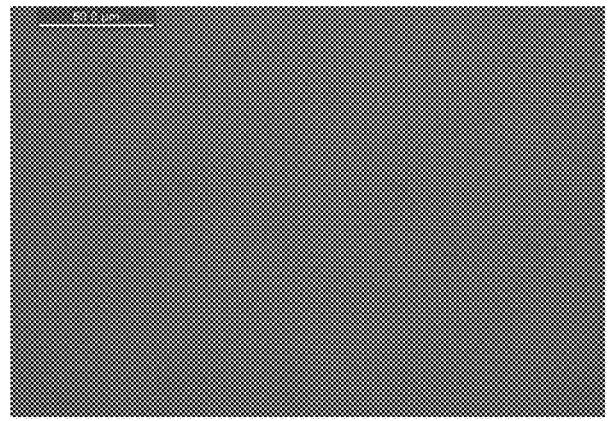
FIG. 7 illustrates an additional embodiment for PLX-B (500×), film annealed at 200° C.

To investigate the reaction rates, i.e rate of crystallization (affinity for the molecule to aggregate) as compared to the rate of crosslinking, and impact on morphology, film studies were carried out with PLX-C and PLX-B. The impact of meta versus para substitution was investigated. PLX-C (para) performed not as well as PLX-B (meta) (see FIGS. 6 and 7, respectively). Different substitution gave very different film formation.

Example 11: Lifetime Testing

Figure 8:
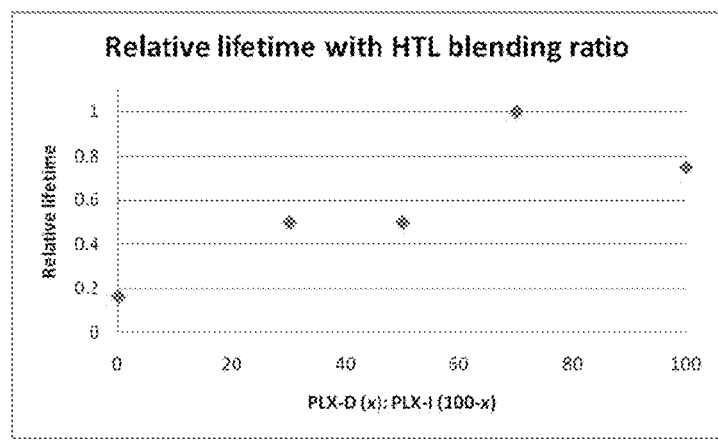
FIG. 8 illustrates relative lifetime with HTL blending ratio, for several embodiments.
Figure 9:
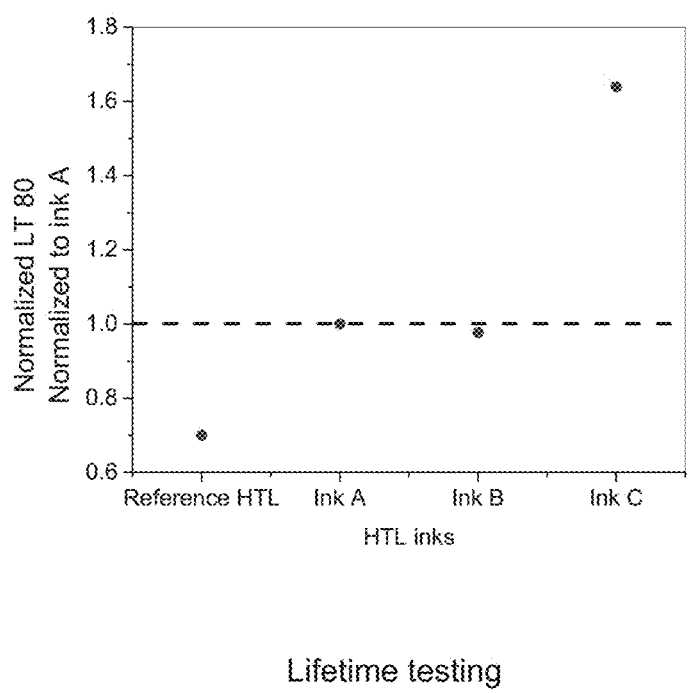
FIG. 9 illustrates relative lifetime with HTL for several ink formulations.

Compositions were prepared comprising mixtures of PLX-D and PLX-I. The weight ratio of the two components was varied to determine impact on lifetime testing (see FIG. 8). The current formulation was selected based on screening of HTL ink formulation in PHOLED devices, the relative lifetime performance of the different blends is shown in Table 2 and FIG. 9. (Accelerated LT80 testing: time required for the device to degrade to 80% of its luminance value). The reference HTL on this scale is at 0.7. The 70:30 ratio provided the best lifetime for the device in this study.

TABLE 2

| Inks* | Annealing T (° C.) | Film Formation |
|---|---|---|
| INK A | 250 | AQ |
| INK B | 200 | AQ/NQ |
| INK C | 200 | AQ/NQ |

*Structures described further below

In Table 2, Ink A comprises:

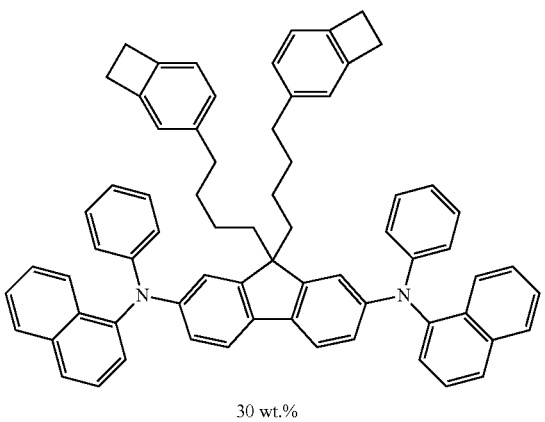

30 wt.%

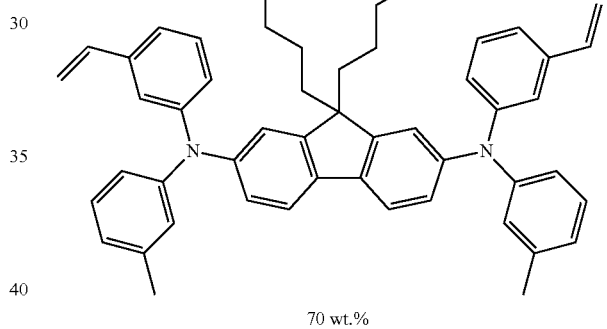

70 wt.%

Ink B comprises:

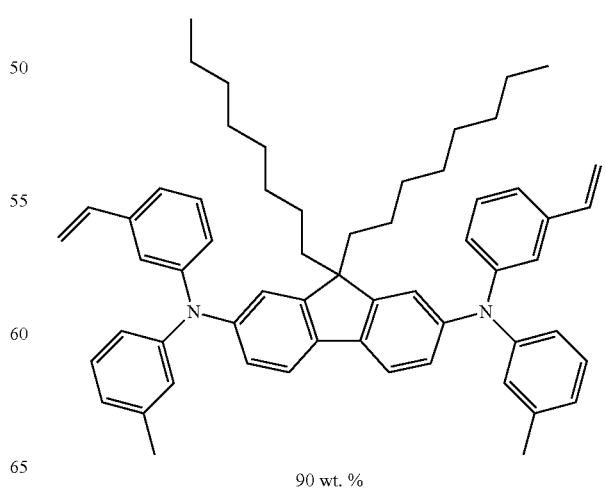

90 wt. %

93

-continued

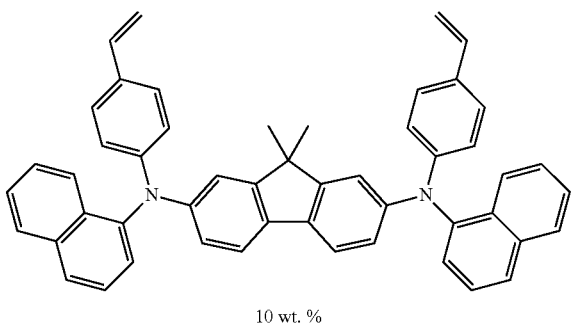

10 wt. %

Ink C comprises:

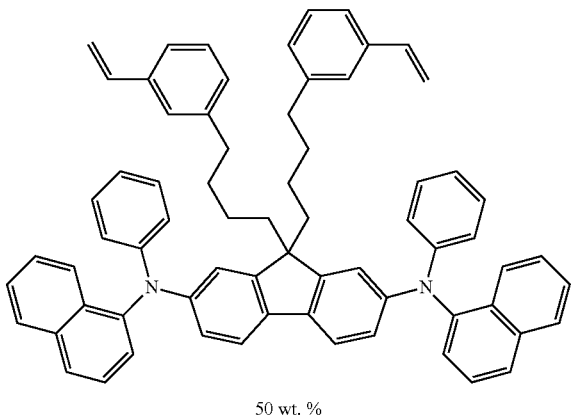

50 wt. %

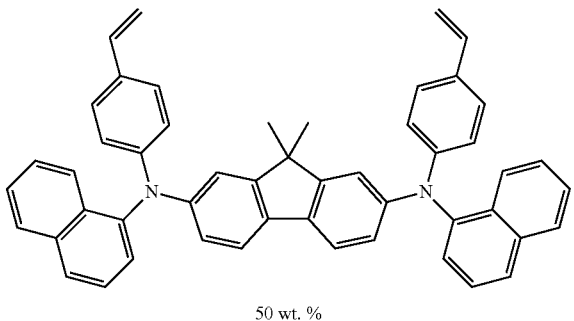

50 wt. %

Example 12: Stability Testing as Measured by TLC

The relative stability of compounds PLX-D and PLX-I was measured by TLC measurements. Solid samples were store in a glovebox in amber vials for six weeks (compound PLX-D) and seven weeks (PLX-I). A TLC single spot indicated there was only product, with no decomposition. If there were multiple spots, it indicated there was decomposition. Compound PLX-D showed two spots (less stability). Compound PLX-I showed one spot (more stability).

94

Additional Syntheses:

Example 13: Synthesis of Core

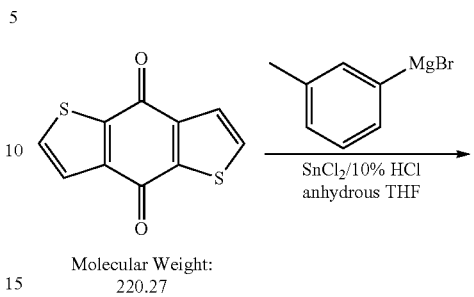

Molecular Weight: 220.27

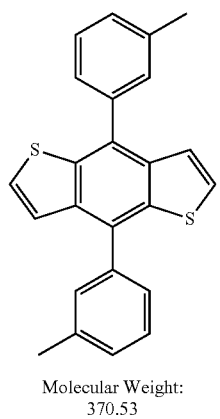

Molecular Weight: 370.53

Synthesis of 4,8-di-m-tolylbenzo[1,2-b:4,5-b']dithiophene

A clean and dry 2000 ml round bottom flask equipped with reflux condenser, magnetic stir bar, and thermometer with adapter was prepared, purged, and then charged with 4,8-dihydrobenzo[1,2-b:4,5-b']dithiophen-4,8-dione (7.34 g, 0.0333 mol). Anhydrous tetrahydrofuran (900.0 ml) was then added to this flask by cannula and stirring was initiated. Heat was applied to the reaction vessel to dissolve this material. The reaction vessel was placed into a water bath and m-tolylmagnesium bromide solution (100 ml, 0.1000 mol) was added via cannula. Following addition, the vessel was removed from the water bath and heated to reflux for 1 hour. The reaction was then removed from heat and allowed to cool to room temperature. m-tolylmagnesium bromide solution (100 ml, 0.1000 mol) was added via cannula and the reaction was again heated to reflux for 1 hour. The progress of the reaction was monitored by GC-MS and no starting material was present. The reaction was subsequently removed from heat and cool to room temperature overnight. A hydrochloric acid (160.0 ml, 10%)/tin (II) chloride (30.05 g, 0.1333 mol) solution was then prepared and added to the reaction via syringe. The reaction vessel was again heated to reflux for 1 hour, then removed from heat and allowed to cool to room temperature. Solvent was removed by rotary evaporation. Ethyl acetate (500.0 ml) was and the crude mixture was nearly dissolved. The volume was washed once with DI $H_2O$ (500 mL), and the organic layer containing solids was collected. Solids were removed by vacuum filtration, collected, and washed in hot methanol. The filtrate was dried over anhydrous magnesium sulfate, filtered, and removed of solvent by rotary evaporation. To the remaining crude material acetone (25.0 ml) and methanol (500.0 ml) were added and heated to reflux in trituration for 1 hour. The resulting solids in solution were vacuum-filtered and collected. All solids collected during purification were proved to be pure by NMR spectroscopy.

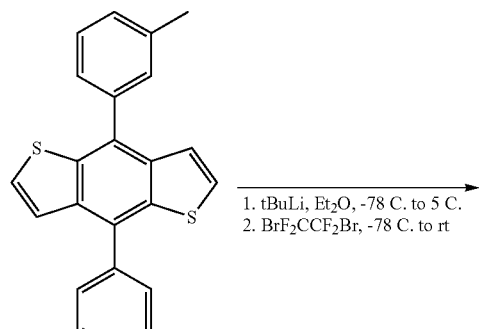

Molecular Weight: 370.53

1. tBuLi, Et₂O, -78 C. to 5 C.
2. BrF₂CCF₂Br, -78 C. to rt

Molecular Weight: 528.32

Synthesis of 2,6-dibromo-4,8-di-m-tolylbenzo[1,2-b:4,5-b']dithiophene

A 1000 ml round bottom flask equipped with an addition funnel, magnetic stir bar, and low-temperature thermometer with adapter was charged with 4,8-di-m-tolylbenzo[1,2-b:4,5-b']dithiophene (TH-1-180, 4.50 g, 0.0121 mol). Anhydrous tetrahydrofuran (300.0 ml) was then added to this flask via cannula while stirring. It is important to note that the solubility of this starting material is very poor in tetrahydrofuran. The reaction vessel was heated by heat gun, with vigorous stirring until all 4,8-di-m-tolylbenzo[1,2-b:4,5-b'] dithiophene dissolved. The reaction was placed into a dry ice/acetone bath until a temperature of less than −70° C. was achieved. Tert-butyllithium solution (19.5 ml, 0.0330 mol) was transferred to the addition funnel by syringe and added to the reaction dropwise. The temperature was monitored as not to allow it to warm to greater than −68° C. Following addition, the reaction was allowed to stir for 30 minutes at this temperature. The reaction was removed from the dry ice/acetone bath and allowed to warm to a temperature of above 5° C. The reaction was again placed into a dry ice/acetone bath until a temperature of less than −70° C. was reached. Dibromotetrafluoroethane (12.6 g, 0.0486 mol) was added to the reaction dropwise via syringe, and allowed to stir for 30 minutes. The reaction vessel was removed from the dry ice/acetone bath and allowed to warm to room temperature slowly over the weekend. TLC was used to confirm reaction completion. The reaction was then quenched by the addition of DI H₂O (20.0 ml) via syringe. Solvent was removed by rotary evaporation. The resulting crude material was dissolved in hot chloroform (500.0 ml) and washed with DI H₂O (1×300.0 ml). The organic fraction was collected and dried over anhydrous magnesium sulfate. Solids were removed by filtration and solvent by rotary evaporation. A solution of 1:1 methanol/DI H₂O (300.0 ml) was added to the crude product and heated to reflux in trituration for 45 minutes. The flask was allowed to cool, and the solids were vacuum filtered. Methanol (250.0 ml) was added to the crude solids and again heated to reflux in trituration with vigorous stirring for 1 hour. The solids were vacuum filtered from the hot methanol solution and dried under vacuum. This resulted in pure product confirmed by GC-MS and NMR.

Example 14: Synthesis of Core

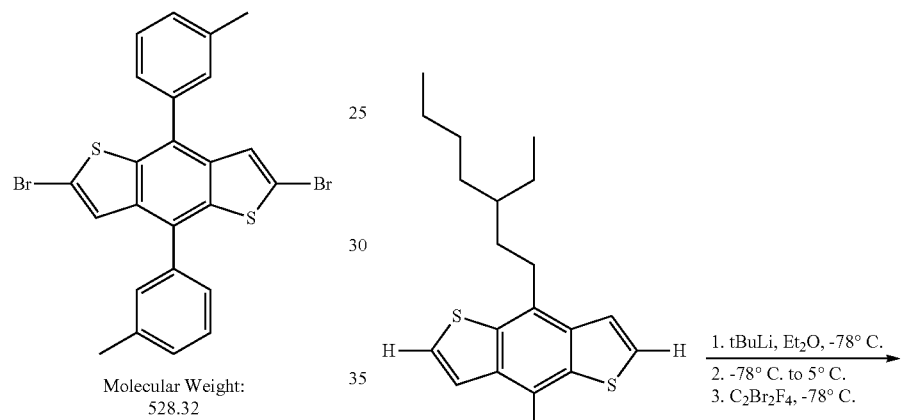

1. tBuLi, Et₂O, -78° C.
2. -78° C. to 5° C.
3. C₂Br₂F₄, -78° C.

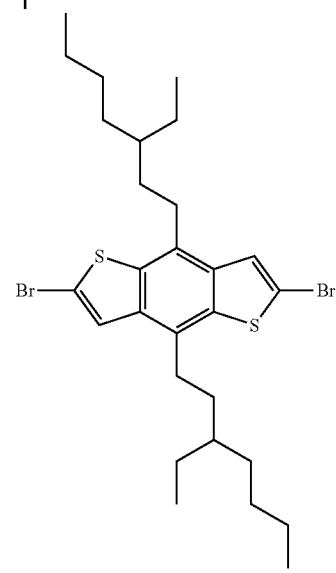

Synthesis of 2,6-dibromo-4,8-bis(3-ethylheptyl)benzo[1,2-b:4,5-b']dithiophene

A dry three-neck flask was flushed with nitrogen and was charged with 4,8-bis(3-ethylheptyl)benzo[1,2-b:4,5-b']dithiophene (30.7 g, 0.0693 mol) and diethyl ether (Et$_2$O) (700 mL, 0.1 M) via cannula. The reaction flask was cooled to −78° C. and a 1.3 M solution of tert-butyllithium in hexanes (144 mL, 0.187 mol) was added dropwise via deoxygenated syringe. After 30 minutes of stirring at −78° C., the solution was warmed up to 5° C. and stirring was continued for 5 minutes, at which point the reaction mixture was chilled back to −78° C. Dibromotetrafluoroethane (33 mL, 0.277 mol) was added to the reaction flask dropwise and stirring continued for 1 hours at −78° C. The cooling bath was removed and the reaction mixture was allowed to warm to ambient temperature. As the reaction was completed, cool DI water (20 mL) was slowly added to the reaction flask. Then, the reaction mixture was poured into cool DI water and extracted with methyl tert-butyl ether three times. The combined organic layer was washed with water two times and dried over anhydrous magnesium sulfate (MgSO$_4$). After the product was filtered, the solvent was removed by rotary evaporation. The crude product was dissolved in tetrahydrofuran and precipitated into cold methanol. The precipitate was obtained by filtration to yield pure product. Additional amounts of product can be recovered from concentrating down the methanol/tetrahydrofuran filtrate.

Example 15: Core Synthesis

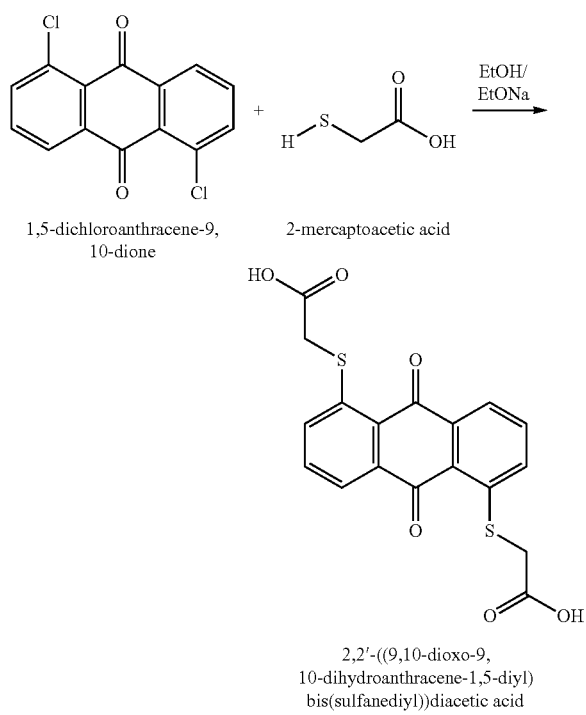

Synthesis of 2,2'-((9,10-dioxo-9,10-dihydroanthracene-1,5-diyl)bis(sulfanediyl)diacetic acid Anhydrous ethanol (2000.0 ml) was added to a 5000 ml three-neck round bottom flask equipped with a reflux condenser, mechanical stirrer, and a thermometer with adapter. Sodium (24 g, 1.0439 mol) was slowly added in small pieces over a 1.5 to 2 hour period. Then, 1,5-dichloroanthracene-9,10-dione (45.6 g, 0.1646 mol), 2-mercaptoacetic acid (25.6 ml, 0.3668 mol), manganese dioxide (8 g, 0.0920 mol), and 15-crown-5 (0.8 g, 0.0036 mol) were added into the reaction. The mixture was heated under nitrogen at 70° C. for 10 hours. After cooling to room temperature, DI H$_2$O (1500 ml) was added to the suspension while stirring. The resulting solution was filtered and 2.0 N HCl was added to the filtrate to generate a yellow precipitate. The yellow solid was collected by centrifuge, washed with DI H$_2$O three times and then dried in the oven to give 54 g of product (84% yield).

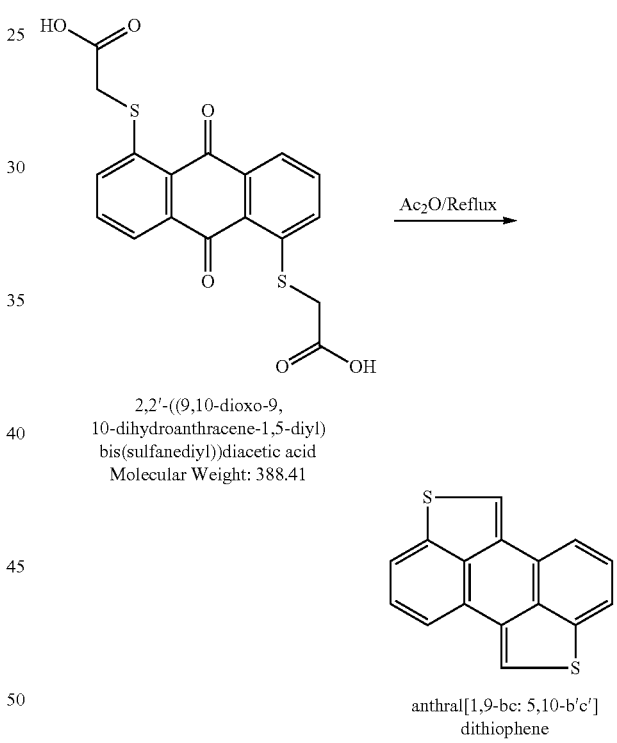

Synthesis of anthra[1,9-bc:5,10-b']dithiophene

Finely ground 2,2'-((9,10-dioxo-9,10-dihydroanthracene-1,5-diyl)bis(sulfanediyl))diacetic acid (120 g, 0.3090 mol) was slowly added to dry acetic anhydride (1800 ml) in a 3000 ml three-neck round bottom flask equipped with a reflux condenser. The reaction was refluxed for 4 hours under nitrogen until the evolving fine stream of gas completely ceased. The reaction was cooled down to room temperature to give black crude product. The black crude product was isolated and sublimed under vacuum to give the pure product 57.7 g (71% yield).

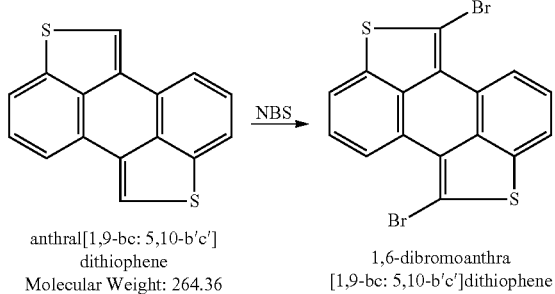

anthral[1,9-bc:5,10-b'c']
dithiophene
Molecular Weight: 264.36

1,6-dibromoanthra
[1,9-bc:5,10-b'c']dithiophene

Synthesis of 1,6-dibromoanthra[1,9-bc:5,10-b'c']
dithiophene anthra[1,9-bc:5,10-b'c']dithiophene (18 g, 0.0681 mol) was added to anhydrous DMF (1125 ml) in a 2000 ml three-neck round bottom flask. The suspension was heated to 140° C. under a nitrogen flow until all starting material was completely dissolved. The solution was cooled down to approximately 60° C. N-Bromosuccinimide (30.3 g, 0.1702 mol) in anhydrous DMF (191 ml) was slowly added into the reaction flask. The product immediately precipitated out. The mixture was heated to approximately 80° C. for 1 hour with vigorous stirring. After cooling, the precipitates were filtered, washed with acetone, and dried to give 27.44 g of product (95% yield).

Example 16: Core Synthesis

Synthesis of 4,8-bis(3-ethylhept-1-ynyl)thieno[2,3-f]benzothiophene

A dry 500-mL three-neck flask with an attached reflux condenser was flushed with $N_2$ and was charged with 3-ethylhept-1-yne (10.5 g, 0.084 mol) and THF (200 mL, 0.4 M) via deoxygenated syringe. The reaction flask was cooled to 0° C. and a 2.5 M solution of n-butyllithium in hexanes (32.2 mL, 0.080 mol) was added dropwise via deoxygenated syringe. After 30 minutes of stirring at 0° C., the solution was warmed to ambient temperature and benzo[1,2-b:4,5-b']dithiophene-4,8-dione (4.43 g, 0.02 mol) was added portion-wise. The reaction was stirred at ambient temperature for 3 days. As the reaction was completed, cool DI water (3 mL) was slowly added to the reaction flask. A solution of $SnCl_2$ (3 g) dissolved in 10% HCl (10 mL) was added to the reaction and stirred, increasing temperature to reflux for 1 hour and then cooling the reaction to ambient temperature. The reaction was poured into 200 mL of cool water with 10 mL of 10% HCl and extracted with hexanes (300 mL) three times. The combined organic layer was dried over anhydrous magnesium sulfate ($MgSO_4$). After the product was filtered, the solvent was removed by rotary evaporation. The product was purified using column chromatography on silica gel with hexanes/chloroform (gradient) to yield a colorless oil (3.0 g, 35%).

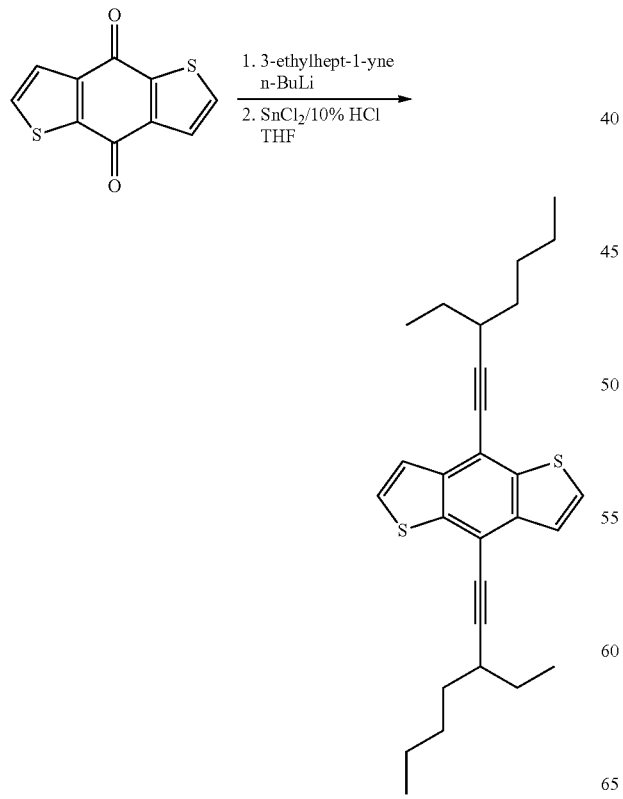

Synthesis of 4,8-bis(3-ethylheptyl)thieno[2,3-f]benzothiophene

A dry 250 mL 1-neck flask was flushed with $N_2$ and was charged with 4,8-bis(3-ethylhept-1-ynyl)thieno[2,3-f]benzothiophene (3.04 g, 0.007 mol), Pd/C wet support (0.82 g, 10%) and THF (15 mL, 0.5 M). The flask was evacuated and backfilled with hydrogen. The flask was kept under a hydrogen atmosphere and was monitored by TLC. After the reaction was completed, the mixture was filtered through Celite and solvent was removed by rotary evaporation.

Example 17: Core Synthesis

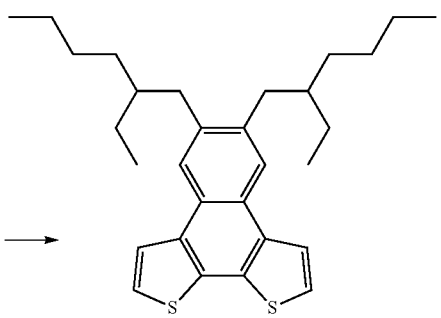 [SMILES: CCCCC(CC)Cc1cc2c(cc1CC(CC)CCCC)c1ccsc1c1sccc21]

The synthesis of this compound is described in US Patent Publication No. 2011/0028644 (assignee: Plextronics, Inc.).

Example 18: Core Synthesis

The moiety below comprising three thiophenes fused to a central phenyl ring can be used as a core to prepare arylamine hole transporting compounds. A synthesis strategy is described in US Patent Publication 2011/0028644.

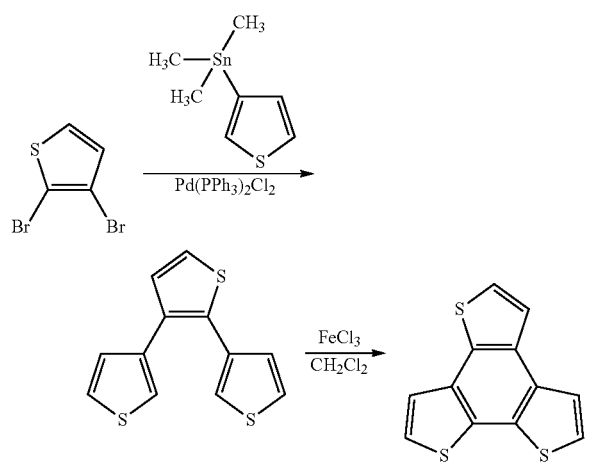

Example 19: Arylamine, Stabilizing Group Synthesis

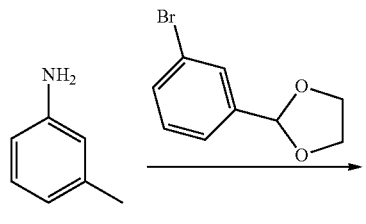

Molecular Weight: 107.15

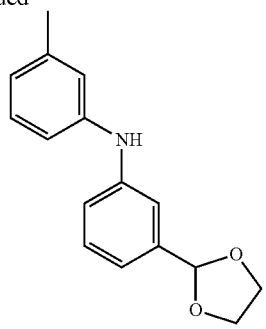

Molecular Weight: 255.31

Synthesis of N-(3-(1,3-dioxolan-2-yl)phenyl)-3-methylaniline

To a clean and dry 500 ml round bottom flask equipped with a reflux condenser and magnetic stir bar nitrogen was purged and anhydrous toluene (250.0 ml) was added by cannula. m-toluidine (5.1 ml, 0.0467 mol) was added to the reaction flask by syringe. Next, 2-(3-bromophenyl)-1,3-dioxolane (7.8 ml, 0.0513 mol) was added by syringe. The reaction solution was purged with a strong nitrogen flow for 30 minutes. Sodium tert-butoxide (6.73 g, 0.0701 mol) and Pd2dba3 (0.85 g, 0.0009 mol) were then added manually, followed by the addition of tri-tert-butylphosphine (0.57 g, 0.0028 mol) in toluene (~8 ml) via syringe. The vessel was heated to reflux for approximately 4 hours. The reaction was then cooled to room temperature and filtered through a Celite and silica gel pad. Solvent was removed by rotary evaporation. The crude material was partially dissolved in a 10% ethyl acetate/hexane solution (20.0 ml) and purified by flash column chromatography providing near pure product. Further purification was carried out using an automatic column chromatography system using 5% ethyl acetate/hexane as an eluent. This provided pure product confirmed by NMR.

Example 20: Arylamine, Stabilizing Group Synthesis

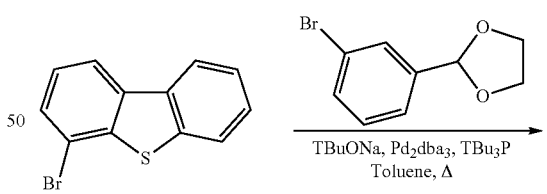

Molecular Weight: 263.15

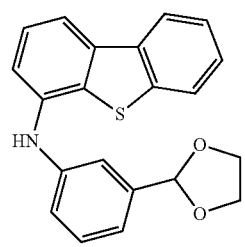

Molecular Weight: 347.43

Synthesis of N-(3-(1,3-dioxolan-2-yl)phenyl)dibenzo[b,d]thiophen-4-amine

A clean and dry 1000 ml round bottom flask equipped with a reflux condenser, magnetic stir bar, and thermometer with adapter was prepared and purged with nitrogen. A solution of 4-bromodibenzo[b,d]thiophene (RS-1-170, 10.7 g, 0.0407 mol) in anhydrous toluene (500.0 ml) was then prepared and transferred to the reaction flask via cannula. 3-aminobenzaldehyde ethylene acetal (8.1 g, 0.0488 mol) was added by syringe. The reaction solution was purged with a strong nitrogen flow for 20 minutes. Sodium tert-butoxide (5.86 g, 0.0610 mol) and Pd2dba3 (1.10 g, 0.0012 mol) were then added manually, followed by the addition of tri-tert-butylphosphine (0.65 g, 0.0032 mol) in toluene (~10 ml) via syringe. The vessel was heated to reflux for approximately 2 hours. The reaction was then cooled to room temperature and filtered through a Celite and silica gel pad. Solvent was removed by rotary evaporation. The crude material was dissolved in a 2:1 hexane/ethyl acetate solution purified by flash column chromatography using a gradient elution system of ethyl acetate/hexane. This provided pure product confirmed by NMR.

Example 21: Arylamine, Stabilizing Group Synthesis

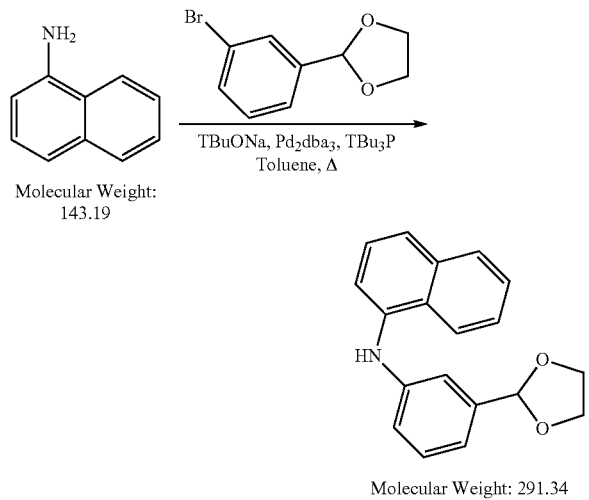

Synthesis of N-(3-(1,3-dioxolan-2-yl)phenyl)naphthalen-1-amine

A clean and dry 500 ml round bottom flask equipped with a reflux condenser, magnetic stir bar, and thermometer with adapter was prepared and purged with nitrogen. Anhydrous toluene (250.0 ml) was transferred to this flask by cannula. 2-(3-bromophenyl)-1,3-dioxolane (6.0 ml, 0.0397 mol) was added by syringe followed by the manual addition of 1-naphthylamine (5.08 g, 0.0355 mol). The reaction solution was purged with a strong nitrogen flow for 30 minutes. Sodium tert-butoxide (5.60 g, 0.0583 mol) and Pd2dba3 (0.65 g, 0.0007 mol) were then added manually, followed by the addition of tri-tert-butylphosphine (1.30 g, 0.0064 mol) in toluene (~10 ml) via syringe. The vessel was heated to reflux for approximately 5 hours. The reaction was then cooled to room temperature and filtered through a Celite and silica gel pad washing thoroughly with acetone and chloroform. Solvent was removed by rotary evaporation. The crude material was purified by flash column chromatography using ethyl acetate/hexane as an eluent. This provided pure product confirmed by NMR spectroscopy.

Example 22: Intermediate

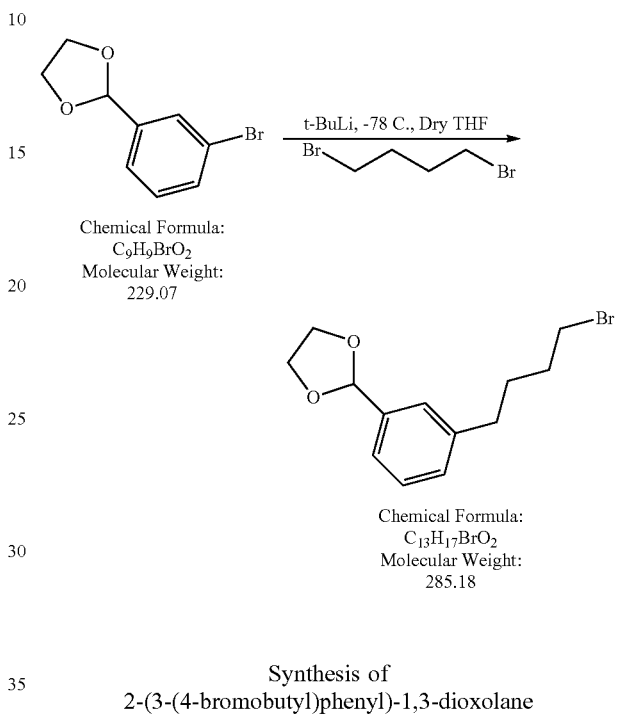

Synthesis of 2-(3-(4-bromobutyl)phenyl)-1,3-dioxolane

To a clean and dry 2000 ml round bottom flask equipped with a 500 ml addition funnel, low temperature thermometer and magnetic stir bar was transferred anhydrous tetrahydrofuran (800.0 ml) under nitrogen. 2-(3-bromophenyl)-1,3-dioxolane (33.0 ml, 0.2183 mol) was added to this flask by syringe. The reaction vessel was placed into a dry ice/acetone bath until a temperature of <−65° was achieved. The reaction mixture was then allowed to stir for 45 minutes at a stirring speed of 550 rpm in order to verify the integrity of the stirring apparatus at this temperature. Tert-butyllithium solution (257.0 ml, 0.4690 mol) was transferred to the addition funnel by cannula, then added drop wise to the reaction never allowing the temperature to rise above −65° C. Following addition, the reaction was allowed to stir for a period of 30 minutes. The vessel was then removed from the dry ice/acetone bath and allowed to warm to a temperature of −20° C. The vessel was then again placed into the dry ice/acetone bath until a temperature of <−65° was achieved. 1,4-dibromobutane (103.5 ml, 0.8740 mol) was added to the reaction dropwise via syringe, maintaining the current temperature. The reaction was allowed to stir for 30 minutes at this temperature following addition. The reaction was slowly warmed to room temperature over the following 12 hours. After warming, the reaction was quenched by the addition of isopropanol (20.0 ml) via syringe.

After quenching, solvent was removed by rotary evaporation using a maximum temperature of 70° C. Methyl tert-butyl ether (700.0 ml) was added and the solution was washed with deionized water (200.0 ml×8). The organic fraction was collected and dried over anhydrous sodium sulfate. Solids were then removed by vacuum filtration over a bed of Celite. Solvent was removed by rotary evaporation using a maximum temperature of 70° C. The crude product was then purified by vacuum distillation at 100° C. for 4 hours to remove most of 1,4-dibromobutane. Further purification was carried out by automatic flash column chromatography on silica gel using 3% ethyl acetate/97% hexane as an eluent. This provided pure product confirmed by NMR and GC-MS.

Example 23: Intermediate-2

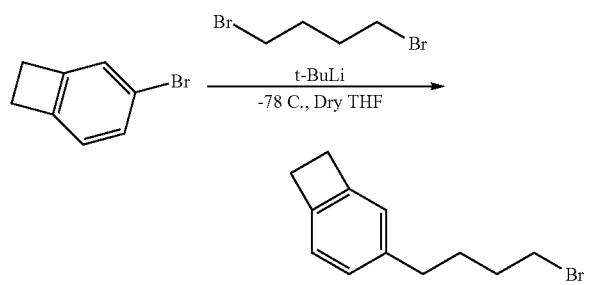

Synthesis of 3-(4-bromobutyl)bicyclo[4.2.0]octa-1(6),2,4-triene

To a clean and dry 1000 ml round bottom flask equipped with a 250 ml addition funnel, low temperature thermometer and magnetic stir bar was transferred anhydrous tetrahydrofuran (500.0 ml) under nitrogen. 4-bromobenzocyclobutane (25.0 g, 0.1370 mol) was added to this flask by syringe. The reaction vessel was placed into a dry ice/acetone bath until a temperature of <−70° C. was achieved. The reaction mixture was then allowed to stir for 45 minutes at a stirring speed of 550 rpm in order to verify the integrity of the stirring apparatus at this temperature. Tert-butyllithium solution (161 ml, 0.2730 mol) was transferred to the addition funnel by cannula, then added dropwise to the reaction never allowing the temperature to rise above −65° C. Following addition, the reaction was allowed to stir for a period of 30 minutes. The vessel was then removed from the dry ice/acetone bath and allowed to warm to a temperature of −20° C. The vessel was then again placed into the dry ice/acetone bath until a temperature of <−70° was achieved. 1,4-dibromobutane (64.7 ml, 0.5460 mol) was added to the reaction dropwise via syringe, maintaining the current temperature. The reaction was allowed to stir for 30 minutes at this temperature following addition. The reaction was slowly warmed to room temperature over the following 12 hours. Reaction completion was confirmed by GC-MS. After warming, the reaction was quenched by the addition of isopropanol (25.0 ml) via syringe.

After quenching, solvent was removed by rotary evaporation. Ethyl acetate (500 ml) was added and the solution was washed with DI water/brine (1000 ml×2, 200 ml×5). The organic fraction was collected and dried over anhydrous magnesium sulfate. Solids were then removed by gravity filtration and solvent was removed by rotary evaporation. The crude product was then purified by vacuum distillation at a temperature of 90° C. for 4 hours to remove excess 1,4-dibromobutane. This provided pure product confirmed by NMR and GC-MS.

Comparative Example A

Polymers with similar cross linking functionality were used as a blender in the HTL formulation to increase the overall molecule weight and also act as a spacer between small molecule hence, in an attempt to prevent the formation of bead like structures in the HTL. However, these films showed anywhere between 5-20% film loss with toluene wash.

What is claimed is:

1. A composition comprising:
   at least one first compound and at least one second compound different from the first,
   wherein the at least one first compound comprises a hole transporting core which is a fluorene core or a biphenyl core, wherein the hole transporting core is covalently bonded to a first arylamine group and also covalently bonded to a second arylamine group, and wherein the core is further covalently bonded to at least two solubilizing groups comprising at least four carbon atoms and selected from substituted or unsubstituted $C_4$ to $C_{30}$ alkyl or heteroalkyl groups, and wherein the solubilizing groups are optionally substituted with intractability groups;
   wherein the at least one second compound comprises a hole transporting core which is a fluorene or a biphenyl core, wherein the hole transporting core is covalently bonded to a first arylamine group and also covalently bonded to a second arylamine group, wherein the second compound further comprises at least one intractability group which is bonded to the first arylamine group, or to the second arylamine group, or to both;
   wherein the first and second compounds have molecular weight of about 5,000 g/mole or less.

2. The composition of claim 1, wherein for the first compound, the solubilizing group is substituted with the intractability group, and for the second compound the core further comprises at least two solublizing groups comprising at least four carbon atoms.

3. The composition of claim 2, wherein the intractability group for the second compound is vinyl.

4. The composition of claim 1, wherein for the first compound, the solubilizing group of the core is unsubstituted with intractability group.

5. The composition of claim 4, wherein the intractability group for the second compound is vinyl.

6. The composition of claim 1, wherein for the first compound, the solublizing group is substituted with the intractability group and the for the second compound, the core does not comprise at least two solublizing groups comprising at least four carbon atoms.

7. The composition of claim 6, wherein the intractability group for the second compound is vinyl.

8. The composition of claim 1, wherein the composition further comprises a solvent system to form an ink.

9. The composition of claim 8, wherein the intractability group for the second compound is vinyl.

10. A composition prepared by reaction of the first and second compounds of the composition of claim 1.

11. The composition of claim 10, wherein the intractability group for the second compound is vinyl.

12. The composition of claim 1, wherein the composition further comprises at least one third compound, different from the first and second compounds, which activates a polymerization reaction for the composition.

13. The composition of claim 12, wherein the intractability group for the second compound is vinyl.

14. The composition of claim 1, wherein the hole transporting core of the first compound and of the second compound is a fluorene core.

15. The composition of claim 14, wherein the intractability group for the second compound is vinyl.

16. The composition of claim 1, wherein the intractability group for the second compound is vinyl.

* * * * *